United States Patent
Mickle et al.

(10) Patent No.: US 12,012,384 B2
(45) Date of Patent: Jun. 18, 2024

(54) DEXTRORPHAN PRODRUGS AND PROCESSES FOR MAKING AND USING THEM

(71) Applicant: ZEVRA THERAPEUTICS, INC., Celebration, FL (US)

(72) Inventors: Travis Mickle, Celebration, FL (US); Sven Guenther, Coralville, IA (US); Sanjib Bera, Blacksburg, VA (US)

(73) Assignee: ZEVRA THERAPEUTICS, INC., Celebration, FL (US)

( * ) Notice: Subject to any disclaimer, the term of this patent is extended or adjusted under 35 U.S.C. 154(b) by 138 days.

(21) Appl. No.: 17/537,291

(22) Filed: Nov. 29, 2021

(65) Prior Publication Data
US 2022/0089544 A1    Mar. 24, 2022

Related U.S. Application Data

(63) Continuation of application No. 16/604,755, filed as application No. PCT/US2018/027266 on Apr. 12, 2018, now Pat. No. 11,214,544.

(60) Provisional application No. 62/485,894, filed on Apr. 14, 2017.

(51) Int. Cl.
  *C07D 221/28*    (2006.01)
  *A61K 47/54*    (2017.01)

(52) U.S. Cl.
  CPC .......... *C07D 221/28* (2013.01); *A61K 47/542* (2017.08)

(58) Field of Classification Search
  CPC ... C07D 221/28; C07D 221/22; A61K 31/439
  USPC .............................................. 546/74; 514/289
  See application file for complete search history.

(56) References Cited

U.S. PATENT DOCUMENTS 8,829,020 B2 * 9/2014 Cantrell ............... A61K 31/485
                                                     514/289
11,234,975 B2 * 2/2022 Mickle ................. C07D 221/28

* cited by examiner

*Primary Examiner* — Charanjit Aulakh
(74) *Attorney, Agent, or Firm* — MCANDREWS HELD & MALLOY, LTD

(57) ABSTRACT

The presently described technology provides compositions of one or more of oxoacids, polyethylene glycols, and/or vitamin compounds chemically conjugated to dextrorphan, (+)-17-methylmorphinan-3-ol), to form novel prodrugs and compositions of dextrorphan.

4 Claims, 18 Drawing Sheets

STRUCTURES OF SOME HYDROXYBENZOATES

STRUCTURES OF SOME HETEROARYL CARBOXYLIC ACIDS

STRUCTURES OF SOME PHENYLACETATES

FIGURE 5
STRUCTURES OF SOME BENZYLACETATES
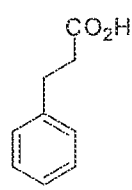
3-phenylpropanoic acid
(benzylacetic acid)
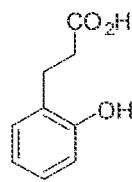
Melilotic acid
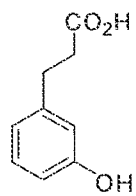
3-hydroxyphenyl-
propanoic acid
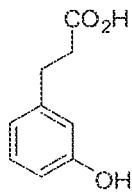
4-hydroxyphenyl-
propanoic acid
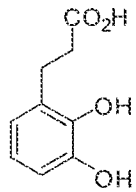
2,3-dihydroxyphenyl-
propanoic acid
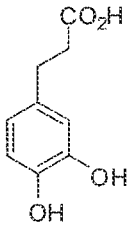
3,4-dihydroxyphenyl-
propanoic acid
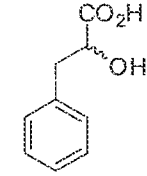
Phenyllactic acid

STRUCTURES OF SOME CINNAMATES

FIGURE 7
STRUCTURES OF SOME DICARBOXYLIC ACIDS

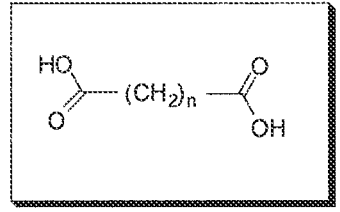

When
n = 0    Oxalic acid
n = 1    Malonic acid
n = 2    Succinic acid
n = 3    Glutaric acid
n = 4    Adipic acid
n = 5    Pimelic acid
n = 6    Suberic acid
n = 7    Azelaic acid
n = 8    Sebacic acid

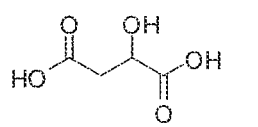 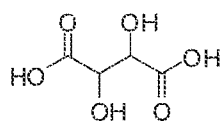 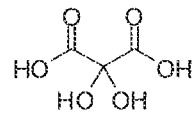 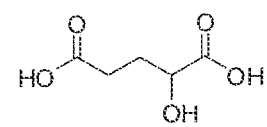

Malic acid    Tartaric acid    dihydroxymesoxalic acid    α-hydroxyglutaric acid

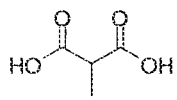 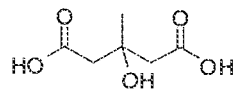 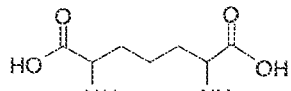 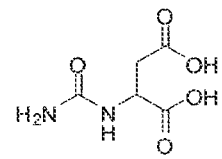

Methylmalonic acid    Meglutol    Diaminopimelic acid    Carbamoyl aspartic acid

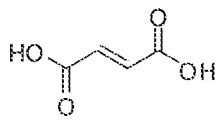 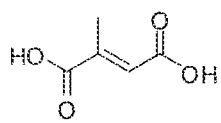 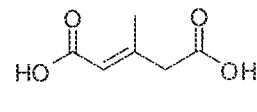

Fumaric acid (trans isomer)    Mesaconic acid    3-methylglutaconic acid
Maleic acid (cis isomer)

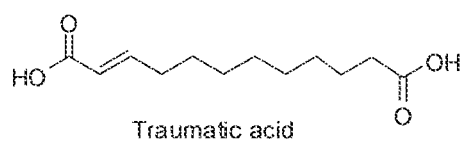

Traumatic acid

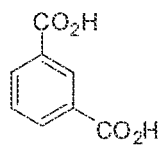 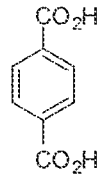 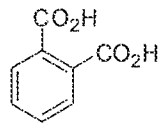 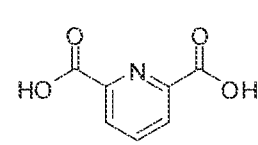

Isophthalic acid    Terephthalic acid    Phthalic acid    Dipicolinic acid

FIGURE 8
STRUCTURES OF SOME TRICARBOXYLIC ACIDS
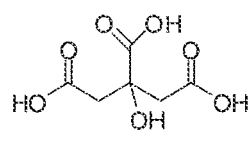
Citric acid
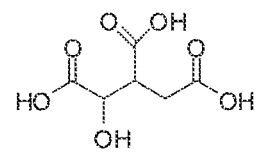
Isocitric acid
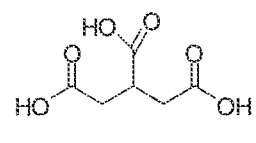
Carballyilc acid
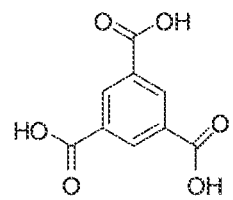
Trimesic acid

GENERAL STRUCTURES OF THE STANDARD AMINO ACIDS

FIGURE 10
STRUCTURES OF SOME NON-STANDARD AMINO ACIDS
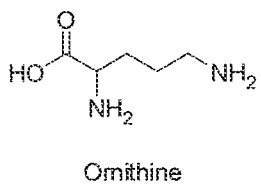
Ornithine
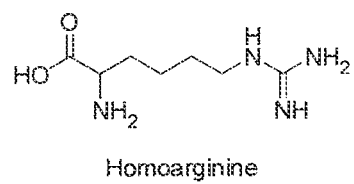
Homoarginine
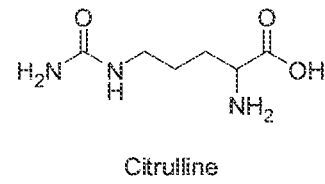
Citrulline
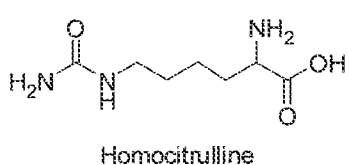
Homocitrulline
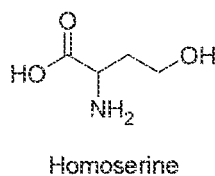
Homoserine
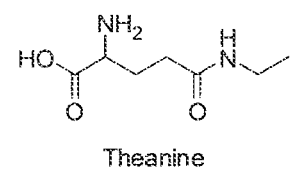
Theanine
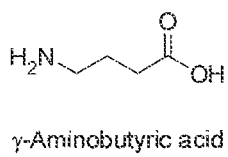
γ-Aminobutyric acid
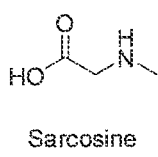
Sarcosine
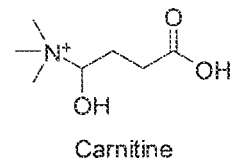
Carnitine
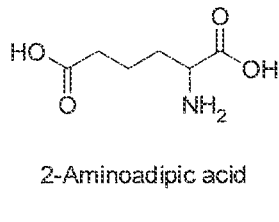
2-Aminoadipic acid
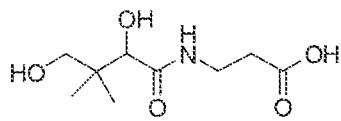
Pantothenic acid
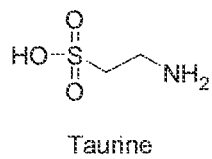
Taurine
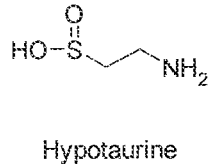
Hypotaurine
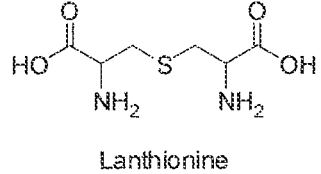
Lanthionine
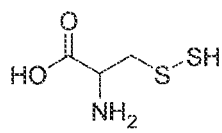
Thiocysteine
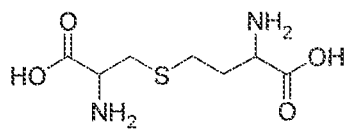
Cystathionine
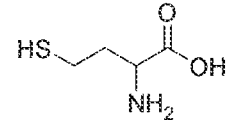
Homocysteine FIGURE 10 (CONT.)
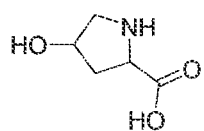 
4-Hydroxyproline
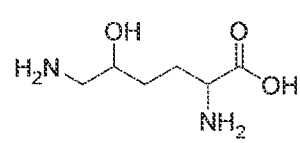 
5-Hydroxylysine
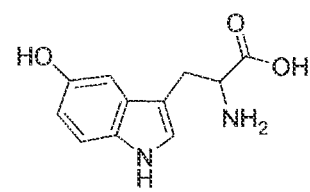 
5-Hydroxy-tryptophan
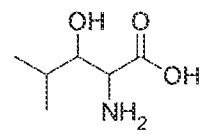 
3-Hydroxyleucine
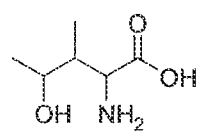 
4-Hydroxyisoleucine
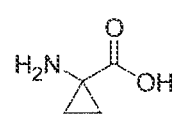 
1-Aminocyclopropyl-1-carboxylic acid
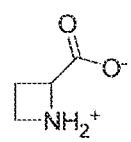 
Azetidine-2-carboxylic acid
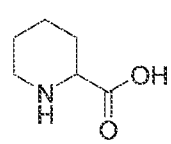 
Pipecolic acid

STRUCTURES OF SOME SYNTHETIC AMINO ACIDS

FIGURE 12A
CHEMICAL STRUCTURES OF WATER SOLUBLE VITAMINS
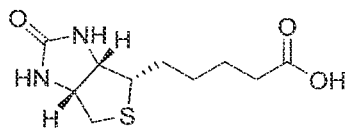
Biotin (Vitamin B$_7$)
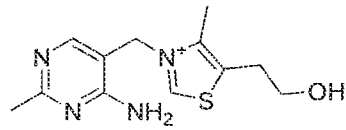
Thiamin (Vitamin B$_1$)
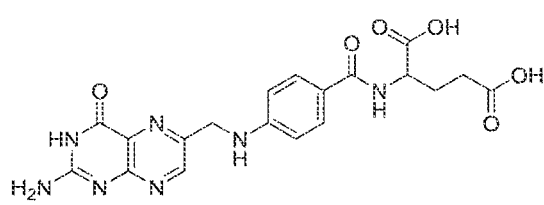
Folic Acid
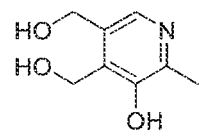
Pyridoxine (Vitamin B$_6$)
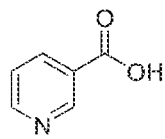
Niacin
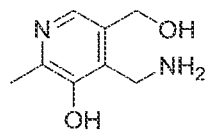
Pyridoxamine (Vitamin B$_6$)
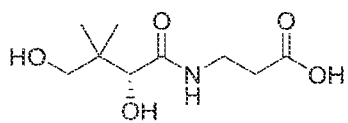
Pantothenic acid (Vitamin B$_5$)
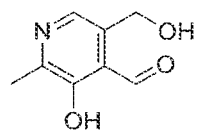
Pyridoxal (Vitamin B$_6$)
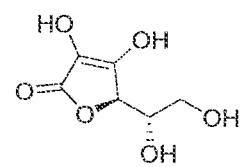
Ascorbic acid (Vitamin C)
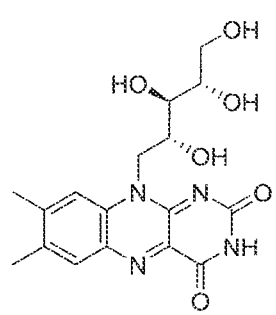
Riboflavin (Vitamin B$_2$)

FIGURE 12B
CHEMICAL STRUCTURES OF FAT SOLUBLE VITAMINS
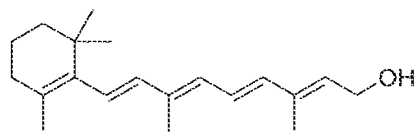
Retinol (Vitamin A)
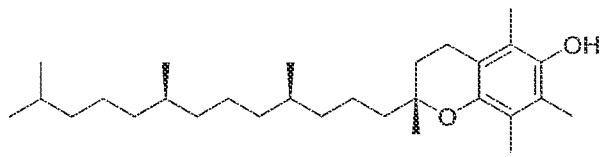
Alpha-tocopherol (Vitamin E)
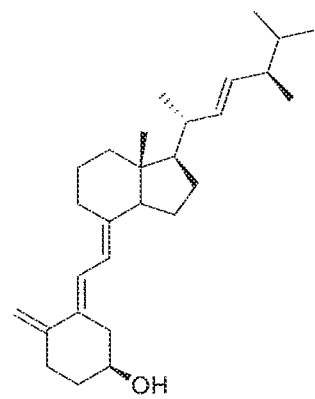
Calciferol (Vitamin $D_2$)
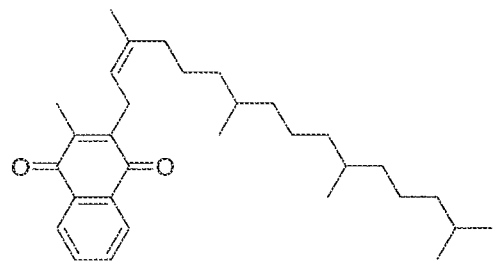
Phylloquinone (Vitamin $K_1$)
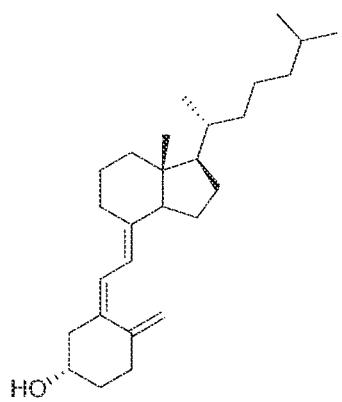
Cholecalciferol (Vitamin $D_3$)

DEXTRORPHAN PRODRUGS AND PROCESSES FOR MAKING AND USING THEM

CROSS REFERENCE TO RELATED APPLICATIONS

This application is a continuation of U.S. patent application Ser. No. 16/604,755, filed Oct. 11, 2019 and claims priority to International Patent Application No. PCT/US2018/027266 which was filed Apr. 12, 2018, which claims priority to U.S. provisional application No. 62/485,894, filed on Apr. 14, 2017, which is herein incorporated by reference in its entirety. This application is also related to U.S. provisional application No. 62/485,888, filed on Apr. 14, 2017; U.S. provisional application No. 62/485,890, filed on Apr. 14, 2017; and U.S. provisional application No. 62/485,891, filed on Apr. 14, 2017.

BACKGROUND

Opioids are highly effective as analgesics and are commonly prescribed for the treatment of acute and chronic pain. They are also commonly used as antitussives. The opioids, however, also produce euphoria and are highly addictive. As a result, they are often abused with far reaching social and health related consequences.

Because of the inherent potential for abuse, it is desirable that any pharmaceutical composition containing an opioid agonist be made as abuse-resistant or abuse-deterrent as practical. Illicit users often will attempt to circumvent the extended release properties of these dosage forms by injecting or otherwise misusing the product in order to achieve an immediate release of the opioid agonist.

Dextrorphan ((+)-17-methylmorphinan-3-ol) is the (+)-isomer and one of two enantiomers of 17-methylmorphinan-3-ol. The other enantiomer is levorphanol ((−)-17-methylmorphinan-3-ol). A 1:1 mixture of both enantiomers (dextrorphan and levorphanol) is referred to as racemorphan.

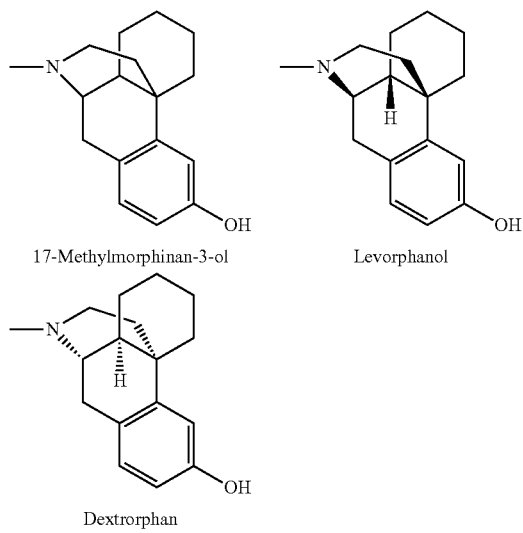

17-Methylmorphinan-3-ol        Levorphanol

Dextrorphan

It should be appreciated by those skilled in the art that different stereochemistry may impact the pharmacodynamics, pharmacological and/or pharmacokinetic properties, among other properties, of each isomer or racemic mixture utilized. Further, it should also be appreciated that various conjugations of the isomers to various ligands may also impact the pharmacodynamics, pharmacological and/or pharmacokinetic properties, among other properties, of each resultant conjugate, formulation, and/or end product. For example, those skilled in the art can appreciate the pharmacodynamics, pharmacological and/or pharmacokinetic property differences exhibited and/or observed by different enantiomers (dextrorphan and levorphanol) as well as a mixture such as racemorphan. Moreover, those skilled in the art, also appreciate that the conjugation of those various different enantiomers may impact the various properties observed for the resultant dextrorphan or levorphanol conjugate, formulation and/or end product. Furthermore, those skilled in the art can recognize that conjugation to dextrorphan, levorphanol, or a mixture thereof, may create new enantiomers or diastereomers that may affect their resulting pharmacodynamic, pharmacological and/or pharmacokinetic properties.

Dextrorphan is a psychoactive drug of the morphinan class which acts as an antitussive or cough suppressant and dissociative hallucinogen. It is also an active metabolite of dextromethorphan that forms after O-demethylation by CYP2D6. Dextrorphan is an NMDA (N-methyl-D-aspartate) receptor antagonist. Dextrorphan also binds to the $\sigma_1$-receptor, and to a lesser extent to the norepinephrine reuptake transporter (NET) and to the serotonin reuptake transporter (SERT). Dextrorphan can act, for example, as an anesthetic and antitussive.

The present technology utilizes covalent conjugation of dextrorphan with certain oxoacids including amino acids, as well as with polyethylene glycols (PEG or PEO), and/or vitamin compounds to decrease its potential for causing overdose or abuse by requiring the active dextrorphan to be released through enzymatic or metabolic breakdown of the conjugate in vivo. The present technology also provides methods of delivering dextrorphan as conjugates that release the dextrorphan following oral administration while being resistant to abuse by circuitous routes such as intravenous ("shooting") injection and intranasal administration ("snorting"). The compounds and conjugates of this disclosure (aka prodrugs) may be administered alone, or combined with other active ingredients, for the treatment of conditions including, but not limited to, cough, pseudobulbar affect (PBA), neuropathy, diabetic peripheral neuropathic pain, catalepsy, amnesia, Alzheimer's disease, depression, and post-traumatic stress disorder (PTSD).

BRIEF SUMMARY

The present technology utilizes conjugation of the dextrorphan with certain oxoacids (including amino acids), polyethylene glycols (PEG or PEO), and/or vitamin compounds to decrease its potential for causing overdose or abuse by requiring the active dextrorphan to be released through enzymatic or metabolic breakdown of the conjugate in vivo. The present technology also provides methods of delivering dextrorphan as conjugates that release the dextrorphan following oral administration while being resistant to abuse by circuitous routes such as intravenous ("shooting") injection and intranasal administration ("snorting").

Advantages of certain embodiments of the dextrorphan prodrugs of the present technology include, but are not limited to, reduced risk of chemical or physical manipulation resulting in full dosage of dextrorphan release, reduced patient to patient variability in plasma concentrations compared to free dextrorphan, improved dosage forms through modifications of the physical and chemical properties of the prodrugs.

In some aspects, the present technology provides an immediate release composition of conjugated dextrorphan that allows delivery of the dextrorphan into the blood system of a human or animal in a therapeutically bioequivalent manner upon oral administration. In at least one aspect, the compositions/formulations of the current technology can lessen common side effects associated with unconjugated dextrorphan and similar compounds. The presently described technology, in at least one aspect, provides a slow/sustained/controlled release composition of conjugated dextrorphan that allows slow/sustained/controlled delivery of the dextrorphan into the blood system of a human or animal within a therapeutic window upon, for example, oral administration.

In one aspect, the present technology provides a composition comprising at least one conjugate of dextrorphan, and at least one oxoacid, polyethylene glycol, vitamin compound, derivatives thereof, or combinations thereof. In some aspects, the conjugate further comprises a linker, wherein the linker chemically bonds the at least one dextrorphan with the at least one oxoacid, polyethylene glycol, vitamin compound, or derivatives thereof.

In another aspect, the present technology provides at least one conjugate of dextrorphan, and at least one oxoacid, polyethylene glycol, vitamin compound, derivatives thereof, or combinations thereof. In some aspects, the conjugate further comprises a linker, wherein the linker chemically bonds the at least one dextrorphan with the at least one oxoacid, polyethylene glycol, vitamin compound, or derivatives thereof.

In a further aspect, the present technology provides a composition comprising at least one conjugate of dextrorphan, wherein the conjugate has the following general Formula IA:

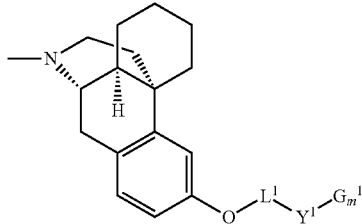

Formula IA where $L^1$ is absent, or is

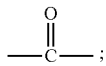

$Y^1$ is absent, or $[A-X-Z]_n$
where A, X, Z are independently absent or selected from
—O—, —S— or —$(CR^1R^2)_k$—
$R^1$, $R^2$ are independently selected from H, alkyl, aryl, alkylaryl, alkoxy, haloalkyl, or haloaryl
n and k are independently 1-4
$G_m^1$ is absent or selected independently for each repeating subunit from H, oxoacid, polyethylene glycol having from 2 to 5 ethylene oxide units, or a vitamin compound, and m is 1-4, except that m is 1 when $G^1$ is a hydrogen atom;
or a pharmaceutically acceptable salt thereof.

In a further aspect, the present technology provides a composition comprising at least one conjugate of dextrorphan, wherein the conjugate has the following general Formula IB:

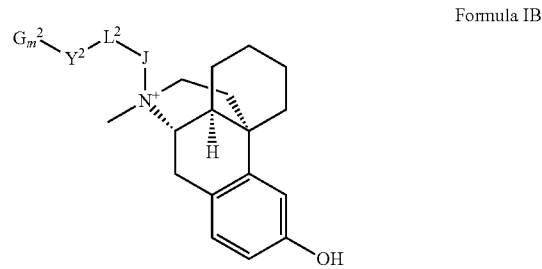

Formula IB where $L^2$ is absent, or is

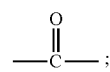

$Y^2$ is absent, or $[A-X-Z]_n$
where A, X, Z are independently absent or selected from
—O—, —S— or —$(CR^1R^2)_k$—
J is $[M-W]_p$
where M is absent, or —$(CR^3R^4)_q$—; and W is absent, or —O— or —S—
$R^1$, $R^2$, $R^3$, $R^4$ are each independently selected from H, alkyl, aryl, alkylaryl, alkoxy, haloalkyl, or haloaryl
n and k are independently 1-4
p and q are independently 1-4
$G_m^2$ is absent or selected independently for each repeating subunit from H, oxoacid, polyethylene glycol having from 2 to 5 ethylene oxide units, or a vitamin compound, and m is 1-4, except that m is 1 when $G^2$ is a hydrogen atom;
or a pharmaceutically acceptable salt thereof.

In a further aspect, the present technology provides a composition comprising at least one conjugate of dextrorphan, wherein the conjugate has the following general Formula IC:

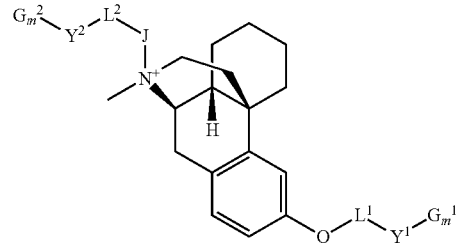

Formula IC where $L^1$ and $L^2$ are independently absent, or

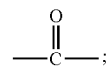

$Y^1$ and $Y^2$ are independently either absent, or $[A-X-Z]_n$,
where A, X, Z are independently selected for $Y^1$ and $Y^2$, and are independent of each other, either absent or selected from —O—, —S—, or —$(CR^1R^2)_k$—

J is $[M-W]_p$ where M is absent, or —$(CR^3R^4)_q$—; and W is absent, or —O— or —S—

$R^1$ and $R^2$ are each independently selected for $Y^1$ and $Y^2$, and are, independent of each other, selected from H, alkyl, aryl, alkylaryl, alkoxy, haloalkyl, or haloaryl $R^3$ and $R^4$ are each independently selected from H, alkyl, aryl, alkylaryl, alkoxy, haloalkyl, or haloaryl for each $Y^1$ and $Y^2$, n is independently an integer of 1-4 for each repeating unit of $[A-X-Z]_n$, when $(CR^1R^2)_k$ is present, k is independently an integer of 1-4.

p and q are independently 1-4

$G_m^1$ and $G_m^2$ are independently absent, or selected independently of each other and, when present, each repeating subunit is independently selected from H, oxoacid, polyethylene glycol having from 2 to 5 ethylene oxide units, or a vitamin compound;

where m is selected independently for $G^1$ and $G^2$, and is an integer of 1-4, except that m is 1 when $G^1$ or $G^2$ is a hydrogen atom;

or a pharmaceutically acceptable salt thereof.

In another aspect, the present technology provides at least one prodrug or conjugate having the structure of general Formula 1A, 1B, or 1C.

In a further aspect, the present technology provides at least one prodrug composition comprising at least one conjugate of dextrorphan and at least one oxoacid, polyethylene glycol, vitamin compound, derivatives thereof, or combinations thereof. In some embodiments, the prodrug composition may also comprise conjugate combinations, and/or one or more active ingredients, additives, adjuvants, or combinations thereof.

In another aspect, the present technology provides at least one prodrug composition comprising at least one conjugate, where dextrorphan is conjugated at the C-3 hydroxyl position, and wherein the at least one conjugate can be, for example, 3-Val-dextrorphan; 3-(N-acetyl-Val)-dextrorphan; 3-(PhePhePhe)-dextrorphan; 3-(ValValPhe)-dextrorphan; 3-(AlaAlaVal)-dextrorphan; 3-(GlyGlyAla)-dextrorphan; 3-hippuryl-dextrorphan; 3-(N-acetyl-Tyr)-dextrorphan; 3-(N-acetyl-Ile)-dextrorphan; 3-(ProProPhe)-dextrorphan; 3-(GlyGly)-dextrorphan; 3-(ValGly)-dextrorphan; 3-(AlaPro)-dextrorphan; 3-cinnamoyl-dextrorphan; 3-biotinyl-dextrorphan; 3-(N,O-diacetyl-Tyr)-dextrorphan; 3-(N-acetyl-Val-OCH$_2$OC(O))-dextrorphan; 3-(cinnamoyl-OCH$_2$OC(O))-dextrorphan; 3-(benzoyl-OCH$_2$OC(O))-dextrorphan; 3-(butanoyl-OCH$_2$OC(O))-dextrorphan; 3-(N,O-acetyl-Lys-OCH$_2$OC(O))-dextrorphan; 3-(acetyl-OCH(CH$_3$)C(O))-dextrorphan; 3-(acetyl-OCH$_2$C(O))-dextrorphan; 3-(acetyl-OCH(phenyl)C(O))-dextrorphan; 3-(methoxy-PEG$_2$-CH$_2$C(O))-dextrorphan; 3-(methoxy-(ethoxy)-CH$_2$C(O))-dextrorphan; 3-(N-succinoyl-Val)-dextrorphan; 3-(H$_2$N-PEG$_4$-CH$_2$CH$_2$C(O))-dextrorphan; 3-(N$_3$-PEG$_4$-CH$_2$CH$_2$C(O))-dextrorphan; 3-(H$_2$N-PEG$_5$-CH$_2$CH$_2$C(O))-dextrorphan, 3-(propyl-SC(O))-dextrorphan, 3-(ethoxy-C(O))-dextrorphan and anionic salts thereof, including hydrochloride/chloride salts.

In another aspect, the present technology provides at least one prodrug composition comprising at least one conjugate, where dextrorphan is conjugated at the N-17 position, and wherein the at least one conjugate can be, for example, N-(acetyl-OCH$_2$)-dextrorphanium; N-(pivaloyl-OCH$_2$)-dextrorphanium; N-(Ser-Ile-CH$_2$)-dextrorphanium; N-(Val-CH$_2$)-dextrorphanium; N-(Phe-Val-CH$_2$)-dextrorphanium; 3-(Phe-CH(Me)C(O))—N-(nicotinoyl-OCH$_2$)-dextrorphanium; N-(MeO-PEG$_3$-CH$_2$C(O)OCH$_2$)-dextrorphanium; N—(HO-PEG$_4$-CH$_2$CH$_2$C(O)CH$_2$)-dextrorphanium; N—(BzO-CH$_2$OC(O)OCH$_2$)-dextrorphanium; N-(Ala-CH$_2$OC(O)OCH$_2$)-dextrorphanium; N-(Pro-Val-CH$_2$OC(O)OCH$_2$)-dextrorphanium; N-(thiaminyl-C(O)OCH$_2$)-dextrorphanium; N-(cinnamoyl-OCH$_2$SC(O)SCH$_2$)-dextrorphanium; and anionic salts thereof, including hydrochloride/chloride salts.

In another aspect, the present technology provides at least one prodrug composition comprising at least one conjugate, where dextrorphan is conjugated at both the C-3 hydroxyl and the N-17 position, and wherein the at least one conjugate can be, for example, 3-acetyl-N-(acetyl-OCH$_2$)-dextrorphanium; 3-(pivaloyl)-N-(pivaloyl-OCH$_2$)-dextrorphanium; 3-(ethoxy-C(O))—N-(ethoxy-C(O)CH(CH$_3$))-dextrorphanium; 3-(EtO-C(O))—N—(H$_2$N-PEG$_2$-CH$_2$CH$_2$C(O)OCH$_2$)-dextrorphanium; 3-(Ac-Val)-N-(Phe-Phe-CH$_2$)-dextrorphanium; 3-(acetylsalicyloyl-OCH$_2$OC(O))—N—(Ac-Val-CH$_2$)-dextrorphanium; 3-(Phe-CH(Me)C(O))—N-(nicotinoyl-OCH$_2$)-dextrorphanium, and salts thereof, including hydrochloride/chloride salts.

In yet another aspect, the present technology provides a method for chemically synthesizing any of the dextrorphan conjugates of the present technology by performing the appropriate steps to conjugate dextrorphan to at least one ligand.

In a further aspect, the present technology provides a method for treating a human or animal patient having a disease, disorder or condition requiring or mediated by binding of an NMDA receptor antagonist to an NMDA receptor of the patient, comprising orally administering to the patient a pharmaceutically effective amount of at least one dextrorphan conjugate of the present technology.

In another aspect, the present technology provides a pharmaceutical kit comprising a specified amount of individual doses in a package, each dose comprising a pharmaceutically effective amount of at least one conjugate of dextrorphan.

BRIEF DESCRIPTION OF THE DRAWINGS

FIG. 5. Chemical structures of some benzylacetates for use in the making of the conjugates of the present technology.

FIG. 7. Chemical structures of some dicarboxylic acids for use in the making of the conjugates of the present technology.

FIG. 8. Chemical structures of some tricarboxylic acids for use in the making of the conjugates of the present technology.

FIG. 12A. Chemical structures of some water soluble vitamins for use in the making of the conjugates of the present technology.

FIG. 12B. Chemical structures of some fat soluble vitamins for use in the making of the conjugates of the present technology.

DETAILED DESCRIPTION

Figure 1:
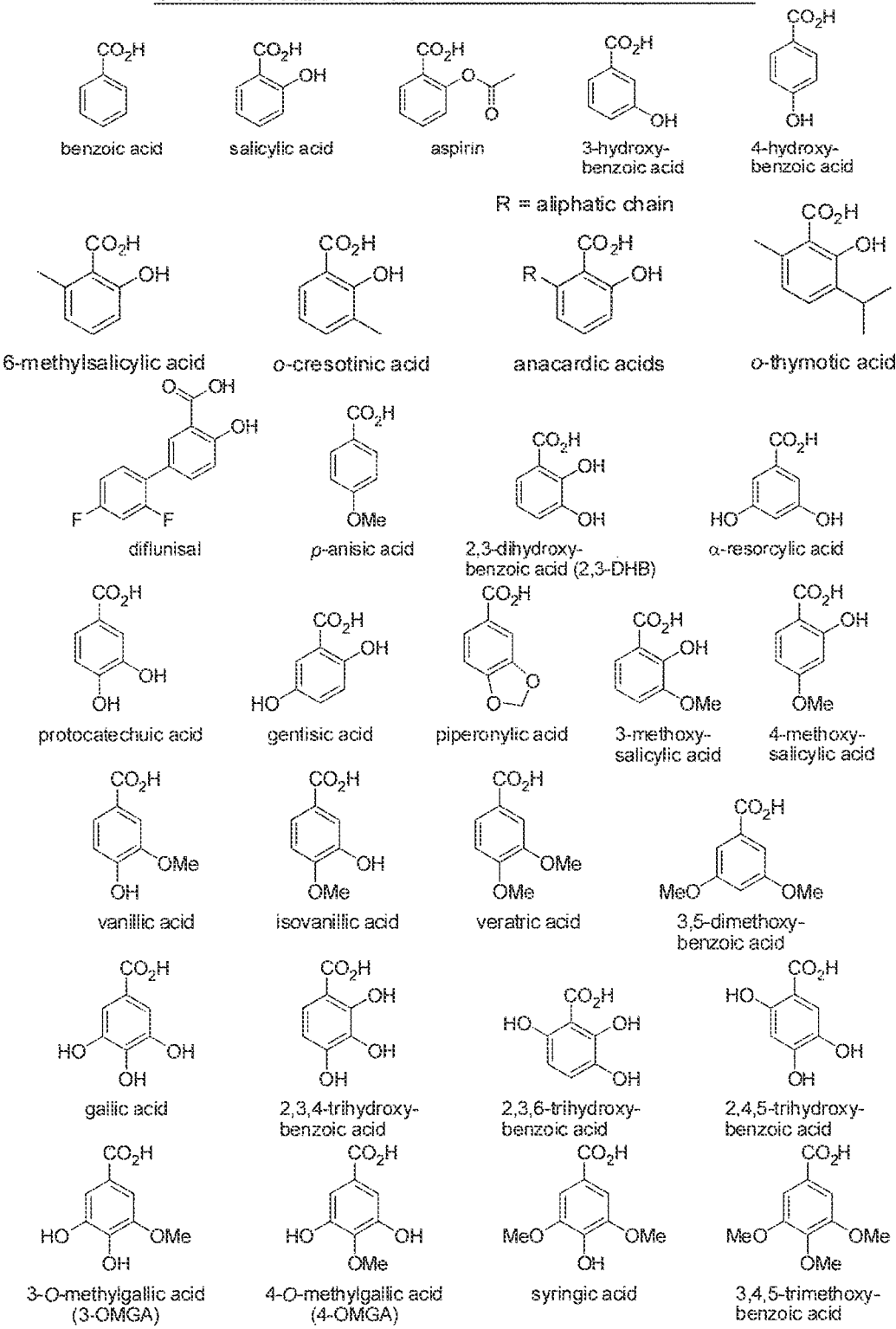
FIG. 1. Chemical structures of some hydroxybenzoates for use in the making of the conjugates of the present technology.

The present technology provides compounds of, or compositions comprising one or more oxoacids, polyethylene glycols and/or vitamin compounds ("ligands") that are chemically conjugated to dextrorphan ((+)-17-methylmorphinan-3-ol) to form novel prodrugs and conjugates of dextrorphan. In some embodiments, the chemical bond between the ligands and dextrorphan can be established by reacting the functional group of the ligand, either directly or through a linking group, with one of the following functional groups of dextrorphan:

(a) C-3 hydroxyl of dextrorphan,
(b) N-17 tertiary amine of dextrorphan,
(c) or both C-3 hydroxyl and N-17 tertiary amine of dextrorphan.

In some embodiments, the chemical bond between the ligands and dextrorphan can be established by reacting the C-3 hydroxyl of dextrorphan with the activated carboxylic acid function of an oxoacid or some vitamin compounds. In other embodiments, the hydroxyl group of an alcohol, hydroxyacid, hydroxyamino acid, or some vitamin compounds is conjugated to the C-3 of dextrorphan. In further embodiments, a hydroxyacid is used as a linker that is connected to the C-3 of dextrorphan on one end (by reaction with its hydroxyl group) and to an alcohol, hydroxyacid, hydroxyamino acid, or vitamin compound on the other end (by reaction with its carboxyl group). In yet further embodiments, a dicarboxylic acid is used as a linker that is connected to the C-3 of dextrorphan on one end and to an alcohol, hydroxyacid, hydroxyamino acid, or vitamin compound on the other end. In some embodiments, the chemical connection between dextrorphan and the oxoacids, polyethylene glycols, and/or vitamin compounds can be established through an N-alkyl linker by an alkylation reaction at the N-17 tertiary amine of dextrorphan to form a quaternary ammonium salt or dextrorphanium salt. In some embodiments, the oxoacids, polyethylene glycols, and/or vitamin compounds are directly connected to this N-alkyl linker. In other embodiments, a second linker is attached to the first N-alkyl linker, and the oxoacids, polyethylene glycols, and/or vitamin compounds are directly connected to the second linker. In further embodiments, the second linker may comprise an alcohol, hydroxyacid, or hydroxyamino acid.

The use of the term "dextrorphan" herein means the (+)-isomer of 17-methylmorphinan-3-ol, including all salt forms thereof. In some embodiments, the conjugates contain dextrorphan in a racemic mixture (racemorphan). In other embodiments, the dextrorphan conjugates are not in a racemic mixture. Depending on the chemical structure of the linkers and oxoacids, polyethylene glycol (PEG or PEO), and/or vitamin compounds, as well as the chiral composition of the dextrorphan to which they are attached, the resulting prodrug conjugates can be optically active mixtures of isomers, racemic mixtures, single isomers or combinations thereof.

As used herein, the term "conjugate" means a compound or substance formed by bonding two or more chemical compounds or substances in such a way that the bonding is reversible in vivo. For example, a conjugate is the resultant compound formed by bonding at least one pharmaceutical or therapeutically active ingredient with at least one ligand, such as at least one oxoacid, or other substance or compound capable of being a ligand, which is then broken down in vivo into the pharmaceutical or therapeutically active ingredient and ligand. One skilled in the art will appreciate that the term "conjugate" is used in a non-limiting manner and includes various forms including salts, polymorphs, among others.

As used herein, "normative patient" as used herein means a patient that, in general, meets or requires standard and/or established treatment modalities, treatment guidelines, prescribing guidelines, among others to achieve a variety of pharmaceutical and/or therapeutic outcomes.

As used herein, the term "prodrug" refers to a substance converted from an inactive or less active form of a drug to an active drug in the body by a chemical or biological reaction. In the present technology, the prodrug is a conjugate of at least one drug, dextrorphan, and at least one oxoacid, for example. Thus, the conjugates of the present technology are prodrugs and the prodrugs of the present technology are conjugates.

Prodrugs are often useful because, in some embodiments, they may be easier to administer or process than the parent drug. They may, for instance, be more bioavailable by oral administration whereas the parent drug is not. The prodrug may also have improved solubility in pharmaceutical compositions over the parent drug. An embodiment of a prodrug would be a dextrorphan conjugate that is metabolized to reveal the active moiety. In certain embodiments, upon in vivo administration, a prodrug is chemically converted to the biologically, pharmaceutically or therapeutically more active form of the compound. In certain embodiments, a prodrug is enzymatically metabolized by one or more steps or processes to the biologically, pharmaceutically or therapeutically active form of the compound. To produce a prodrug, a pharmaceutically active compound is modified such that the active compound will be regenerated upon in vivo administration. The prodrug is designed to alter the metabolism, pharmacokinetics, or the transport characteristics of a drug in certain embodiments, to reduce or lessen side-effects or toxicity, to improve bioavailability and/or water solubility, to improve the flavor of a drug or to alter other characteristics or properties of a drug in other discrete embodiments.

In some embodiments, the present technology provides at least one prodrug composition comprising at least one conjugate. The at least one conjugate may comprise at least one dextrorphan and at least one oxoacid, polyethylene glycol, vitamin compound, derivatives thereof, or combinations thereof. In some embodiments, the conjugate further comprises at least one linker. The linker chemically bonds the dextrorphan to the oxoacid, polyethylene glycol, or vitamin compound via one or more covalent bonds.

Depending on the linker and/or the oxoacid, polyethylene glycol, or vitamin compound conjugated to dextrorphan or derivative thereof, the at least one prodrug or conjugate formed can be either a neutral (uncharged), a free acid, a free base or a pharmaceutically acceptable anionic salt form or salt mixtures with any ratio between positive and negative components. These anionic salt forms can include, but are not limited to, for example, acetate, l-aspartate, besylate, bicarbonate, carbonate, d-camsylate, l-camsylate, citrate, edisylate, formate, fumarate, gluconate, hydrobromide/bromide, hydrochloride/chloride, d-lactate, i-lactate, d,l-lactate, d,l-malate, l-malate, mesylate, pamoate, phosphate, succinate, sulfate, bisulfate, d-tartrate, l-tartrate, d,l-tartrate, meso-tartrate, benzoate, gluceptate, d-glucuronate, hybenzate, isethionate, malonate, methylsulfate, 2-napsylate, nicotinate, nitrate, orotate, stearate, tosylate, thiocyanate, acefyllinate, aceturate, aminosalicylate, ascorbate, borate, butyrate, camphorate, camphocarbonate, decanoate, hexanoate, cholate, cypionate, dichloroacetate, edentate, ethyl sulfate, furate, fusidate, galactarate (mucate), galacturonate, gallate, gentisate, glutamate, glutarate, glycerophosphate, heptanoate (enanthate), hydroxybenzoate, hippurate, phenylpropionate, iodide, xinafoate, lactobionate, laurate, maleate, mandelate, methanesulfonate, myristate, napadisilate, oleate, oxalate, palmitate, picrate, pivalate, propionate, pyrophosphate, salicylate, salicylsulfate, sulfosalicylate, tannate, terephthalate, thiosalicylate, tribrophenate, valerate, valproate, adipate, 4-acetamidobenzoate, camsylate, octanoate, estolate, esylate, glycolate, thiocyanate, or undecylenate.

Without wishing to be limited to the following theory, it is believed that the prodrugs/conjugates of the present technology undergo enzyme hydrolysis of the ligand/linker-dextrorphan bond(s) in vivo, which subsequently leads to a cascade reaction resulting in rapid regeneration of dextrorphan and the respective oxoacid, polyethylene glycol, vitamin compound, or metabolites thereof and/or derivatives thereof. The oxoacids, polyethylene glycols, vitamin compounds, or derivatives thereof, of the present technology are non-toxic or have very low toxicity at the given dose levels and are preferably known drugs, natural products, metabolites, or GRAS (Generally Recognized As Safe) compounds (e.g., preservatives, dyes, flavors, etc.) or non-toxic mimetics or derivatives thereof.

General Structures

In some embodiments, the general structure of the conjugates of dextrorphan of the present technology can be represented by the following general Formula IA:

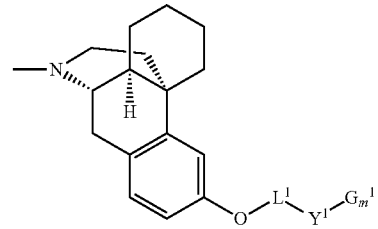

Formula IA where $L^1$ is absent, or

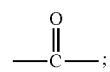

$Y^1$ is absent, or $[A-X-Z]_n$
where A, X, Z are independently absent or selected from
—O—, —S— or —$(CR^1R^2)_k$—
$R^1$, $R^2$ are independently selected from H, alkyl, aryl, alkylaryl, alkoxy, haloalkyl, or haloaryl
n and k are independently 1-4
$G_m^1$ is absent or selected independently for each repeating subunit from H, oxoacid, polyethylene glycol having from 2 to 5 ethylene oxide units, or a vitamin compound, and m is 1-4, except that m is 1 when $G^1$ is a hydrogen atom;
or a pharmaceutically acceptable salt thereof.

In some embodiments, $L^1$ and $Y^1$ are absent, $G^1$ is one or more oxoacids, and m is 1-3. Representative examples include, but are not limited to 3-Val-dextrorphan; 3-(N-acetyl-Val)-dextrorphan; 3-(ValValPhe)-dextrorphan; 3-(PhePhePhe)-dextrorphan; 3-(AlaAlaVal)-dextrorphan; 3-(GlyGlyAla)-dextrorphan; 3-hippuryl-dextrorphan; 3-(ProProPhe)-dextrorphan; 3-(GlyGly)-dextrorphan; 3-(ValGly)-dextrorphan; 3-(AlaPro)-dextrorphan; 3-cinnamoyl-dextrorphan; 3-(N,O-diacetyl-Tyr)-dextrorphan; and 3-(N-succinoyl-Val)-dextrorphan;

In some embodiments, $L^1$ is present, A and Z are 0, X is —$(CR^1R^2)_k$—, and $G^1$ is one or more oxoacids and m is 1-3. Representative examples include, but are not limited to, 3-(N-acetyl-Val-OCH$_2$OC(O))-dextrorphan; 3-(cinnamoyl-OCH$_2$OC(O))-dextrorphan; 3-(benzoyl-OCH$_2$OC(O))-dextrorphan; 3-(butanoyl-OCH$_2$OC(O))-dextrorphan; 3-(N,O-acetyl-Lys-OCH$_2$OC(O))-dextrorphan.

In some embodiments, $L^1$ and $Y^1$ are absent, and $G^1$ is a vitamin compound. Representative examples include, but are not limited to, 3-biotinyl-dextrorphan.

In some embodiments, $L^1$ is present, A is O, X and Z are absent, and $G^1$ is a vitamin compound. Representative examples include, but are not limited to, 3-(ascorbyl-C(O))-dextrorphan.

In some embodiments, $L^1$ is present, $Y^1$ is absent, m is 2 and $G_m^1$ can be represented as $G^{1a}$ and $G^{1b}$ where $G^{1a}$ is a hydroxycarboxylic acid, and $G^{1b}$ is a vitamin compound. Representative examples include, but are not limited to 3-(biotinyl-glycoloyl)-dextrorphan.

In some embodiments, $L^1$ is absent, $Y^1$ is absent, m is 2 and $G_m^1$ can be represented as $G^{1a}$ and $G^{1b}$ where $G^{1a}$ is a dicarboxylic acid, and $G^{1b}$ is a vitamin compound. Representative examples include, but are not limited to 3-(thiaminyl-succinoyl)-dextrorphan.

In some embodiments, $L^1$ is present, A is —$CR^1R^2$—, X is absent, Z is —$CR^1R^2$— or absent, and $G^1$ is polyethylene glycol. Representative examples include but are not limited to 3-(N₃-PEG₄-CH₂CH₂C(O))-dextrorphan and 3-(H₂N-PEG₅-CH₂CH₂C(O))-dextrorphan.

In some embodiments, L¹ is present, A is oxygen, X and Z are —(CR¹R²)ₖ— and G¹ is a hydrogen atom. Representative examples include, but are not limited to, 3-(ethoxy-C(O))-dextrorphan.

In some embodiments, L¹ is present, A is —(CR¹R²)ₖ—, X is oxygen (O), Z is absent, and G¹ is acetic acid. Representative examples include but are not limited to 3-(acetyl-OCH₂C(O))-dextrorphan and 3-(acetyl-OCH(phenyl)C(O))-dextrorphan.

In some embodiments, the general structure of the conjugates of dextrorphan of the present technology can be represented by the following general Formula IB:

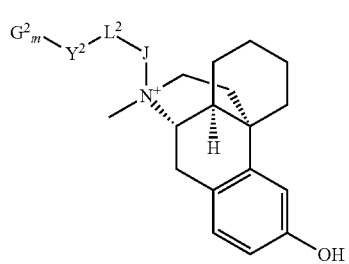

Formula IB where L² is absent, or is

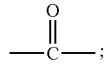

Y² is absent, or [A-X—Z]ₙ
where A, X, Z are independently absent or selected from —O—, —S— or —(CR¹R²)ₖ—
J is [M-W]ₚ
where M is absent, or —(CR³R⁴)_q—; and W is absent, or —O— or —S—
R¹, R², R³, R⁴ are each independently selected from H, alkyl, aryl, alkylaryl, alkoxy, haloalkyl, or haloaryl
n and k are independently 1-4
p and q are independently 1-4
$G_m^2$ is absent or selected independently for each repeating subunit from H, oxoacid, polyethylene glycol having from 1 to 5 ethylene oxide units, or a vitamin compound, and m is 1-4, except that m is 1 when G² is a hydrogen atom;
or a pharmaceutically acceptable salt thereof.

In some embodiments, M is —(CR³R⁴)_q—, W, L² and Y² are absent, G² is an oxoacid, and m is 1-3. Representative examples include, but are not limited to N-(acetyl-OCH₂)-dextrorphanium; N-(pivaloyl-OCH₂)-dextrorphanium; N-(Ser-Ile-CH₂)-dextrorphanium; N-(Val-CH₂)-dextrorphanium; and N-(Phe-Val-CH₂)-dextrorphanium.

In some embodiments, M is —(CR³R⁴)_q—, W is —O—, L² is present, A is —CR¹R²—, X is absent, Z is absent or —CR¹R²—, G² is polyethylene glycol. Representative examples include but are not limited to N-(MeO-PEG₃-CH₂C(O)OCH₂)-dextrorphanium and N—(HO-PEG₄-CH₂CH₂C(O)OCH₂)-dextrorphanium.

In some embodiments, M is —(CR³R⁴)_q—, W is —O—, L² is present, A and Z are —O—, X is —(CR¹R²)ₖ—, G² is an oxoacid, and m is 1-3. Representative examples include but are not limited to N—(BzO-CH₂OC(O)OCH₂)-dextrorphanium; N-(Ala-CH₂OC(O)OCH₂)-dextrorphanium; and N-(Pro-Val-CH₂OC(O)OCH₂)-dextrorphanium.

In some embodiments, M is —(CR³R⁴)_q—, W is —O—, L² is present, A is —O—, X and Z are absent, G² is a vitamin compound, and m is 1-3.

In some embodiments, the general structure of the conjugates of dextrorphan of the present technology can be represented by the following general Formula IC:

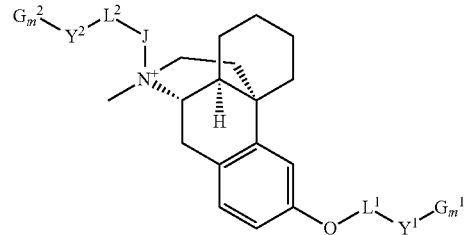

Formula IC where L¹ and L² are independently absent, or

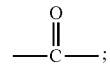

Y¹ and Y² are independently either absent, or [A-X—Z]ₙ
where A, X, Z are independently selected for Y¹ and Y², and are, independent of each other, either absent or selected from the group of —O—, —S—, or —(CR¹R²)ₖ—
J is [M-W]ₚ
where M is absent, or —(CR³R⁴)_q—; and W is absent, or —O— or —S—
R¹ and R² are each independently selected for Y¹ and Y², and are, independent of each other, selected from H, alkyl, aryl, alkylaryl, alkoxy, haloalkyl, or haloaryl
R³ and R⁴ are each independently selected from H, alkyl, aryl, alkylaryl, alkoxy, haloalkyl, or haloaryl
for each Y¹ and Y², n is independently an integer of 1-4
for each repeating unit of [A-X—Z]ₙ, when (CR¹R²)ₖ is present, k is independently an integer of 1-4.
p and q are independently 1-4
$G_m^1$ and $G_m^2$ are independently absent, or selected independently of each other and, when present, each repeating subunit is independently selected from H, oxoacid, polyethylene glycol having from 2 to 5 ethylene oxide units, or a vitamin compound;
where m is selected independently for G¹ and G², and is an integer of 1-4, except that m is 1 when G¹ or G² is a hydrogen atom;
or a pharmaceutically acceptable salt thereof.

In some embodiments, L¹ and Y¹ are absent, G¹ is one or more oxoacids, and m is 1-3, and M is —(CR³R⁴)_q—; W is O or absent, L² and Y² are absent, G² is one or more oxoacids, and m is 1-3. Representative examples include 3-(pivaloyl)-N-(pivaloyl-OCH₂)-dextrorphanium; 3-(Ac-Val)-N-(Phe-Phe-CH₂)-dextrorphanium; 3-(Ser-Ile)-N-(Val-CH₂)-dextrorphanium; 3-Val-N-(Val-CH₂)-dextrorphanium; 3-acetyl-N-(acetyl-OCH₂)-dextrorphanium.

In some embodiments, L¹ and Y¹ are present, A is O, X is —(CR¹R²)ₖ—, Z is O, G¹ is one or more oxoacids, and m is 1-3, and M is —(CR³R⁴)_q—; W is O or absent, L² and Y² are absent, $G^2$ is one or more oxoacids, and m is 1-3. Representative examples include 3-(acetylsalicyloyl-OCH$_2$OC(O))—N—(Ac-Val-CH$_2$)-dextrorphanium.

In some embodiments, $L^1$ is present, $Y^1$ is present, where A is O, X and Z are —(CR$^1$R$^2$)$_k$—, and $G^1$ is H, and M is —(CR$^3$R$^4$)$_q$—, W is O, $L^2$ and $Y^2$ are present, where A is O, X and Z are —(CR$^1$R$^2$)$_k$—, and $G^2$ is H. Representative examples include 3-(ethoxy-C(O))—N-(ethoxy-C(O)CH(CH$_3$))-dextrorphanium.

Oxoacids

Organic oxoacids (i.e., oxyacids, oxo acids, oxy-acids, oxiacids, oxacids) of the present technology are a class of compounds which contain oxygen, at least one other element, and at least one hydrogen bound to oxygen, and which produce a conjugate base by loss of positive hydrogen ion(s) (protons). Organic acids include carboxylic acids. Carboxylic acids are widespread in nature (naturally occurring), but carboxylic acids can also be non-natural (synthetic). Carboxylic acids can be categorized into numerous classes based on their molecular structure or formula, and many of the different classes may overlap.

Without wishing to limit the scope to one classification, the carboxylic acids of the present technology can be grouped into the following categories: aryl carboxylic acids, aliphatic carboxylic acids, dicarboxylic, polycarboxylic acids, and amino acids.

Some embodiments of the present technology provide oxoacids conjugated to dextrorphan, where the carboxylic acid group is directly attached to an aryl moiety. Carboxylic acids directly attached to the aryl moiety include benzoates and heteroaryl carboxylic acids. Benzoates are common in nature and include, for example but are not limited to, aminobenzoates (e.g., anthranilic acid analogs such as fenamates), aminohydroxybenzoates and hydroxybenzoates (e.g., salicylic acid analogs).

The general structure of benzoic acid and benzoic acid derivatives of the present technology can be represented by the following Formula II:

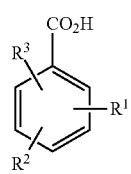

Formula II

In this Formula II, $R^1$, $R^2$, $R^3$ are independently selected from the group consisting of H, hydroxyl, amino, amine, amide, thiol, cyano, nitro, halogen, imine, alkyl, alkoxy, aryl, alkenyl, alkynyl, haloalkyl, alkylaryl, arylalkyl, heterocycle, arylalkoxy, cycloalkyl, cycloalkenyl, cycloalkynyl, carbonyl, thioether, selenoether, silyl, silyloxy, sulfonyl, and phosphonate.

Suitable hydroxyobenzoic acids can be found in FIG. 1 and include, but are not limited to, benzoic acid, salicylic acid, acetylsalicylic acid (aspirin), 3-hydroxybenzoic acid, 4-hydroxybenzoic acid, 6-methylsalicylic acid, o,m,p-cresotinic acid, anacardic acids, 4,5-dimethylsalicylic acid, o,m, p-thymotic acid, diflunisal, o,m,p-anisic acid, 2,3-dihydroxybenzoic acid (2,3-DHB), α,β,γ-resorcylic acid, protocatechuic acid, gentisic acid, piperonylic acid, 3-methoxysalicylic acid, 4-methoxysalicylic acid, 5-methoxysalicylic acid, 6-methoxysalicylic acid, 3-hydroxy-2-methoxybenzoic acid, 4-hydroxy-2-methoxybenzoic acid, 5-hydroxy-2-methoxybenzoic acid, vanillic acid, isovanillic acid, 5-hydroxy-3-methoxybenzoic acid, 2,3-dimethoxybenzoic acid, 2,4-dimethoxybenzoic acid, 2,5-dimethoxybenzoic acid, 2,6-dimethoxybenzoic acid, veratric acid (3,4-dimethoxybenzoic acid), 3,5-dimethoxybenzoic acid, gallic acid, 2,3,4-trihydroxybenzoic acid, 2,3,6-trihydroxybenzoic acid, 2,4,5-trihydroxybenzoic acid, 3-O-methylgallic acid (3-OMGA), 4-O-methylgallic acid (4-OMGA), 3,4-O-dimethylgallic acid, syringic acid, 3,4,5-trimethoxybenzoic acid.

Figure 2:
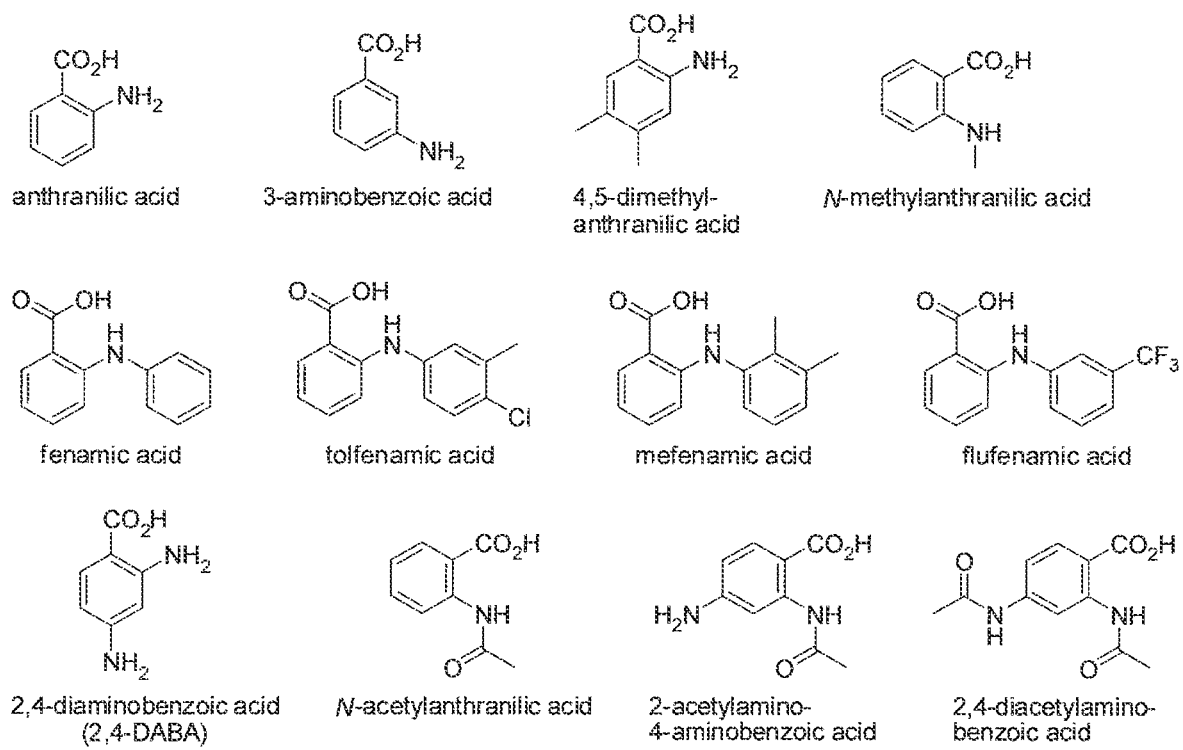
FIG. 2. Chemical structures of some aminobenzoic acids for use in the making of the conjugates of the present technology.

Suitable aminobenzoic acids are shown in FIG. 2 and include, but are not limited to, anthranilic acid, 3-aminobenzoic acid, 4,5-dimethylanthranilic acid, N-methylanthranilic acid, N-acetylanthranilic acid, fenamic acids (e.g., tolfenamic acid, mefenamic acid, flufenamic acid), 2,4-diaminobenzoic acid (2,4-DABA), 2-acetylamino-4-aminobenzoic acid, 4-acetylamino-2-aminobenzoic acid, 2,4-diacetylaminobenzoic acid.

Suitable aminohydroxybenzoic acids include, but are not limited to, 4-aminosalicylic acid, 3-hydroxyanthranilic acid, 3-methoxyanthranilic acid.

In some embodiments, the composition includes a benzoate conjugate comprising at least one dextrorphan conjugated to at least one benzoic acid or benzoic acid derivative, salt thereof or combination thereof.

In some embodiments, the benzoates include numerous benzoic acid analogs, benzoate derivatives with hydroxyl or amino groups or a combination of both. The hydroxyl and amino functions may be present in their free form or capped with another chemical moiety, preferably but not limited to methyl or acetyl groups. The phenyl ring may have additional substituents, but the total number of substituents can be four or less, three or less, or two or less.

In yet another embodiment, the present technology provides a prodrug or composition comprising at least one conjugate of dextrorphan and at least one heteroaryl carboxylic acid, a derivative thereof, or a combination thereof. The heteroaryl carboxylic acid can be selected from Formula III, Formula IV, Formula V, Formula VI, Formula VII, Formula VIII, Formula IX, Formula X, or Formula XI, where Formula III, Formula IV, Formula V, Formula VI, Formula VII, Formula VIII, Formula IX, Formula X, or Formula XI are:

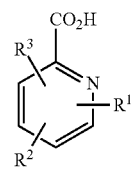

Formula III

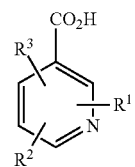

Formula IV

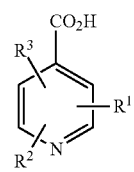

Formula V

Formula VI
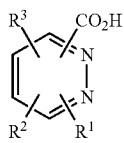

Formula VII
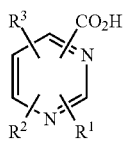

Formula VIII
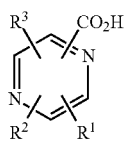

Formula IX
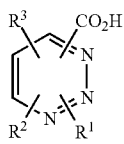

Formula X
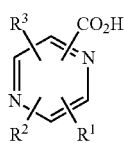

Formula XI
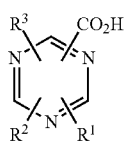

Figure 3:
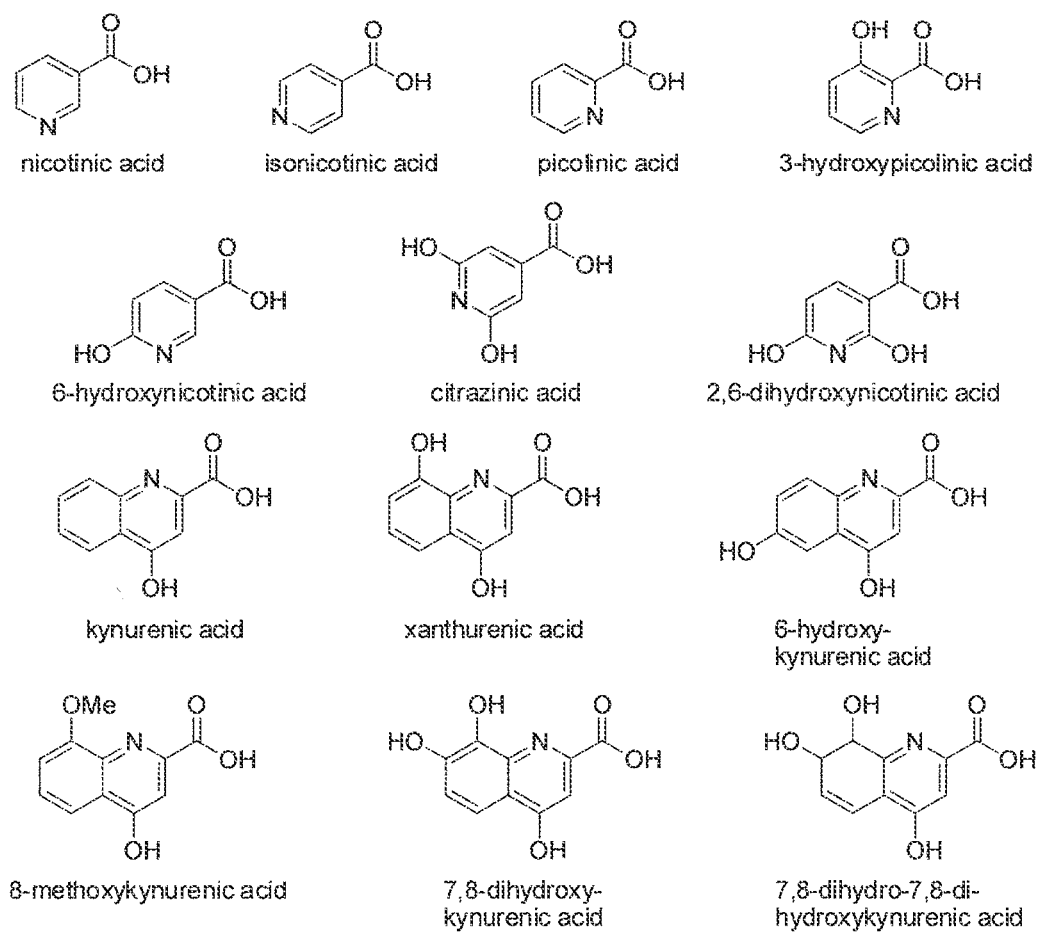
FIG. 3. Chemical structures of some heteroaryl carboxylic acids for use in the making of the conjugates of the present technology.

For these Formulas III, IV, V, VI, VII, VIII, IX, X, and XI, $R^1$, $R^2$, $R^3$ are independently selected from the group consisting of H, hydroxyl, amino, amine, amide, thiol, cyano, nitro, halogen, imine, alkyl, alkoxy, aryl, alkenyl, alkynyl, haloalkyl, alkylaryl, arylalkyl, heterocycle, arylalkoxy, cycloalkyl, cycloalkenyl, cycloalkynyl, carbonyl, thioether, selenoether, silyl, silyloxy, sulfonyl, and phosphonate. Some structures of suitable heteroaryl carboxylic acids for use in the present technology are found in FIG. 3.

In some embodiments, the carboxy group of the aryl carboxylic acids can be attached directly to the aromatic ring. The present technology includes both carbon-only aryl groups and aryl groups with heteroatoms (heteroaryl). The aryl or heteroaryl group which is connected directly to the carboxyl function can be a 6-membered ring and contains no or one heteroatom. In some embodiments, the additional substituted or unsubstituted aromatic or aliphatic rings can be fused to this 6-membered aryl or heteroaryl moiety. In some embodiments, the aryl carboxylic acids may have only one free carboxylic acid group and the total number of phenyl substituents on the 6-membered ring should be four or less, for example, 4, 3, 2 or 1.

Phenylacetates

Figure 4:
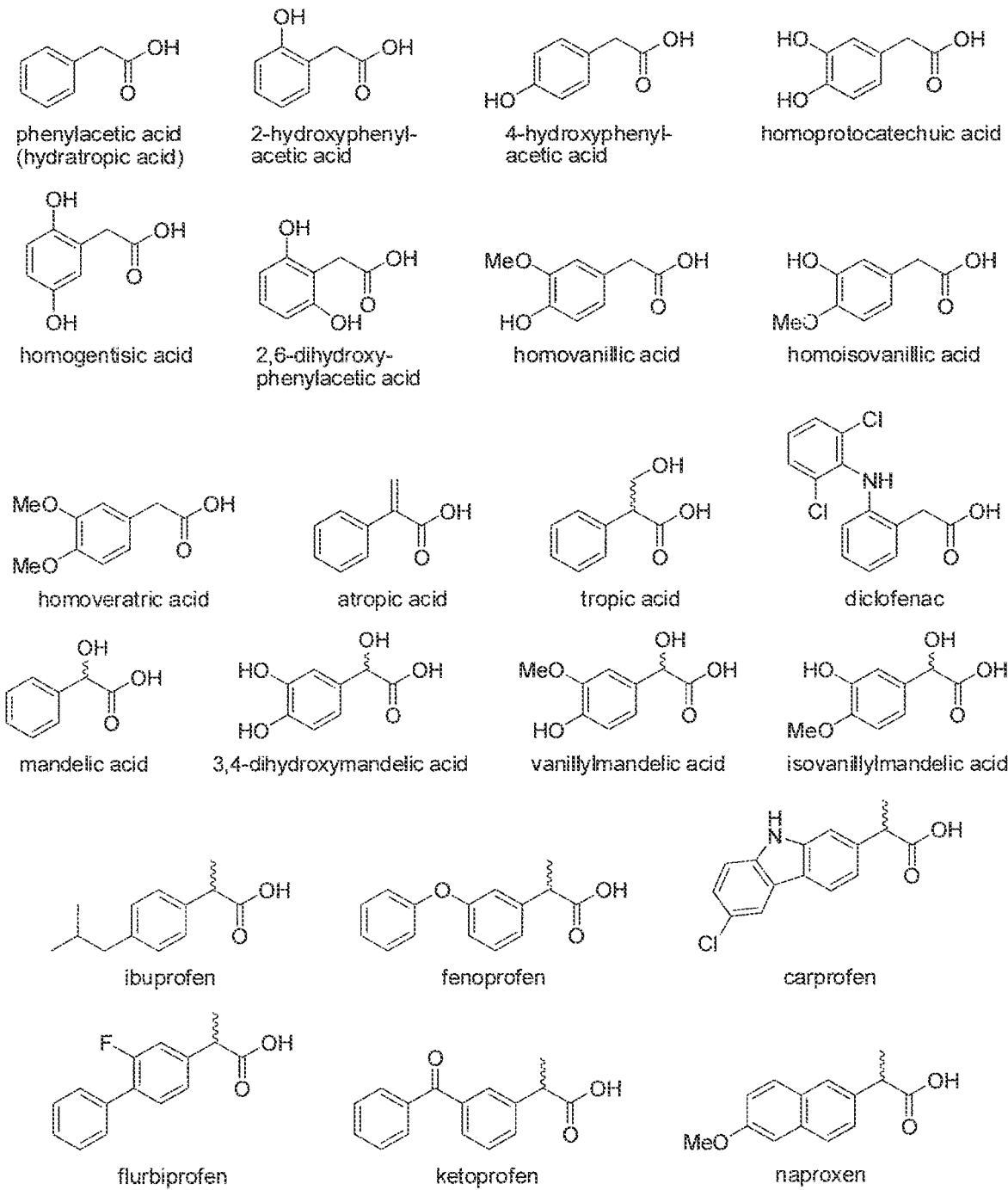
FIG. 4. Chemical structures of some phenylacetates for use in the making of the conjugates of the present technology.

In some embodiments of the present technology, the aryl carboxylic acids of the present technology comprise a carboxylic group that is separated by one carbon from the aryl moiety. These aryl carboxylic acids include branched phenylpropionic acids (i.e., 2-methyl-2-phenylacetates) or other derivatives of phenylacetate (FIG. 4). The general structure of at least one phenylacetate of the present technology is represented by the following general Formula XII:

Formula XII
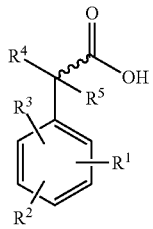

For this Formula XII, $R^1$, $R^2$, $R^3$, $R^4$, $R^5$ are independently selected from the group consisting of H, hydroxyl, amino, amine, amide, thiol, cyano, nitro, halogen, imine, alkyl, alkoxy, aryl, alkenyl, alkynyl, haloalkyl, alkylaryl, arylalkyl, heterocycle, arylalkoxy, cycloalkyl, cycloalkenyl, cycloalkynyl, carbonyl, thioether, selenoether, silyl, silyloxy, sulfonyl, and phosphonate.

Phenylacetic acids encompass various subsets of natural products, metabolites and pharmaceuticals. One such pharmaceutically important subset is "profens", a type of NSAIDs and derivatives of certain phenylpropionic acids (e.g., 2-methyl-2-phenylacetic acid analogs). Some other phenylacetates have central functions in the phenylalanine and tyrosine metabolism.

Some examples of phenylacetates of the present technology include, but are not limited to, phenylacetic acid (hydratropic acid), 2-hydroxyphenylacetic acid, 3-hydroxyphenylacetic acid, 4-hydroxyphenylacetic acid, homoprotocatechuic acid, homogentisic acid, 2,6-dihydroxyphenylacetic acid, homovanillic acid, homoisovanillic acid, homoveratric acid, atropic acid, d,l-tropic acid, diclofenac, d,l-mandelic acid, 3,4-dihydroxy-d,l-mandelic acid, vanillyl-d,l-mandelic acid, isovanillyl-d,l-mandelic acid, ibuprofen, fenoprofen, carprofen, flurbiprofen, ketoprofen, and naproxen. Some structures of suitable phenylacetates for use in the present technology are found in FIG. 4.

Benzylacetates

Figure 6:
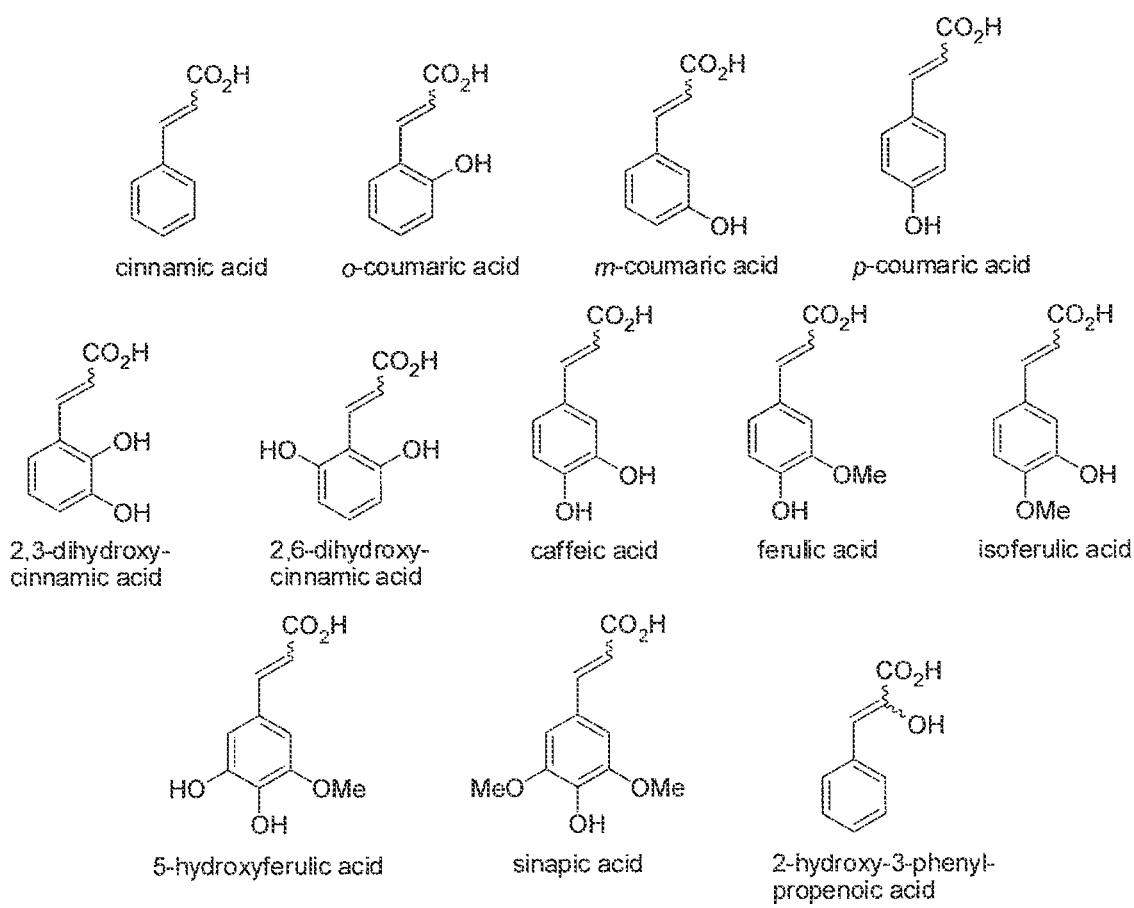
FIG. 6. Chemical structures of some cinnamates for use in the making of the conjugates of the present technology.

In additional embodiments, the aryl carboxylic acids of the present technology comprise a carboxylic group that is separated by two carbons from the aryl moiety. These aryl carboxylic acids include benzylacetates (FIG. 5) and substituted derivatives thereof and analogs of cinnamic acid (FIG. 6). Both classes of compounds are abundant in nature in the form of natural products or metabolites (e.g., phenylalanine metabolism). The general structures of some benzylacetates and cinnamates of the present technology are represented by the following general Formulas XIII and XIV:

Formula XIII
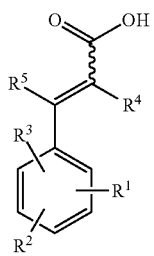

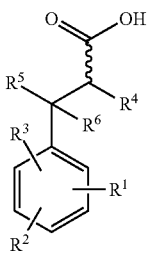

Formula XIV

For these Formulas XIII and XIV, $R^1$, $R^2$, $R^3$, $R^4$, $R^5$, $R^6$ are independently selected from the group consisting of H, hydroxyl, amino, amine, amide, thiol, cyano, nitro, halogen, imine, alkyl, alkoxy, aryl, alkenyl, alkynyl, haloalkyl, alkylaryl, arylalkyl, heterocycle, arylalkoxy, cycloalkyl, cycloalkenyl, cycloalkynyl, carbonyl, thioether, selenoether, silyl, silyloxy, sulfonyl, and phosphonate.

Benzylacetic acids are defined by an ethylene group between the carboxyl function and the phenyl ring. Both the alkyl chain and the aryl moiety can have substituents, preferably hydroxyl groups. Some compounds of this class can be found in the phenylalanine metabolism.

Some examples of benzylacetates of the present technology include, but are not limited to, benzylacetic acid, melilotic acid, 3-hydroxyphenylpropanoic acid, 4-hydroxyphenylpropanoic acid, 2,3-dihydroxyphenylpropanoic acid, d,l-phenyllactic acid, o,m,p-hydroxy-d,l-phenyllactic acid, or phenylpyruvic acid.

Cinnamates

Cinnamic acids (3-phenylacrylic acids) (FIG. 6) are unsaturated analogs of benzylacetic acids. Cinnamates occur in two isomeric forms: cis (Z) and trans (E). The cinnamate isomers of certain embodiments of the present technology are preferably, but not limited to, the trans configuration. Similar to benzylacetates, derivatives of cinnamic acid can be substituted on the alkenyl or aryl moiety of the molecule. Preferred substituents of some embodiments of the present technology are hydroxyl and methoxy groups. Certain cinnamates are thought to play a key role in phenylalanine metabolism.

Some examples of cinnamates of the present technology include, but are not limited to, cinnamic acid, o,m,p-coumaric acid, 2,3-dihydroxycinnamic acid, 2,6-dihydroxycinnamic acid, caffeic acid, ferulic acid, isoferulic acid, 5-hydroxyferulic acid, sinapic acid, or 2-hydroxy-3-phenylpropenoic acid.

Suitable aliphatic carboxylic acids for use in the present technology include, but are not limited to, for example, saturated, monounsaturated, polyunsaturated, acetylenic, substituted (e.g., alkyl, hydroxyl, methoxy, halogenated, etc.), heteroatom containing or ring containing carboxylic acids. Suitable examples of saturated carboxylic acids include, but are not limited to, for example, methanoic, ethanoic, propanoic, butanoic, pentanoic, hexanoic, heptanoic, octanoic, 2-propylpentanoic acid, nonanoic, decanoic, dodecanoic, tetradecanoic, hexadecanoic, heptadecanoic, octadecanoic, or eicosanoic acid. Suitable monounsaturated carboxylic acids for practice of the present technology include, but are not limited to, for example, 4-decenoic, 9-decenoic, 5-lauroleic, 4-dodecenoic, 9-tetradecenoic, 5-tetradecenoic, 4-tetradecenoic, 9-hexadecenoic, 6-hexadecenoic, 6-octadecenoic, or 9-octadecenoic acid.

Suitable polyunsaturated carboxylic acids for use in the present technology include, but are not limited to, for example, sorbic, octadecadienoic, octadecatrienoic, octadecatetraenoic, eicosatrienoic, eicosatetraenoic, eicosapentaenoic, docosapentaenoic, or docosahexaenoic acids. Suitable acetylenic carboxylic acids for use in the present technology include, but are not limited to octadecynoic, octadecenynoic, 6,9-octadecenynoic, heptadecenynoic, tridecatetraenediynoic, tridecadienetriynoic, octadecadienediynoic, heptadecadienediynoic, octadecadienediynoic, octadecenediynoic, or octadecenetriynoic acids.

Suitable substituted carboxylic acids for practice of the present technology include, but are not limited to, for example, methylpropanoic, isovaleric, methylhexadecanoic, 8-methyl-6-nonenoic, methyloctadecanoic, trimethyloctacosanoic, trimethyltetracosenoic, heptamethyltriacontanoic, tetramethylhexadecanoic, tetramethylpentadecanoic, lactic, glyceric, glycolic, threonic, 3-hydroxypropionic, hydroxyoctadecatrienoic, hydroxyoctadecenoic, hydroxytetracosanoic, 2-hydroxybutyric, 3-hydroxybutyric, 4-hydroxybutyric, 4-hydroxypentanoic, hydroxyoctadecadienediynoic, hydroxyoctadecadienoic, 10-hydroxydecanoic, hydroxydecenoic, hydroxyeicosenoic, hydroxyeicosadienoic, hydroxyhexadecanoic, dihydroxytetracosenoic, dihydroxydocosanoic, hydroxydocosanoic, trihydroxyoctadecanoic, trihydroxyhexadecanoic, trihydroxyicosahexaenoic, trihydroxyicosapentaenoic, 2-methoxy-5-hexadecenoic, 2-methoxy hexadecanoic, 7-methoxy-4-tetradecenoic, 9-methoxypentadecanoic, 11-methoxyheptadecanoic, 3-methoxydocosanoic, diacetoxydocosanoic, 2-acetoxydocosanoic, 2-acetoxytetracosanoic, 2-acetoxyhexacosanoic, 9-oxononanoic, oxodecanoic, oxododecenoic, hydroxyoxodecenoic, 10-oxo-8-decenoic, fluorooctadecenoic, fluorodecanoic, fluorotetradecanoic, fluorohexadecanoic, fluorooctadecadienoic, chlorohydroxyhexadecanoic, chlorohydroxyoctadecanoic, dichlorooctadecanoic, 3-bromo-2-nonaenoic, 9,10-dibromooctadecanoic, 9,10,12,13-tetrabromooctadecanoic, 10-nitro-9,12-octadecadienoic, 12-nitro-9,12-octadecadienoic, 9-nitro-9-octadecenoic, 9-oxo-2-decenoic, 9-oxo-13-octadecenoic, oxooctadecatrienoic, 15-oxo-18-tetracosenoic, 17-oxo-20-hexacosenoic, or 19-oxo-22-octacosenoic acids.

Suitable examples of heteroatom containing carboxylic acids include, but are not limited to, for example, 9-(1,3-nonadienoxy)-8-nonenoic, 9-(1,3,6-nonatrienoxy)-8-nonenoic, 12-(1-hexenoxy)-9,11-dodecadienoic, 12-(1,3-hexadienoxy)-9,11-dodecadienoic, 2-dodecylsulfanylacetic, 2-tetradecylsulfanylacetic, 3-tetradecylsulfanylprop-2-enoic, or 3-tetradecylsulfanylpropanoic acid. Suitable examples of ring containing carboxylic acids include, but are not limited to, for example, 10-(2-Hexylcyclopropyl) decanoic, 3-(2-[6-bromo-3,5-nondienylcyclopropyl)propanoic, 9-(2-hexadecylcyclopropylidene)non-5-enoic, 8-(2-octyl-1-cyclopropenyl)octanoic, 7-(2-octyl-1-cyclopropenyl)heptanoic, 9,10-epoxyoctadecanoic, 9,10-epoxy12-octadecenoic, 12,13-epoxy-9-octadecenoic, 14,15-epoxy-11-eicosenoic, 11-(2-cyclopenten-1-yl)undecanoic, 13-(2-cyclopenten-1-yl)tridecanoic, 13-(2-cyclopentenyl)-6-tridecenoic, 11-cyclohexylundecanoic, 13-cyclohexyltridecanoic, 7-(3,4-dimethyl-5-pentylfuran-2-yl)heptanoic, 9-(4-methyl-5-pentylfuran-2-yl)nonanoic, 4-[5]-ladderanebutanoic, 6-[5]-ladderane-hexanoic, or 6-[3]-ladderanehexanoic acid.

In some embodiments, the dextrorphan, derivatives thereof or combinations thereof, can be conjugated to one or more dicarboxylic acids or tricarboxylic acids. Dicarboxylic acids are compounds with two carboxyl groups with a general formula of HOOC—R—COOH, where R can be an alkyl, alkenyl, alkynyl or aryl group, or derivatives thereof.

Dicarboxylic acids can have straight carbon chains or branched carbon chains. The carbon chain length may be short or long. Polycarboxylic acids are carboxylic acids with three or more carboxyl groups. Suitable examples of dicarboxylic and tricarboxylic acids for the practice of the present technology include, but are not limited to, for example, oxalic, malonic, succinic, glutaric, adipic, pimelic, suberic, azelaic, sebacic, brassylic, thapsic, malic, tartaric, dihydroxymesoxalic, D-hydroxyglutaric, methylmalonic, meglutol, diaminopimelic, carbamoyl aspartic, fumaric, maleic, mesaconic, 3-methylglutaconic, traumatic, phthalic acid, isophthalic, terephthalic, dipicolinic, citric acid, isocitric, carballylic, or trimesic acid. Some structures of suitable dicarboxylic acids for use in the practice of the present technology can be found in FIG. 7, and some structures of suitable tricarboxylic acids for use in the practice of the present technology can be found in FIG. 8.

Amino Acids

Amino acids are one of the most important building blocks of life. They constitute the structural subunit of proteins, peptides, and many secondary metabolites. In addition to the 22 standard (proteinogenic) amino acids that make up the backbone of proteins, there are hundreds of other natural (non-standard) amino acids that have been discovered either in free form or as components in natural products. The amino acids used in some embodiments of the prodrugs of this invention include natural amino acids, synthetic (non-natural, unnatural) amino acids, and their derivatives.

Standard Amino Acids

Figure 9:
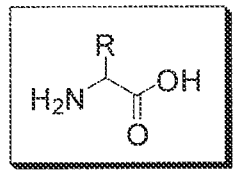
FIG. 9. Chemical structures of some standard amino acids for use in the making of the conjugates of the present technology.

There are currently 22 known standard or proteinogenic amino acids that make up the monomeric units of proteins and are encoded in the genetic code. The standard amino acids include alanine, arginine, asparagine, aspartic acid, cysteine, glutamic acid, glutamine, glycine, histidine, isoleucine, leucine, lysine, methionine, phenylalanine, proline, pyrrolysine, selenocysteine, serine, threonine, tryptophan, tyrosine and valine. These standard amino acids have the general structure shown in FIG. 9, where R represents the side chain on the α-carbon.

Non-Standard Amino Acids

Figure 10:
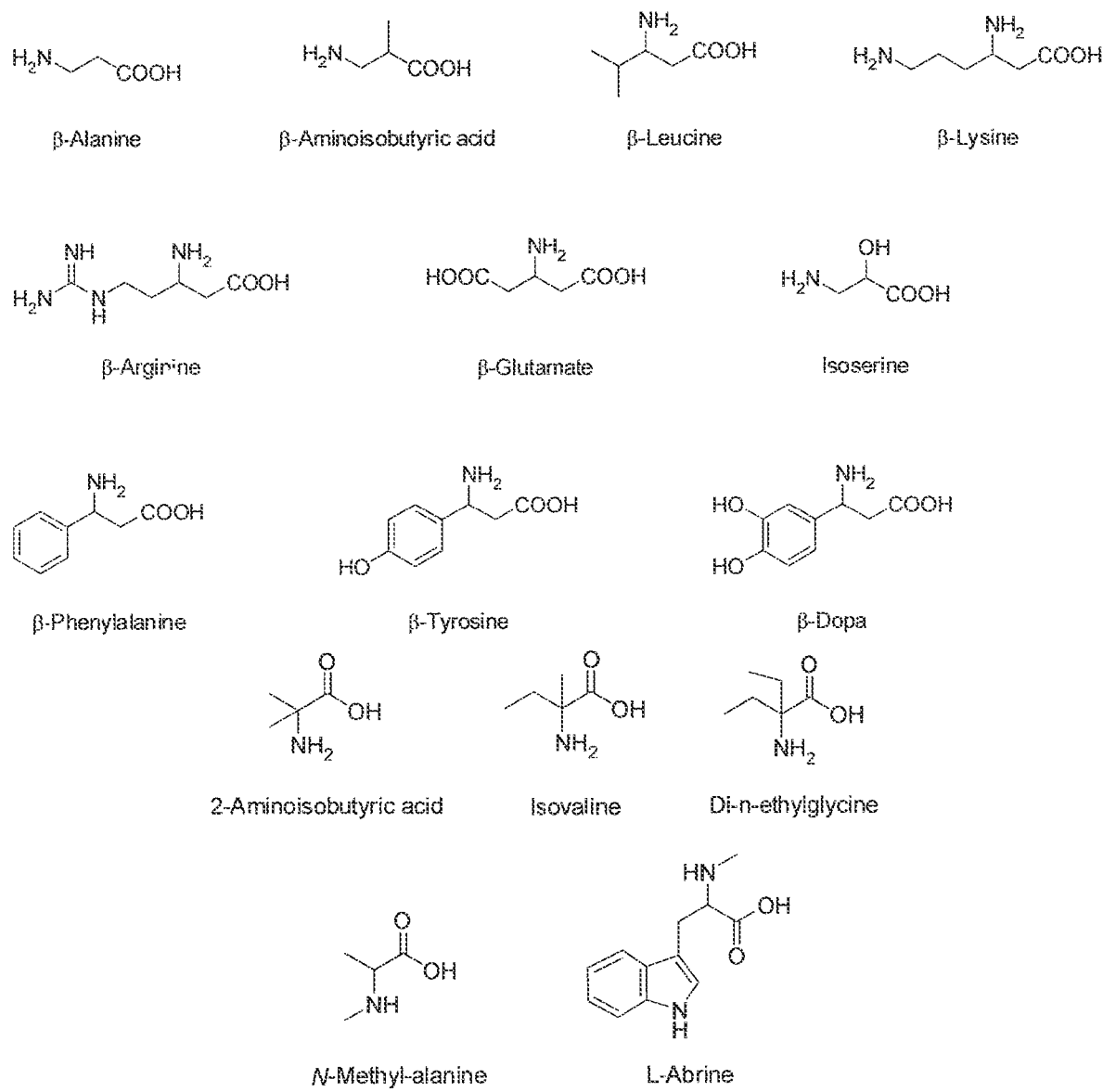
FIG. 10. Chemical structures of some non-standard amino acids for use in the making of the conjugates of the present technology.

Non-standard amino acids can be found in proteins created by chemical modifications of standard amino acids already incorporated in the proteins. This group also includes amino acids that are not found in proteins but are still present in living organisms either in their free form or bound to other molecular entities. Non-standard amino acids occur mostly as intermediates in metabolic pathways of standard amino acids and are not encoded by the genetic code. Examples of non-standard amino acids include but are not limited to ornithine, homoarginine, citrulline, homocitrulline, homoserine, theanine, γ-aminobutyric acid, 6-aminohexanoic acid, sarcosine, cartinine, 2-aminoadipic acid, pantothenic acid, taurine, hypotaurine, lanthionine, thiocysteine, cystathionine, homocysteine, β-amino acids such as β-alanine, β-aminoisobutyric acid, β-leucine, β-lysine, β-arginine, β-tyrosine, β-phenylalanine, isoserine, β-glutamic acid, β-tyrosine, β-dopa (3,4-dihydroxy-L-phenylalanine), α,α-disubstituted amino acids such as 2-aminoisobutyric acid, isovaline, di-n-ethylglycine, N-methyl acids such as N-methyl-alanine, L-abrine, hydroxy-amino acids such as 4-hydroxyproline, 5-hydroxylysine, 3-hydroxyleucine, 4-hydroxyisoleucine, 5-hydroxy-L-tryptophan, cyclic amino acids such as 1-aminocyclopropyl-1-carboxylic acid, azetidine-2-carboxylic acid and pipecolic acid. Some structures of suitable non-standard amino acids that can be used in some embodiments of the prodrugs of this invention are shown in FIG. 10.

Synthetic Amino Acids

Figure 11:
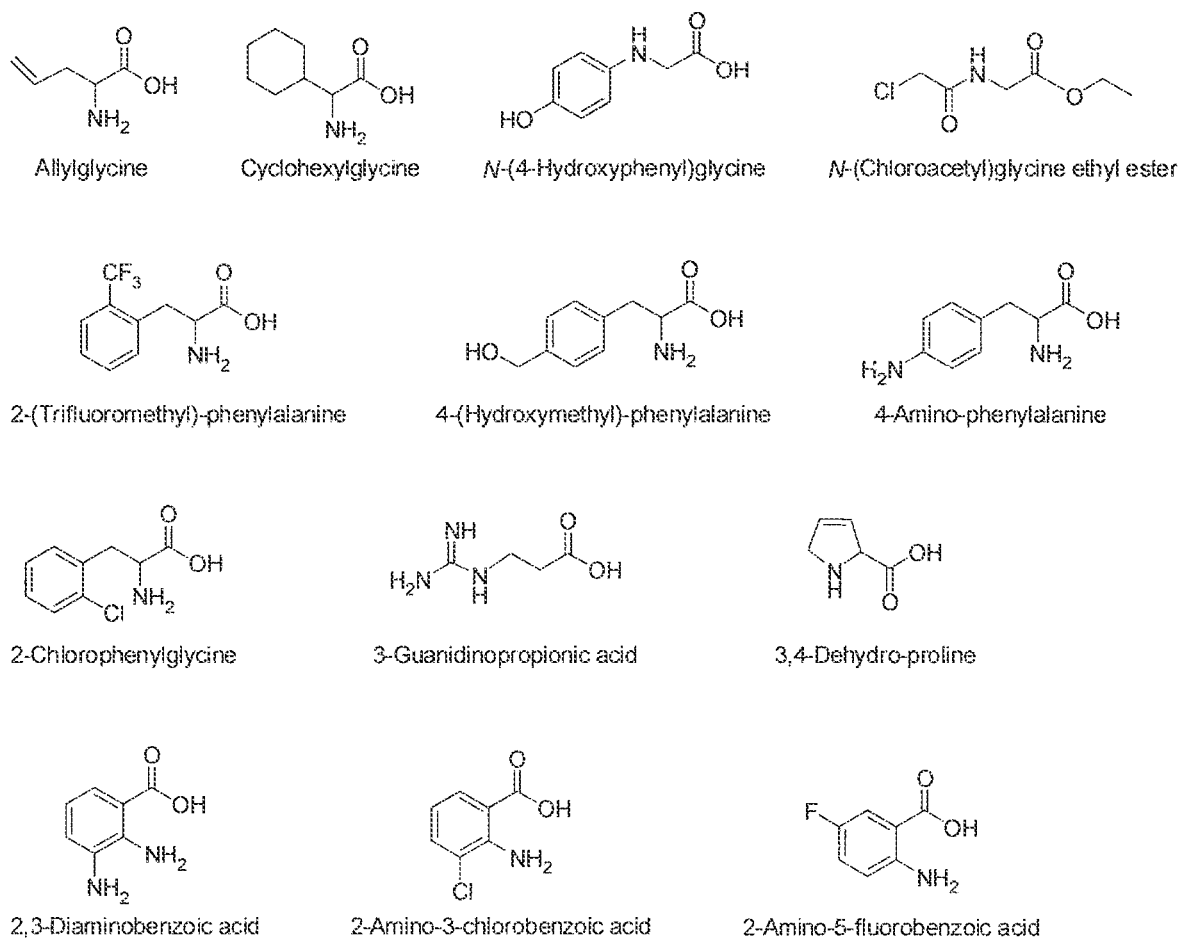
FIG. 11. Chemical structures of some synthetic amino acids for use in the making of the conjugates of the present technology.
Figure 13:
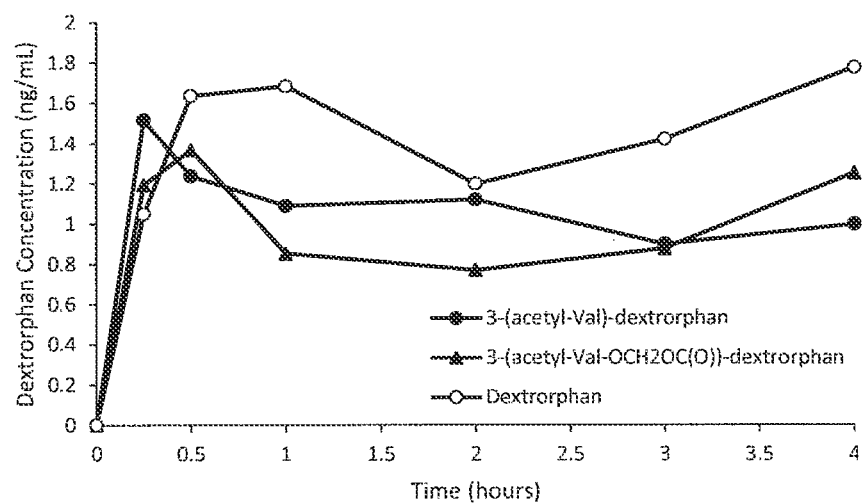
FIG. 13. Oral PK curves comparing 3-(N-acetyl-Val)-dextrorphan conjugate and 3-(N-acetyl-Val-OCH$_2$OC(O))-dextrorphan conjugate with unconjugated dextrorphan in rats.
Figure 14:
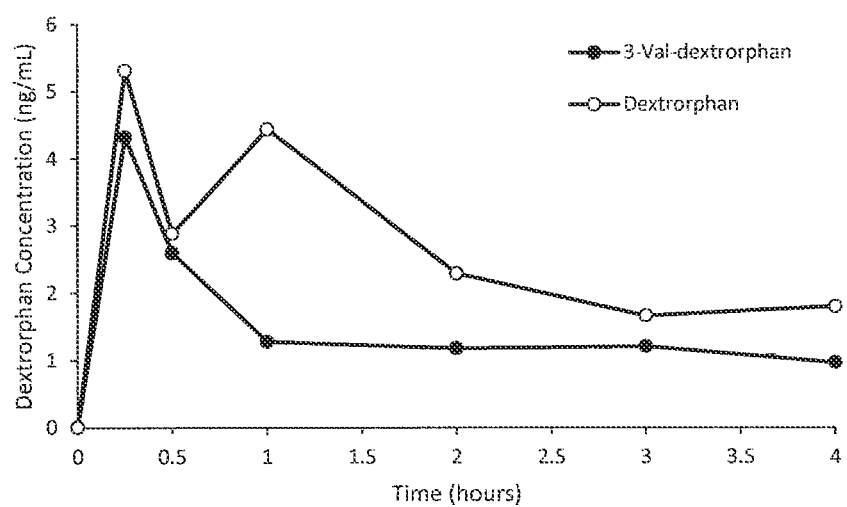
FIG. 14. Oral PK curves comparing 3-Val-dextrorphan conjugate with unconjugated dextrorphan in rats.
Figure 15:
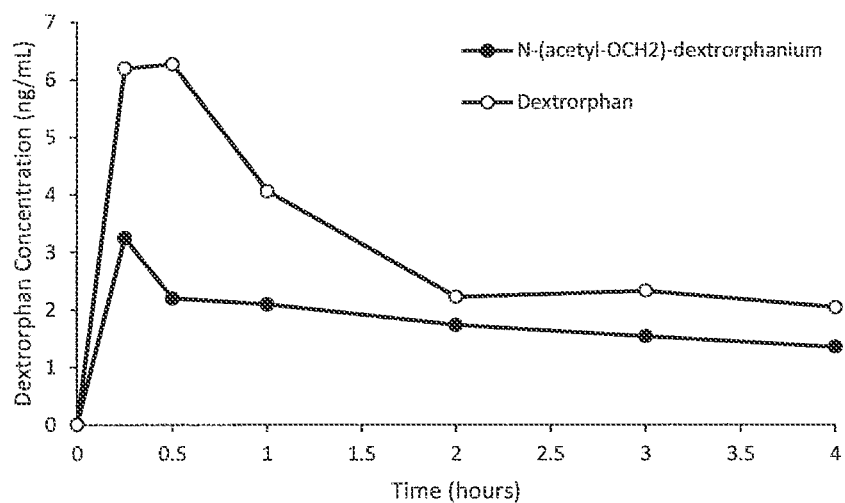
FIG. 15. Oral PK curves comparing N-(acetyl-OCH$_2$)-dextrorphanium conjugate with unconjugated dextrorphan in rats.
Figure 16:
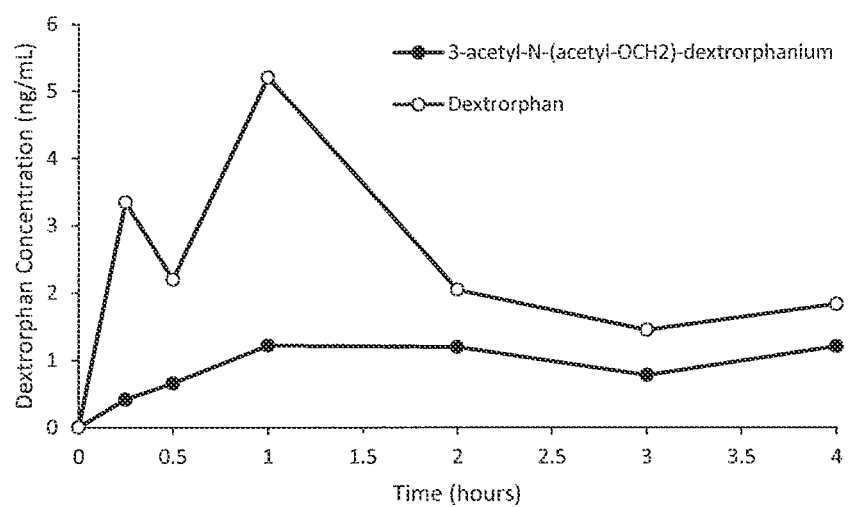
FIG. 16. Oral PK curves comparing 3-acetyl-N-(acetyl-OCH$_2$)-dextrorphanium conjugate with unconjugated dextrorphan in rats.

Synthetic amino acids do not occur in nature and are prepared synthetically. Examples include but are not limited to allylglycine, cyclohexylglycine, N-(4-hydroxyphenyl)glycine, N-(chloroacetyl)glycline ester, 2-(trifluoromethyl)-phenylalanine, 4-(hydroxymethyl)-phenylalanine, 4-aminophenylalanine, 2-chlorophenylglycine, 3-guanidino propionic acid, 3,4-dehydro-proline, 2,3-diaminobenzoic acid, 2-amino-3-chlorobenzoic acid, 2-amino-5-fluorobenzoic acid, allo-isoleucine, tert-leucine, 3-phenylserine, isoserine, 3-aminopentanoic acid, 2-amino-octanedioic acid, 4-chloro-β-phenylalanine, β-homoproline, β-homoalanine, 3-amino-3-(3-methoxyphenyl)propionic acid, N-isobutyryl-cysteine, 3-amino-tyrosine, 5-methyl-tryptophan, 2,3-diaminopropionic acid, 5-aminovaleric acid, and 4-(dimethylamino)cinnamic acid. Some structures of suitable synthetic amino acids that can be used in some embodiments of the prodrugs of this invention are shown in FIG. 11.

Polyethylene Glycols

In some embodiments of the present technology, dextrorphan, derivatives thereof or combinations thereof, is conjugated to a polyethylene glycol, or derivatives thereof. In some embodiments, the terminal hydroxyl group of the polyethylene glycol can be substituted with an amino, azide, or methoxy group. Some suitable structures of polyethylene glycols include the following:

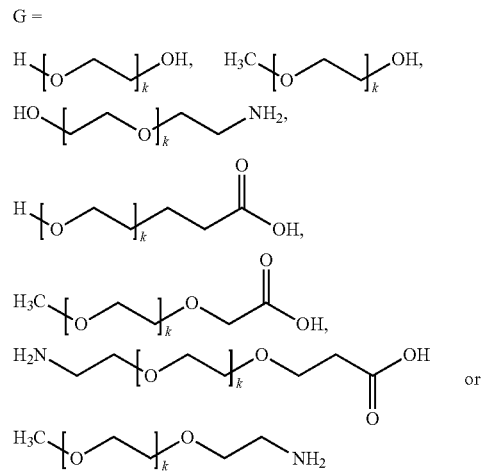

wherein k is 1-20 for these structures.

Vitamin Compounds

In some embodiments of the present technology, dextrorphan, derivatives thereof, or combinations thereof, is conjugated to one or more vitamin compounds. The vitamin compounds include both water soluble and fat soluble vitamins or derivatives thereof. Useful vitamin compounds are those that have one or more carboxylic acid groups, one or more hydroxyl groups, or one or more other reactive functional groups that can form a bond with dextrorphan either directly or through one or more linkers. Examples of water soluble vitamins that could be conjugated to dextrorphan include biotin, folate (folic acid), niacin, pantothenic acid, riboflavin, thiamin, pyridoxine, and ascorbic acid. Examples of fat soluble vitamins that could be conjugated to dextrorphan include Vitamin A (retinol), vitamin $D_2$ (ergocalciferol), vitamin D₃ (cholecalciferol), vitamin E (tocopherols and tocotrienols, including alpha, beta, gamma, and delta-tocopherol), and vitamin K (phylloquinone). Some structures of suitable water soluble vitamins and fat soluble vitamins for use in the present technology are found in FIGS. 12A and 12B, respectively.

Linkers

In some embodiments of the present technology, the dextrorphan, derivatives thereof, or combinations thereof, is conjugated to one or more organic oxoacids, polyethylene glycols, or vitamin compounds via one or more linkers. Linker moieties of the present technology, which connect the one or more organic oxoacids, polyethylene glycols, or vitamin compounds to the dextrorphan, derivatives thereof or combinations thereof, can have the following general formulas:

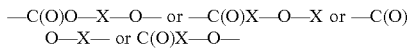

for conjugation at the C-3 hydroxyl position;

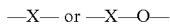

for conjugation at the N-17 tertiary amine position;
wherein for these linker formulas, X is selected from a representative group including alkyl, substituted alkyl, aryl, substituted aryl, arylalkyl, substituted alkylaryl, heteroalkyl, substituted heteroalkyl, heteroaryl, substituted heteroaryl, heterocycle, substituted heterocycle, alkenyl, substituted alkenyl, alkynyl, substituted alkynyl, cycloalkyl, substituted cycloalkyl, cycloalkenyl, substituted cycloalkenyl, cycloalkynyl, or substituted cycloalkynyl.

Preferred embodiments of the present technology include linkers where X is at least one aliphatic group. More preferred embodiments include linkers where X is at least one alkyl group.

Physiological Benefits

The above defined prodrugs or conjugates of dextrorphan can be given orally and, upon administration, release the active dextrorphan after being hydrolyzed in the body. Not to be bound by any particular theory, it is believed that since the oxoacids, polyethylene glycols, and vitamin compounds of this invention are naturally occurring metabolites or mimetics thereof or pharmaceutically active compounds, these prodrugs can be easily recognized by physiological systems resulting in hydrolysis and release of dextrorphan. The claimed prodrugs themselves are either not active or have limited pharmacological activity and consequently may follow a metabolic pathway that differs from the parent drug. By choosing suitable oxoacids, polyethylene glycols, and/or vitamin compounds ("ligands"), the release of dextrorphan into the systemic circulation can be controlled even when the prodrug is administered via routes other than oral. In one embodiment, the modified or conjugated dextrorphan would release dextrorphan similar to free or unmodified or unconjugated dextrorphan. In another embodiment, the modified or conjugated dextrorphan may have a more rapid release of dextrorphan compared to unmodified or unconjugated dextrorphan. In another embodiment, the modified dextrorphan would be released in a controlled or sustained manner. This controlled release can potentially alleviate certain side-effects and improve upon the safety profile of the parent drug. These side-effects may include, vomiting, drowsiness, nausea, dizziness, diarrhea, constipation, nervousness, restlessness, respiratory depression, hallucinations, double vision, hypotension, hypertension, blackouts, and skin rash. In addition, dextrorphan and other NMDA receptor antagonists are dissociative hallucinogens and are thus prone to substance abuse.

Recreational drug abuse of hallucinogens is a common problem. Depending on the drug routes of administration may include oral, intranasal ("snorting"), and intravenous ("shooting"). In some embodiments, dextrorphan that is conjugated with a suitable ligand does not result in rapid spikes in plasma concentration after oral administration that is sought by a potential drug abuser. In some embodiments, dextrorphan released from the conjugate may have a delayed $T_{max}$ and possibly lower $C_{max}$ than the parent drug. Not to be bound by any particular theory, it is believed that the conjugates of the present technology, when taken orally or by other non-oral routes, reduce, lessen, or do not provide the feeling of a "rush" even when taken orally at higher doses, but still maintain therapeutic relief. In another embodiment, dextrorphan conjugated with appropriate ligands of this invention is not hydrolyzed efficiently when administered via non-oral routes. As a result, in some embodiments, the prodrugs of the present technology do not generate as high plasma or blood concentrations of released dextrorphan when injected or snorted compared to free dextrorphan administered through these routes.

In some embodiments, the conjugates of the present technology, since they comprise ligands covalently bound to dextrorphan, are not able to be physically manipulated to release the dextrorphan from the conjugated dextrorphan by methods, for example, of grinding up or crushing of solid forms.

In some embodiments, the at least one prodrug or conjugate of the present technology can be formulated into dosage forms that include but are not limited to tablet, capsule, caplet, troche, lozenge, powder, suspension, syrup, solution, oral thin film (OTF), oral strips, inhalation compounds or suppositories. In some embodiments, the dosage forms are administered orally. Preferred oral administration forms are solutions, syrups, suspensions, capsules, tablets and OTF. Suitable dosing vehicles of the present technology include, but are not limited to, water, phosphate buffered saline (PBS), Tween in water, and PEG in water.

Solid dosage forms can optionally include one or more of the following types of excipients: antiadherents, binders, coatings, disintegrants, gel-forming agents, fillers, flavors and colors, glidants, lubricants, preservatives, sorbents and sweeteners, among others.

Oral formulations of the present technology can also be included in a solution, a suspension or a slurry, in an aqueous liquid or a non-aqueous liquid. The formulation can be an emulsion, such as an oil-in-water liquid emulsion or a water-in-oil liquid emulsion. The oils can be administered by adding the purified and sterilized liquids to a prepared enteral formula, which is then placed in the feeding tube of a patient who is unable to swallow.

Soft gel or soft gelatin capsules may be prepared, for example by dispersing the formulation in an appropriate vehicle (vegetable oils are commonly used) to form a high viscosity mixture. This mixture is then encapsulated with a gelatin based film using technology and machinery known to those in the soft gel industry. The individual units so formed are then dried to constant weight.

Chewable tablets, for example, may be prepared by mixing the formulations with excipients designed to form a relatively soft, flavored, tablet dosage form that is intended to be chewed rather than swallowed. Conventional tablet machinery and procedures, for example, direct compression and granulation, i.e., or slugging, before compression, can be utilized. Those individuals involved in pharmaceutical solid dosage form production are versed in the processes and the machinery used, as the chewable dosage form is a very common dosage form in the pharmaceutical industry.

Film coated tablets, for example may be prepared by coating tablets using techniques such as rotating pan coating methods or air suspension methods to deposit a contiguous film layer on a tablet.

Compressed tablets, for example may be prepared by mixing the formulation with one or more excipients intended to add binding qualities to disintegration qualities. The mixture is either directly compressed, or granulated and then compressed using methods and machinery known to those in the industry. The resultant compressed tablet dosage units are then packaged according to market need, for example, in unit dose, rolls, bulk bottles, blister packs, etc.

The present technology contemplates that the conjugates of the present technology can be formulated into formulations or co-formulations that may further comprise one or more additional components. For example, such formulations can include biologically-acceptable carriers which may be prepared from a wide range of materials. Without being limited to, such materials include diluents, binders and adhesives, lubricants, gel-forming agents, plasticizers, disintegrants, surfactants, colorants, bulking substances, flavorings, sweeteners and miscellaneous materials such as buffers and adsorbents in order to prepare a particular medicated formulation.

Binders may be selected from a wide range of materials such as hydroxypropylmethylcellulose, ethylcellulose, or other suitable cellulose derivatives, povidone, acrylic and methacrylic acid co-polymers, pharmaceutical glaze, gums, milk derivatives, such as whey, starches, and derivatives, as well as other conventional binders known to persons working in the art. Exemplary non-limiting solvents are water, ethanol, isopropyl alcohol, methylene chloride or mixtures and combinations thereof. Exemplary non-limiting bulking substances include sugar, lactose, gelatin, starch, and silicon dioxide.

It should be understood that in addition to the ingredients particularly mentioned above, the formulations of the present technology can include other suitable agents such as flavoring agents, preservatives and antioxidants. Such antioxidants would be food acceptable and could include vitamin E, carotene, BHT or other antioxidants.

Other compounds which may be included by admixture are, for example, medically inert ingredients, e.g., solid and liquid diluents, such as lactose, dextrose, saccharose, cellulose, starch or calcium phosphate for tablets or capsules, olive oil or ethyl oleate for soft capsules and water or vegetable oil for suspensions or emulsions; lubricating agents such as silica, talc, stearic acid, magnesium or calcium stearate and/or polyethylene glycols; gelling agents such as colloidal clays; thickening agents such as gum tragacanth or sodium alginate, binding agents such as starches, arabic gums, gelatin, methylcellulose, carboxymethylcellulose or polyvinylpyrrolidone; disintegrating agents such as starch, alginic acid, alginates or sodium starch glycolate; effervescing mixtures; dyestuff; sweeteners; wetting agents such as lecithin, polysorbates or laurylsulfates; and other therapeutically acceptable accessory ingredients, such as humectants, preservatives, buffers and antioxidants, which are known additives for such formulations.

For oral administration, fine powders or granules containing diluting, dispersing and/or surface-active agents may be presented in a draught, in water or a syrup, in capsules or sachets in the dry state, in a non-aqueous suspension wherein suspending agents may be included, or in a suspension in water or a syrup. Where desirable, flavoring, preserving, suspending, thickening or emulsifying agents can be included.

Liquid dispersions for oral administration may be syrups, emulsions or suspensions. The syrups may contain as carrier, for example, saccharose or saccharose with glycerol and/or mannitol and/or sorbitol. In particular, a syrup for diabetic patients can contain as carriers only products, for example sorbitol, which do not metabolize to glucose or which metabolize only a very small amount to glucose. The suspensions and the emulsions may contain a carrier, for example a natural gum, agar, sodium alginate, pectin, methylcellulose, carboxymethylcellulose or polyvinyl alcohol. The ingredients mentioned herein are not intended to be exhaustive, and one of skill in the art will be able to formulate compositions using known or to be known ingredients.

It is contemplated that the dextrorphan conjugates of the present technology can be combined with one or more active substances, such as different dextrorphan conjugates, unconjugated dextrorphan, or other active ingredient(s) depending on intended indication. Examples of active pharmaceuticals that can be combined with the conjugates of the present technology include, but are not limited to, acetaminophen, phenylpropanolamine, ibuprofen, aspirin, diflusinal, salicylic acid, dexibuprofen, naproxen, fenoprofen, ketoprofen, dexketoprofen, flurbiprofen, oxaprozin, loxoprofen, indomethacin, tolmetin, sulindac, etodolac, ketorolac, diclofenac, piroxicam, meloxicam, tenoxicam, lornoxicam, isoxicam, mefenamic acid, meclofenamic acid, flufenamic acid, tolfenamic acid, celecoxib, valdecoxib, lumiracoxib, pheniramine, chlorpheniramine, fexofenadine, azelastine, hydroxyzine, diphenhydramine, desloratidine, loratidine, cyproheptadine, brompheniramine, emedastine, levocabastine, carbinoxamine, levocetirizine, clemastine, cetirizine, phenylephrine, pseudoephedrine, oxymetazoline, pyrilamine, doxylamine, codeine, pholcodine, dextromethorphan, noscapine, butamirate, acetylcysteine, menthol, quetiapine, and guaifenesin. The conjugated dextrorphan of the present technology can be formulated with one or a combination of these or other active substances, or as a stand alone active ingredient without any other actives.

The amounts and relative percentages of the different active and inactive components of the formulations of the current technology can be modified, selected and adjusted in order to arrive at desirable formulations, dosages and dosage forms for therapeutic administration of the compounds, products, compositions, conjugates and prodrugs of the current technology.

In one embodiment, the compositions comprising the dextrorphan conjugates or prodrugs may be used in methods of treating a patient having a disease, disorder, condition, or syndrome requiring or mediated by binding of an NMDA receptor antagonist to an NMDA receptor of the patient. In some embodiments, compositions comprising the dextrorphan conjugates of the present technology may be used as an anesthetic, or for the treatment of such conditions as opioid dependence, hyperalgesia, pseudobulbar affect (PBA), neuropathy, diabetic peripheral neuropathic pain, catalepsy, amnesia, Alzheimer's disease, depression, and post-traumatic stress disorder (PTSD). In certain embodiments, the compositions comprising the dextrorphan conjugates of the present technology may be used in combination with quinidine for the treatment of PBA and/or PTSD. In other embodiments, compositions of the present technology may potentiate the effects of certain opioids, such as for example oxycodone, in suppressing neuropathic pain, thus potentially permitting a lower dose of oxycodone to be administered to a patient and thereby decreasing side effects of oxycodone treatment of neuropathic pain in said patient.

Treatment comprises orally administering to the patient a pharmaceutically effective amount of at least one conjugate of dextrorphan as described in the present technology. The patient may be a human or animal patient. As used herein, the term animal is used in the veterinary sense and does not include humans. Human patients who may be treated include neonatal patients, pediatric patients, adolescent patients, adult patients, geriatric patients, elderly patients, and normative patients. In some embodiments, the conjugate can exhibit a lower, equivalent, or higher AUC when compared to an equivalent molar amount of unconjugated dextrorphan, and can exhibit a slower, similar, or faster rate of release. In other embodiments, at least one conjugate can exhibit less variability in the oral PK profile when compared to unconjugated dextrorphan.

In some embodiments, the prodrugs or compositions of the present technology may be administered for the relief or suppression of cough, impulse to cough, sneezing, itching of the nose, throat or watery eyes, nasal congestion, sinus congestion and pressure, sore throat, headache, minor aches and pains, muscular pain, fever, upper respiratory symptoms, and bronchial irritation. Dosing of the prodrugs or compositions will be dependent on the age and body weight of the patient, and the severity of the symptoms to be treated.

In some embodiments, dosages of the dextrorphan conjugate of the present technology include, but are not limited to, formulations including from about 0.5 mg or higher, alternatively from about 2.5 mg or higher, alternatively from about 5.0 mg or higher, alternatively from about 7.5 mg or higher, alternatively from about 10 mg or higher, alternatively from about 20 mg or higher, alternatively from about 30 mg or higher, alternatively from about 40 mg or higher, alternatively from about 50 mg or higher, alternatively from about 60 mg or higher, alternatively from about 70 mg or higher, alternatively from about 80 mg or higher, alternatively from about 90 mg or higher, alternatively from about 100 mg or higher of the dextrorphan conjugate, and include any additional increments thereof, for example, 0.1, 0.2, 0.25, 0.3, 0.4, 0.5, 0.6, 0.7, 0.75, 0.8, 0.9 or 1.0 mg and multiplied factors thereof, (e.g., ×1, ×2, ×2.5, ×5, ×10, ×100, etc.).

In some embodiments, compositions comprising the dextrorphan conjugates of the present technology could be orally administered at a dosing regimen of one time a day, alternatively two times a day, alternatively four times a day. In some embodiments, doses of the composition comprising the levorphanol conjugate could be administered at 1 dose every 4 to 6 hours, alternatively 1 to 2 doses every 4 to 6 hours, alternatively every 6 to 8 hours, alternatively 4 doses in a 24 hour period. In further embodiments, doses of the composition comprising the levorphanol conjugate could be administered at 1 dose about every 12 hours, alternatively 1 to 2 doses about every 12 hours, alternatively 2 doses every 24 hours, alternatively 1 dose about every 24 hours.

In some embodiments, compositions comprising the dextrorphan conjugates of the present technology could be administered for a period of about 3 days, alternatively about 5 days, alternatively about 7 days, alternatively about 10 days, alternatively about 12 days, alternatively about 14 days, alternatively about 21 days, alternatively about 30 days, alternatively about 60 days, alternatively about 90 days, alternatively about 120 days, alternatively more than 120 days.

Pharmaceutical Kits

In some embodiments, the present technology provides pharmaceutical kits comprising a dextrorphan prodrug or composition of the present technology. In some embodiments, a specific amount of individual doses in a package contain a pharmaceutically and/or therapeutically effective amount of the dextrorphan prodrug or conjugate of the present technology. In some embodiments, the kit comprises one or more blister packs containing the prodrug or composition of the present technology. In some embodiments, the kit may comprise one or more dextrorphan conjugate composition of the present technology and optionally one or more additional compositions containing other active ingredients for a particular treatment regimen. For example, the kit may be a daytime/nighttime kit that contains one composition for daytime treatment and one composition for nighttime treatment. In other embodiments, the kit could be, for example, a "family kit" that comprises different dosage strengths of the dextrorphan conjugate composition or different containers containing doses of the dextrorphan conjugate composition, for example, one dosage strength or container for adults, and another for children.

The kit can further include instructions for use of the kit. In some embodiments, the instructions for use are for the treatment of pain or cough in a neonatal, pediatric, adolescent, adult, normative, or geriatric patient. In other embodiments, the instructions for use are for the treatment of any of the diseases, disorders, conditions, or syndromes identified above. The specified amount of individual doses may contain from about 1 to about 100 individual dosages, alternatively from about 1 to about 60 individual dosages, alternatively from about 10 to about 30 individual dosages, including, about 1, about 2, about 5, about 10, about 15, about 20, about 25, about 30, about 35, about 40, about 45, about 50, about 55, about 60, about 70, about 80, about 100, and include any additional increments thereof, for example, about 1, about 2, about 5, about 10 and multiplied factors thereof, (e.g., about ×1, about ×2, about ×2.5, about ×5, about ×10, about ×100, etc.).

Synthetic Schemes

The present technology also provides a method of synthesis for the preparation of the conjugated dextrorphan of the present technology. In some embodiments, one or more protecting groups may be attached to any additional reactive functional groups that may interfere with the coupling to dextrorphan. Any suitable protecting group may be used depending on the type of functional group and reaction conditions. Some protecting group suitable for use in the present technology include, but are not limited to, acetyl (Ac), tert-butyoxycarbonyl (Boc), benzyloxycarbonyl (Cbz), p-methoxybenzylcarbonyl (Moz), 9-fluorenylmethyloxycarbonyl (Fmoc), benzyl (Bn), p-methoxybenzyl (PMB), 3,4 dimethoxybenzyl (DMPM), p-methozyphenyl (PMP), tosyl (Ts), or amides (like acetamides, pthalamides, and the like).

In other embodiments, a base may be required at any step in the synthetic scheme of prodrugs of dextrorphan of this invention. Suitable bases include, but are not limited to, 4-methylmorpholine (NMM), 4-(dimethylamino)pyridine (DMAP), N,N-diisopropylethylamine, lithium bis(trimethylsilyl)amide, lithium diisopropylamide (LDA), any alkali metal tert.-butoxide (e.g., potassium tert.-butoxide), any alkali metal hydride (e.g., sodium hydride), any alkali metal alkoxide (e.g., sodium methoxide), triethylamine or any other tertiary amine.

Suitable solvents that can be used for any reaction at any step in the synthetic scheme of a prodrug of dextrorphan of this invention include, but are not limited to, acetone, acetonitrile, butanol, chloroform, dichloromethane, dimethylformamide (DMF), dimethylsulfoxide (DMSO), dioxane, ethanol, ethyl acetate, diethyl ether, heptane, hexane, methanol, methyl tert.-butyl ether (MTBE), isopropanol, isopropyl acetate, diisopropyl ether, tetrahydrofuran, toluene, xylene or water.

In some embodiments, an acid may be used to remove certain protecting groups. Suitable acids include, but are not limited to, hydrochloric acid, hydrobromic acid, hydrofluoric acid, hydriodic acid, sulfuric acid, phosphoric acid, trifluoroacetic acid, acetic acid, citric acid, methanesulfonic acid, p-toluenesulfonic acid and nitric acid. For certain other protecting groups, a catalytic hydrogenation may be used, e.g., palladium on charcoal in the presence of hydrogen gas.

Provided herein are some reaction schemes that could be used to prepare some embodiments of the dextrorphan conjugates of the present technology. It should be understood that the general reaction schemes provided are exemplary, and that one skilled in the art can modify or tailor the reaction schemes to achieve particular outcomes, purposes, and/or advantages.

Scheme 1

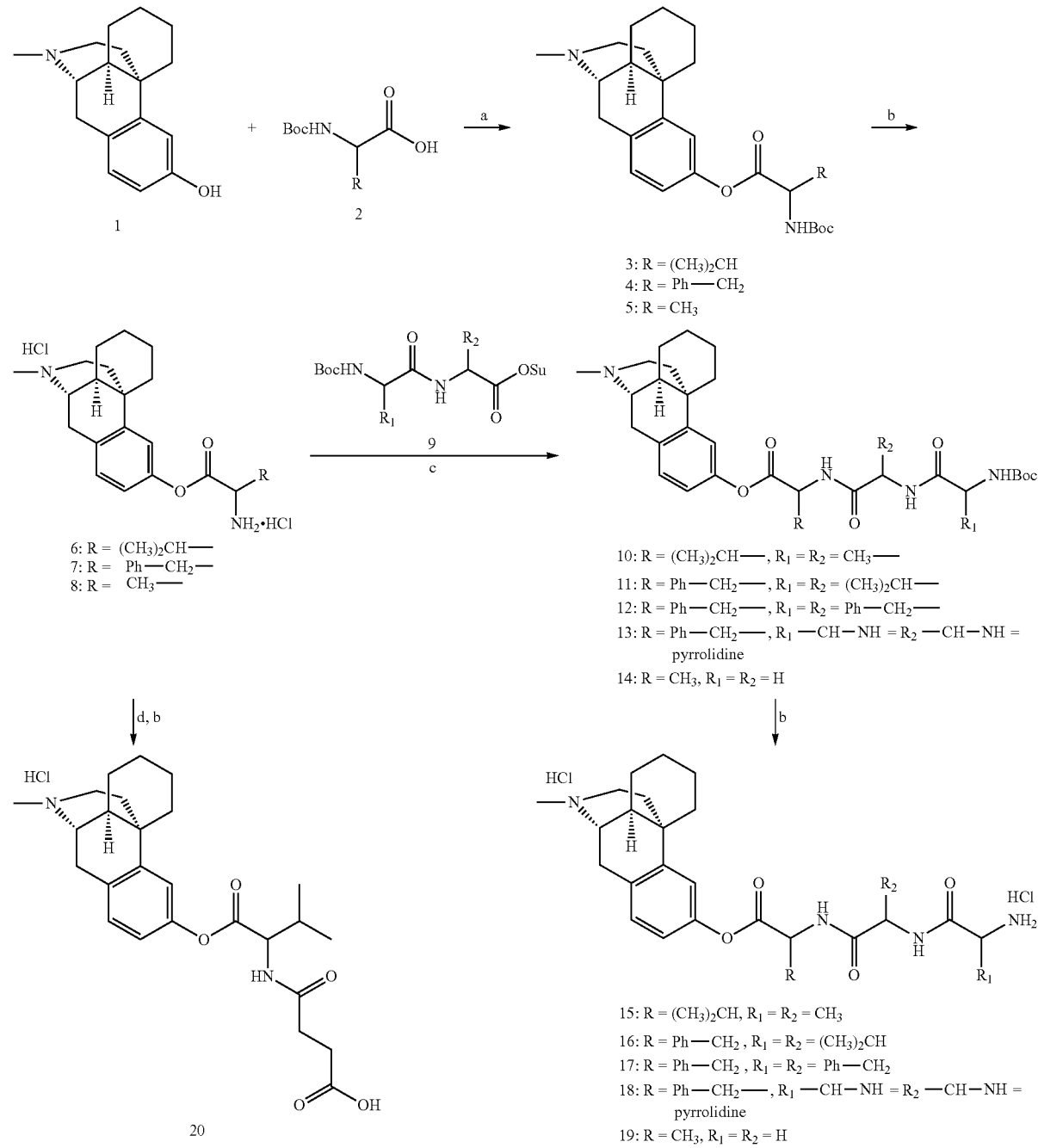

a HBTU, HOBt, TEA, DMF;
b 4N HCl/dioxane;
c 9, N-methylmorpholine, DMF;
d succinic anhydride, DMF

3-Val-dextrorphan 6

To a solution of dextrorphan, BocValOH and trimethylamine in DMF is added a solution of HBTU in DMF. The reaction mixture is stirred at room temperature overnight. The reaction is quenched with water and the solvent is evaporated under reduced pressure. The residue is taken in EtOAc, washed with 5% aq. $NaHCO_3$ and brine. The organic part is dried over anhydrous $Na_2SO_4$ and is evaporated to dryness to give 3-(Boc-Val)-dextrorphan 3.

A solution of 3-(Boc-Val)-dextrorphan 3 in 4N HCl in dioxane is stirred at room temperature. The solvent is evaporated under reduced pressure, the residue is co-evaporated with IPAc and dried to give compound 6.

3-Phe-dextrorphan 7

A solution of HBTU is added to a solution of dextrorphan, Boc-Phe-OH, HOBt and trimethylamine in DMF is added. The reaction mixture is stirred at room temperature. The reaction is quenched with water and the solvent is evaporated under reduced pressure. The residue is taken in EtOAc, and washed with 5% aq. $NaHCO_3$ and brine. The organic part is dried over anhydrous $Na_2SO_4$ and is evaporated to dryness to give 3-(Boc-Phe)-dextrorphan 4.

A solution of 3-(Boc-Phe)-dextrorphan 4 in 4N HCl in dioxane is stirred at room temperature. The solvent is evaporated under reduced pressure, the residue is co-evaporated with IPAc and is dried to give the compound 7.

3-Ala-dextrorphan 8

Reaction of 1 and Boc-Ala-OH is performed following the same procedure as described for the synthesis of compound 7 to produce compound 5. Deprotection of 5 with 4N HCl in dioxane gives compound 8.

3-(AlaAlaVal)-dextrorphan 15

To a solution of 3-Val-dextrorphan 6 in DMF is added N-methylmorpholine and Boc-Ala-Ala-OSu. The reaction mixture is stirred at room temperature. The reaction is quenched with water and the solvent is evaporated under reduced pressure. The residue is partitioned between EtOAc and 5% aqueous $NaHCO_3$. The EtOAc layer is washed with 5% aq. $NaHCO_3$, brine, dried over anhydrous $Na_2SO_4$ and is evaporated to dryness to give 3-(Boc-AlaAlaVal)-dextrorphan 10.

The tripeptide derivative 10 is dissolved in 4N HCl in dioxane and is stirred at room temperature. Solvent is evaporated, the residue is co-evaporated with IPAc and is dried to give the tripeptide derivative 15.

3-(ValValPhe)-dextrorphan 16

To a solution of 3-Phe-dextrorphan 7 and N-methylmorpholine in DMF is added Boc-ValVal-OSu. The reaction mixture is stirred at room temperature and is then heated. The reaction is quenched with water and the solvent is evaporated under reduced pressure and gives 3-(Boc-ValValPhe)-dextrorphan 11.

A solution of compound 11 in 4N HCl in dioxane is stirred at room temperature. Solvent is evaporated, the residue is co-evaporated with IPAc and is dried to give the tripeptide derivative 16.

3-(PhePhePhe)-dextrorphan 17

To a solution of 3-Phe-dextrorphan 7 in DMF is added N-methylmorpholine and Boc-PhePhe-OSu. The reaction mixture is stirred at room temperature. The reaction is quenched with water and the solvent is evaporated under reduced pressure. The residue is taken in EtOAc, and washed with 5% aqueous $NaHCO_3$ and brine. The organic part is dried over anhydrous $Na_2SO_4$ and is evaporated to dryness to give 3-(Boc-PhePhePhe)-dextrorphan 12.

Compound 12 is dissolved in 4N HCl in dioxane and is stirred at room temperature. Solvent is evaporated, the residue is co-evaporated with IPAc and is dried to give the tripeptide derivative 17.

3-(ProProPhe)-dextrorphan 18

Compound 18 is prepared following the procedure described for the synthesis of compound 16, except Boc-ProPro-OSu is used in place of Boc-ValVal-OSu.

3-(GlyGlyAla)-dextrorphan 19

A mixture of compound 8, N-methylmorpholine and Boc-GlyGly-OSu in DMF is stirred at room temperature. Solvent is evaporated under reduced pressure to give the tripeptide derivative 14.

A solution of 14 in 4N HCl in dioxane is stirred at room temperature. Solvent is removed under vacuum, the residue is co-evaporated with IPAc and is dried to give 19.

3-(N-succinoyl-Val)-dextrorphan 20

A solution of compound 6, triethylamine and succinic anhydride in DMF is heated. Solvent is evaporated under reduced pressure and provides 3-(N-succinoyl-Val)-dextrorphan. The purified product is treated with 4N HCl in dioxane to give the hydrochloride salt 20.

Scheme 2

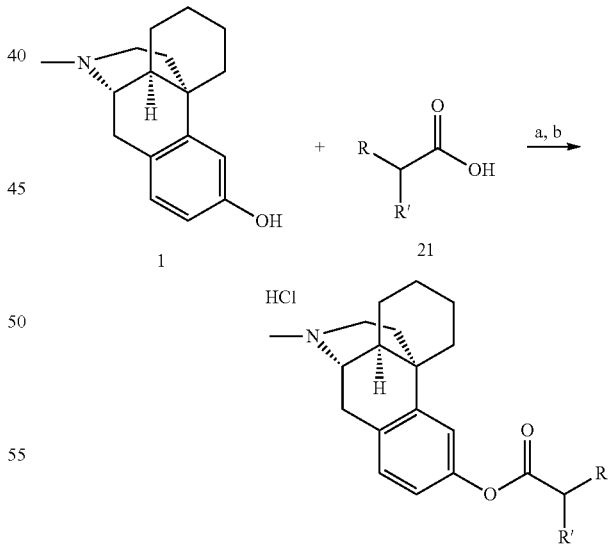

22: R = BzNH———, R' = H
23: R = AcNH, R' = $CH_3$——$CH_2$—$CH(CH_3)$
24: R = AcNH, R' = 4-tert-butyloxybenzyl
25: R = AcNH, R' = 4-hydroxybenzyl
26: R = OAc, R' = Ph a 21, HBTU, HOBtM TEA, DMF;
b 4N HCl/dioxane

3-Hippuryl-dextrorphan 22

To a solution of dextrorphan 1, hippuric acid, HOBt and trimethylamine in DMF is added a solution of HBTU in DMF. The reaction mixture is stirred at room temperature. The reaction is quenched with water and the solvent is evaporated under reduced pressure. The residue is taken in EtOAc, and washed with 5% aq. NaHCO$_3$ and brine. The EtOAc part is dried over anhydrous Na$_2$SO$_4$ and is evaporated to dryness to give 3-hippuryl-dextrorphan. The purified product is dissolved in 4N HCl in dioxane and is stirred at room temperature. The solvent is evaporated under reduced pressure, and the residue is co-evaporated with IPAc and is dried to obtain hydrochloride salt 22.

3-(N-acetyl-Ile)-dextrorphan 23

Reaction of dextrorphan with Ac-Ile-OH is carried out in a manner similar to that described for the synthesis of 22 to obtain 3-(N-acetyl-Ile)-dextrorphan. The N-acetyl-isoleucine derivative is converted to the corresponding hydrochloride salt by treatment with 4N HCl in dioxane to give the hydrochloride salt 23.

3-(N-acetyl-Tyr)-dextrorphan 25

Reaction of dextrorphan, Ac-Tyr($^t$Bu)-OH to give compound 24 is carried out following the same procedure as described for the synthesis of 22.

A solution of 24 in 4N HCl in dioxane is stirred at room temperature. Solvent is evaporated and the residue is co-evaporated with IPAc and is dried to give compound 25.

3-(Acetyl-OCH(phenyl)C(O))-dextrorphan 26

The reaction of dextrorphan and O-acetylmandelic acid is carried out following the same procedure as described for the synthesis of 22. The crude product is purified and is then converted to the HCl salt by treatment with 2N HCl in dioxane to produce hydrochloride salt 26.

Scheme 3.

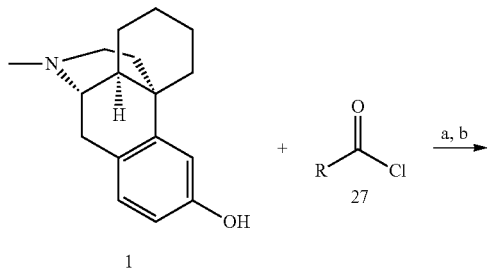

a 27, TEA, CH$_2$Cl$_2$;
b HCl/dioxane

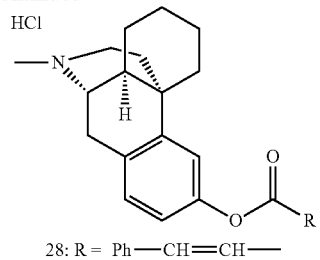

28: R = Ph—CH=CH—
29: R = AcO—CH$_2$—
30: R = CH$_3$—CH(OAc)—

3-Cinnamoyl-dextrorphan 28

A solution of cinnamoyl chloride in CH$_2$Cl$_2$ is added to a solution of dextrorphan 1 and trimethylamine in CH$_2$Cl$_2$. After the addition, the reaction mixture is stirred. Additional CH$_2$Cl$_2$ is added and the organic part is washed with 5% aqueous NaHCO$_3$, and brine. The CH$_2$Cl$_2$ part is dried over anhydrous Na$_2$SO$_4$ and is evaporated to dryness to afford 3-cinnamoyl-dextrorphan. The purified product is dissolved in 4N HCl in dioxane and is stirred at room temperature. Solvent is evaporated under vacuum and the residue is dried to give hydrochloride salt of 28.

3-(Acetyl-OCH$_2$C(O))-dextrorphan 29

A solution of dextrorphan 1 and trimethylamine in CH$_2$Cl$_2$ is cooled and a solution of acetyloxyacetyl chloride in CH$_2$Cl$_2$ is added drop wise. After the addition, the reaction mixture is stirred at room temperature. The reaction is quenched with water and the solvent is evaporated under reduced pressure. The product is purified and is treated with 2N HCl in dioxane to give hydrochloride salt 29.

3-(Acetyl-OCH(CH$_3$)C(O))-dextrorphan 30

A solution O-acetyl lactyl chloride in CH$_2$Cl$_2$ is added to a solution of dextrorphan 1 and trimethylamine in CH$_2$Cl$_2$. After the addition, the reaction mixture is stirred. Solvent is evaporated under reduced pressure. The residue is dissolved in CH$_2$Cl$_2$, and washed with 5% aqueous NaHCO$_3$ and brine. The CH$_2$Cl$_2$ part is dried over anhydrous Na$_2$SO$_4$ and is evaporated to dryness. The crude product is purified and is converted to the corresponding hydrochloride salt 30 by treatment with 2N HCl in dioxane.

Scheme 4.

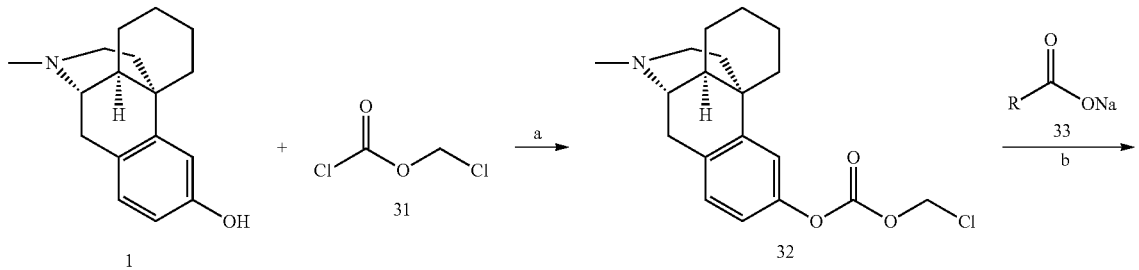

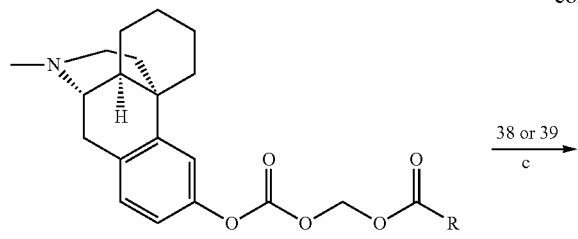

34; R = Ph——
35; R = CH₃——CH₂—CH₂——
36; R = Ph——CH═CH——
37; R = RC(O) = Ac——Lys(Ac)——
38; R = RC(O) = Boc——Val——
39; R = RC(O) = Boc——Tyr(ᵗBu)——

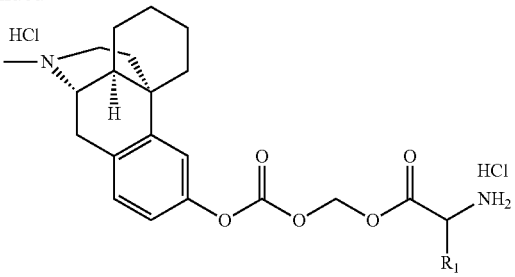

40: R₁ = (CH₃)₂CH——
41: R = 4-hydroxybenzyl——

↓ d, e

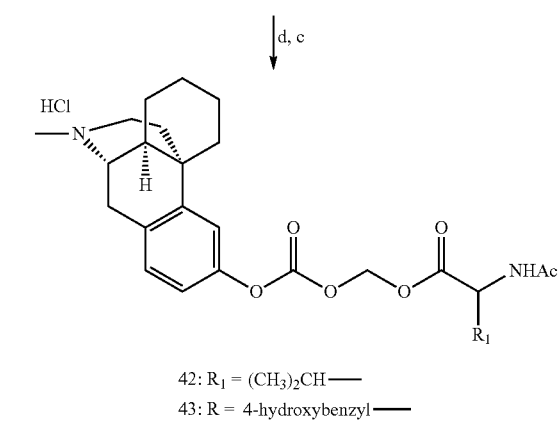

42: R₁ = (CH₃)₂CH——
43: R = 4-hydroxybenzyl—— a TEAM CH₂Cl₂;
b 33, DMF, heat;
c 4N HCl/dioxane;
d Acetyl chloride, TEA, CH₂Cl₂;
e HCl/dioxane

3-(Chloromethyloxycarbonyl)-dextrorphan 32

A solution of chloromethyl chloroformate 31 in CH₂Cl₂ is added to a solution of dextrorphan and trimethylamine in CH₂Cl₂. After the addition, the reaction mixture is stirred. The reaction is quenched with water and solvent is evaporated under reduced pressure. The residue is taken in EtOAc, and washed with water and brine, is dried over anhydrous Na₂SO₄ and is evaporated to dryness to give 32.

3-(Benzoyl-OCH₂OC(O)-dextrorphan 34

A solution of 32 and sodium benzoate in DMF is heated. Solvent is evaporated under reduced pressure. The residue is taken in EtOAc, and washed with 5% aq. NaHCO₃ and brine. The organic part is dried over anhydrous Na₂SO₄ and is evaporated to dryness to give 34. The purified benzoyl derivative is dissolved in 4N HCl in dioxane, is stirred at room temperature, and then solvent is evaporated under vacuum. The resulting residue is dried to give the hydrochloride salt of 34.

3-(Butanoyl-OCH₂OC(O))-dextrorphan 35

Reaction of 32 with sodium butyrate to obtain 35 is carried out in a manner similar to that described for the synthesis of 34. The crude product is purified and is treated with 4N HCl in dioxane to obtain hydrochloride salt of 35.

3-(Cinnamoyl-OCH₂OC(O))-dextrorphan 36

A solution of 32 and sodium cinnamate in DMF is heated. Solvent is evaporated under reduced pressure. The residue is taken in EtOAc, and washed with 5% aq. NaHCO₃ and brine. The organic part is dried over anhydrous Na₂SO₄ and is evaporated to dryness. The crude product is isolated as hydrochloride salt of 36 by treatment with 4N HCl in dioxane.

3-(N,O-acetyl-Lys-OCH₂OC(O))-dextrorphan 37

A solution of 32 and Ac-Lys(Ac)-ONa in DMF is heated. Solvent is evaporated under reduced pressure. The residue is taken in EtOAc, and washed with 5% aq. NaHCO₃ and brine. The organic part is dried over anhydrous Na₂SO₄ and is evaporated to dryness. The crude product is purified and is treated with 4N HCl in dioxane to give hydrochloride salt of 37.

General Procedure for the Synthesis of Sodium Salt of N-Protected Amino Acids (Boc-AA-ONa)

To a solution or suspension or solution (depending on amino acids) of Boc-AA-OH in CH₃CN/water is added 1N NaOH drop-wise while stirring.

3-(Boc-Val-OCH₂OC(O))-dextrorphan 38

A solution of 32 and Boc-Val-ONa in DMF is heated. Solvent is evaporated under reduced pressure. The residue is taken in EtOAc, and washed with 5% aq. NaHCO₃ and brine. The organic part is dried over anhydrous Na₂SO₄ and is evaporated to dryness to give 38.

3-(Val-OCH₂OC(O))-dextrorphan 40

A solution of 38 in 4N HCl in dioxane is stirred at room temperature. Solvent is evaporated under reduced pressure, the residue is co-evaporated with IPAc and is dried to give 40. Compound 40 is converted to the acetyl derivative 42.

3-(N-acetyl-Val-OCH₂OC(O))-dextrorphan 42

A solution of 40 and TEA in CH₂Cl₂ is cooled and a solution of acetyl chloride in CH₂Cl₂ is added drop wise. The reaction mixture is stirred at room temperature. Solvent is evaporated under reduced pressure and the residue is partitioned between EtOAc and 5% aqueous NaHCO₃. The EtOAc layer is washed with 5% aq. NaHCO₃ and brine, is dried over anhydrous Na₂SO₄ and is evaporated to dryness.

The purified product is dissolved in 4N HCl in dioxane, is stirred and is then evaporated to dryness under vacuum to give the hydrochloride salt 42.

3-(N,O-diacetyl-Tyr)-dextrorphan 43

A solution of 32 and Boc-Tyr(ᵗBu)-ONa in DMF is stirred at room temperature, and then is heated. Solvent is evaporated under reduced pressure. The residue is dissolved in EtOAc, and washed with 5% aq. NaHCO₃ and brine. The organic part is dried over anhydrous Na₂SO₄ and is evaporated to dryness to give 39.

Compound 39 is dissolved in 4N HCl in dioxane and the solution is stirred at room temperature. Solvent is evaporated under reduced pressure, and the residue is co-evaporated with IPAc and is dried to give 41.

A solution of 41 and TEA in CH₂Cl₂ is cooled and a solution of acetyl chloride in CH₂Cl₂ is added drop wise. After the addition, the reaction mixture is stirred at room temperature. Solvent is evaporated under reduced pressure and the residue is partitioned between EtOAc and 5% aqueous NaHCO₃. The EtOAc layer is washed with 5% aq. NaHCO₃ and brine, is dried over anhydrous Na₂SO₄ and is evaporated to dryness. The crude product is purified and is then treated with 4N HCl in dioxane to give the hydrochloride salt 43.

Scheme 5.

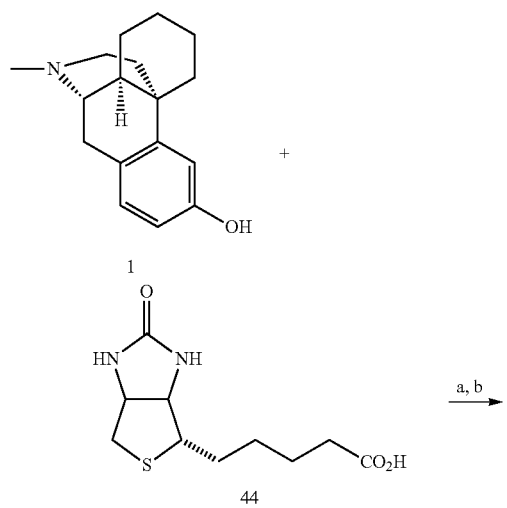

3-Biotinyl-dextrorphan 45

A solution of HBTU in DMF is added to a solution of dextrorphan 1, biotin 44, HOBt and trimethylamine in DMF at room temperature. The reaction is quenched with water and the solvent is evaporated under reduced pressure. 5% Aqueous NaHCO₃ is added to the residue and the mixture is extracted with CH₂Cl₂. The combined organic parts is washed with 5% aq. NaHCO₃ and brine, is dried over anhydrous Na₂SO₄ and is evaporated to dryness to give 3-biotinyl-dextrorphan. The crude product is purified and is treated with 4N HCl in dioxane to give the hydrochloride salt 45.

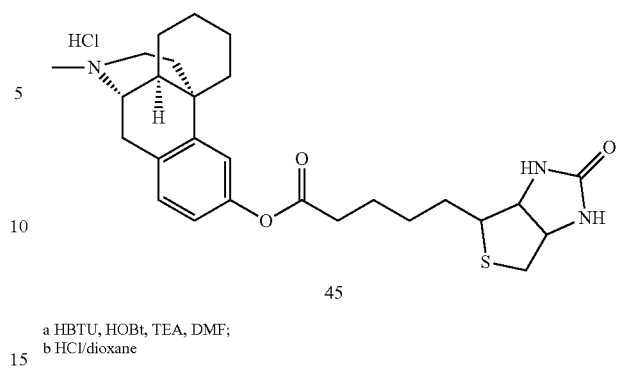

45 a HBTU, HOBt, TEA, DMF;
b HCl/dioxane

Scheme 6.

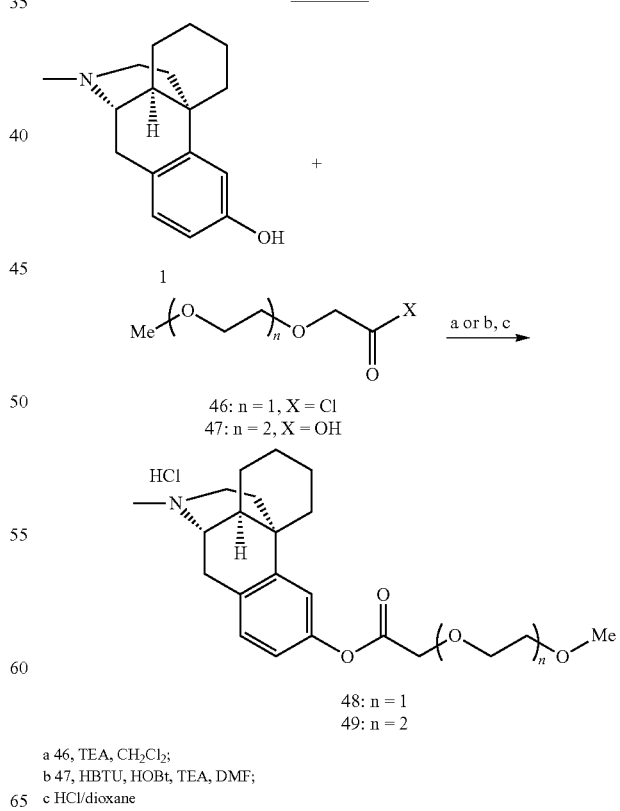

a 46, TEA, CH₂Cl₂;
b 47, HBTU, HOBt, TEA, DMF;
c HCl/dioxane

3-(Methoxy-(ethoxy)-CH$_2$C(O))-dextrorphan 48

A solution of 2-methoxyethoxy acetyl chloride 46 in CH$_2$Cl$_2$ is added to a solution of dextrorphan and trimethylamine in CH$_2$Cl$_2$. After the addition, the reaction mixture is stirred. Additional CH$_2$Cl$_2$ is added, and the organic part is washed with 5% aqueous NaHCO$_3$ and brine. The CH$_2$Cl$_2$ part is dried over anhydrous Na$_2$SO$_4$ and is evaporated to dryness. The residue is purified, is dissolved in 4N HCl in dioxane, is stirred at room temperature, and is then evaporated under reduced pressure to give the hydrochloride salt 48.

3-(Methoxy-PEG$_2$-CH$_2$C(O))-dextrorphan 49

To a solution of dextrorphan 1, 2-[2-2-methoxyethoxy)ethoxy] acetic acid 47, HOBt and trimethylamine in DMF is added a solution of HBTU in DMF. The reaction mixture is stirred at room temperature. The reaction is quenched with water and the solvent is evaporated under reduced pressure. The residue is partitioned between CH$_2$Cl$_2$ and 5% aq. NaHCO$_3$. The aqueous part is extracted with CH$_2$Cl$_2$. The combined organic part is finished with brine, is dried over anhydrous Na$_2$SO$_4$ and is evaporated to dryness. The purified product is dissolved in 2N HCl in dioxane, is stirred at room temperature and is then evaporated under reduced pressure to give the hydrochloride salt 49.

Scheme 7.

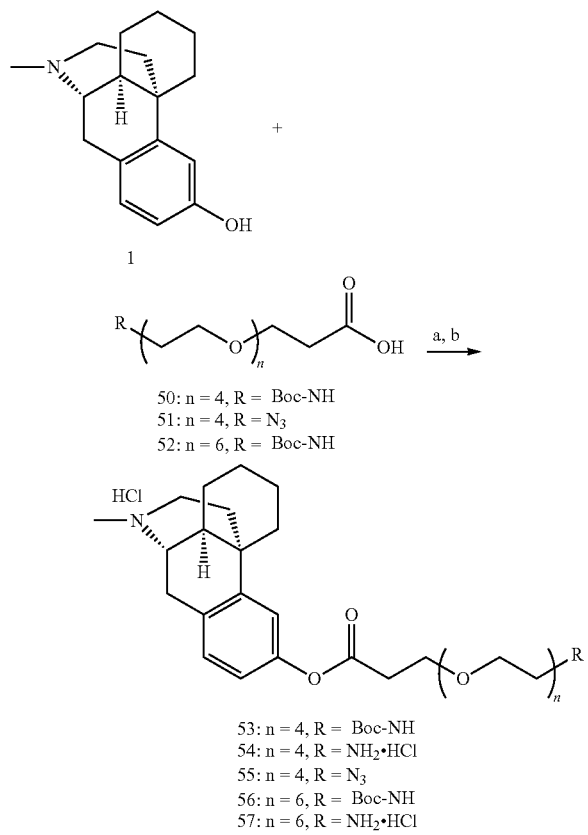

50: n = 4, R = Boc-NH
51: n = 4, R = N$_3$
52: n = 6, R = Boc-NH

53: n = 4, R = Boc-NH
54: n = 4, R = NH$_2$·HCl
55: n = 4, R = N$_3$
56: n = 6, R = Boc-NH
57: n = 6, R = NH$_2$·HCl a HBTU, HOBt, TEA, DMF;
b 4N HCl/dioxane

3-(H$_2$N-PEG$_4$-CH$_2$CH$_2$C(O))-dextrorphan 54

To a solution of dextrorphan 1, Boc-NH-(PEG)$_4$-CH$_2$CH$_2$—COOH 50, HOBt and trimethylamine in DMF is added a solution of HBTU in DMF. The reaction mixture is stirred at room temperature. The reaction is quenched with water and the solvent is evaporated under reduced pressure. The residue is taken in EtOAc, and washed with 5% aq. NaHCO$_3$ and brine. The organic part is dried over anhydrous Na$_2$SO$_4$ and is evaporated to dryness to give 53.

A solution of 53 in 4N HCl in dioxane is stirred at room temperature. Solvent is evaporated under pressure, the residue is co-evaporated with IPAc and is dried to give the deprotected product 43.

3-(N$_3$-PEG$_4$-CH$_2$CH$_2$C(O))-dextrorphan 55

A solution of HBTU in DMF is added to a solution of dextrorphan 1, N$_3$-(PEG)$_4$-CH$_2$CH$_2$—COOH 51, HOBt and trimethylamine in DMF. The reaction mixture is stirred at room temperature. The reaction is quenched with water and the solvent is evaporated under reduced pressure. The residue is taken in CH$_2$Cl$_2$, and washed with 5% aq. NaHCO$_3$ and brine. The organic part is dried over anhydrous Na$_2$SO$_4$ and is evaporated to dryness. The purified product is dissolved in 2N HCl in dioxane and is stirred at room temperature. Solvent is evaporated under pressure, is co-evaporated with IPAc and is dried to give the hydrochloride salt 55.

3-(H$_2$N-PEG$_6$-CH$_2$CH$_2$C(O))-dextrorphan 57

To a solution of dextrorphan 1, Boc-NH-(PEG)$_6$-CH$_2$CH$_2$—COOH, HOBt and trimethylamine in DMF is added a solution of HBTU in DMF. The reaction mixture is stirred at room temperature. The reaction is quenched with water and the solvent is evaporated under reduced pressure. The residue is taken in CH$_2$Cl$_2$, and washed with 5% aq. NaHCO$_3$ and brine. The organic part is dried over anhydrous Na$_2$SO$_4$ and is evaporated to dryness to give 56.

A solution of 56 in 4N HCl in dioxane is stirred at room temperature. Solvent is evaporated under pressure, the residue is co-evaporated with IPAc, and is dried to give the deprotected product 57.

Scheme 8.

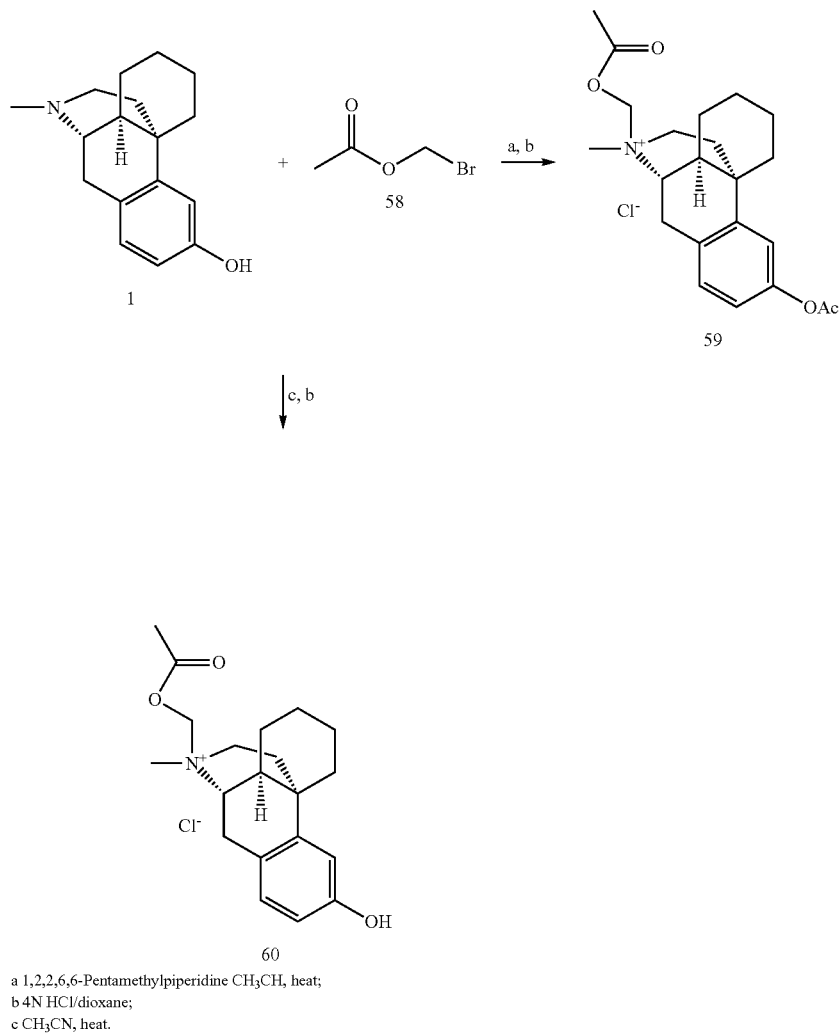

a 1,2,2,6,6-Pentamethylpiperidine CH₃CH, heat;
b 4N HCl/dioxane;
c CH₃CN, heat.

3-Acetyl-N-(acetyl-OCH₂)-dextrorphanium 3

A solution of dextrorphan 1, 1,2,2,6,6-pentamethylpiperidine and acetyloxymethyl bromide 58 in CH₃CN is heated. Solvent is evaporated under reduced pressure. The purified quaternary salt is dissolved in 4N HCl in dioxane and is stirred at room temperature. The solvent is evaporated, the residue is co-evaporated with IPAc and is dried to give the chloride salt 59.

N-(Acetyl-OCH₂)-dextrorphanium 60

A solution of dextrorphan 1 and acetyloxymethyl bromide 58 in CH₃CN is heated. Solvent is evaporated under reduced pressure. The purified quaternary salt is dissolved in 4N HCl in dioxane and is stirred at room temperature. The solvent is evaporated, the residue is co-evaporated with IPAc and is dried to give the chloride salt 60.

Scheme 9.

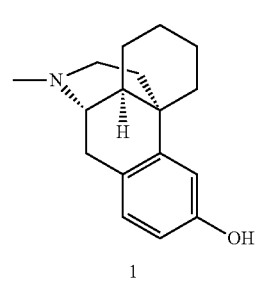

1

+

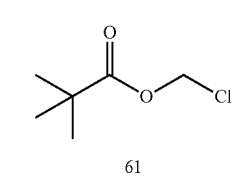

61 a, b

-continued

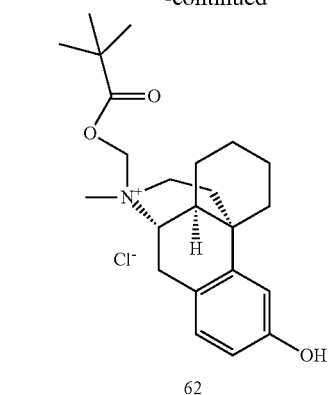
62

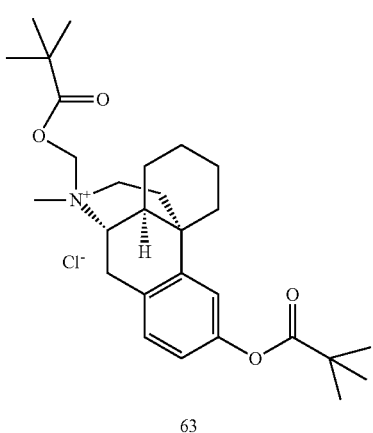
63

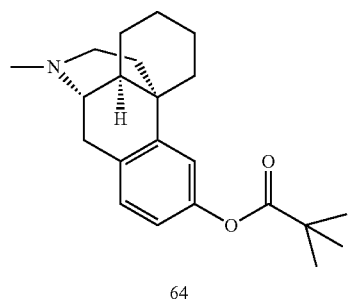
64 a CH₃CH, heat;
b Dowex 1 × 4 chloride, water/CH₃CH;
c 1,2,2,6,6-Pentamethylpiperidine CH₃CH, heat.

N-(Pivaloyl-OCH₂)-dextrorphanium 62, 3-pivaloyl-N-(pivaloyl-OCH₂)-dextrorphanium Chloride 63 and 3-pivaloyl-dextrorphan 64

A suspension of dextrorphan 1 and chloromethyl pivalate 61 in CH₃CN is heated. Solvent is evaporated under reduced pressure. The quaternary salts, after separation, is treated with Dowex 1×4 chloride form, is filtered and the filtrate is lyophilized to afford compound 62 and 63. In addition, conjugate 64 may form.

Prophetic Synthesis of Cbz-Val-O—CH₂—Cl

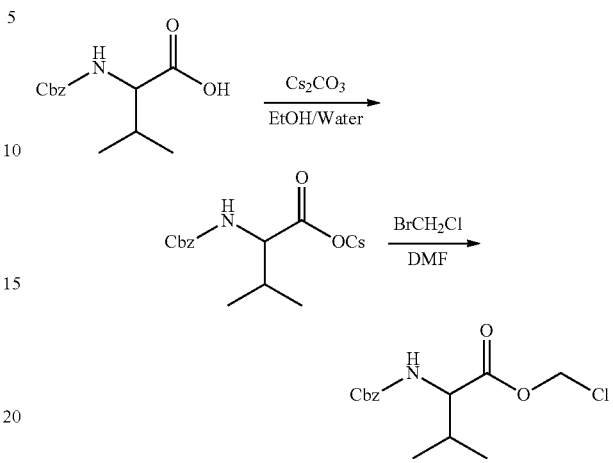

Prophetic Synthesis of N-(Val-CH₂)-dextrorphanium

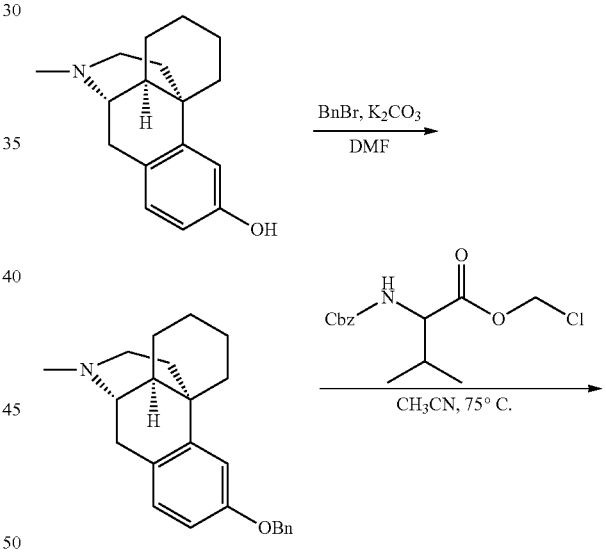

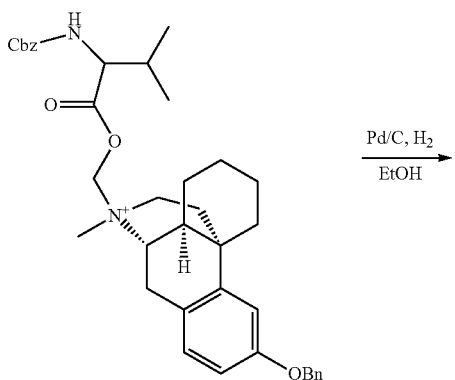

-continued
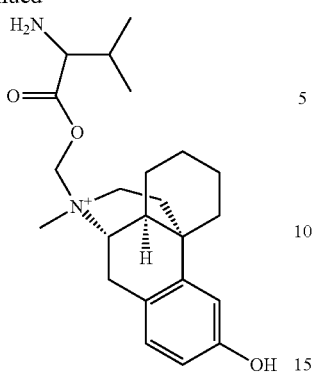
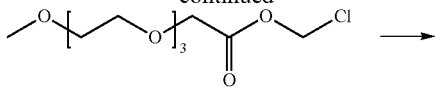
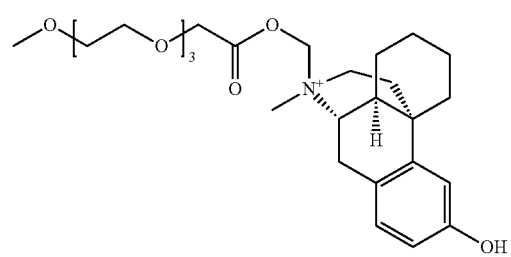
Prophetic Synthesis of MeO-PEG₃-CH₂C(O)OCH₂—Cl
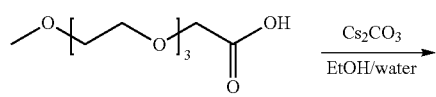
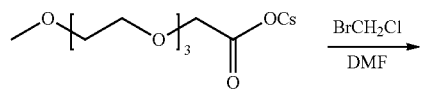
Prophetic Synthesis of N-(MeO-PEG₃-CH₂C(O)OCH₂)-dextrorphanium
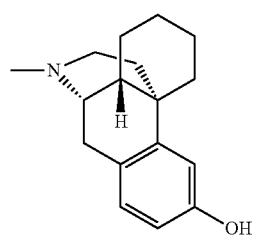 +
Prophetic Synthesis of Boc-Ser(C(O)OCH₂Cl)—OᵗBu
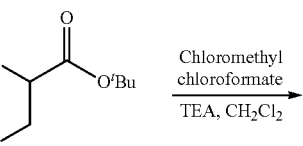
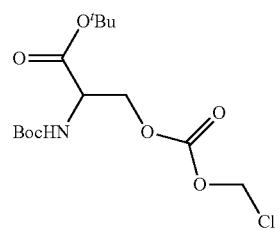

Prophetic Synthesis of N-(Ser(C(O)OCH$_2$)—OH)-dextrorphanium
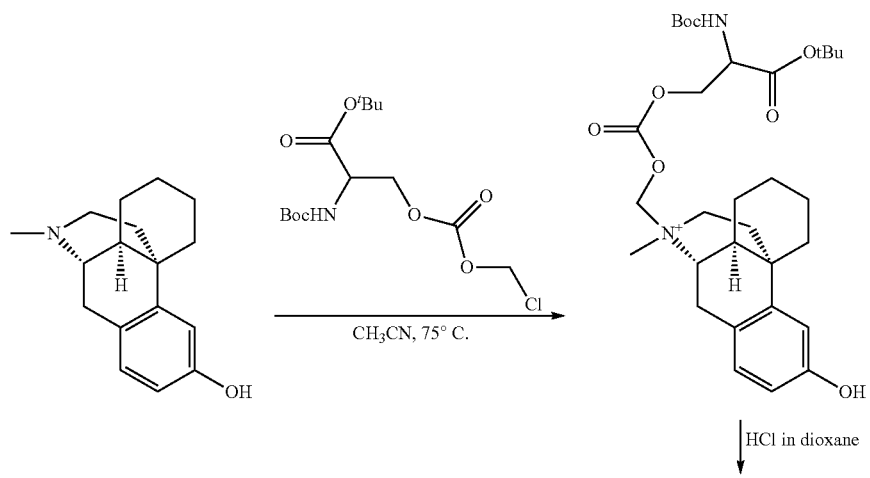
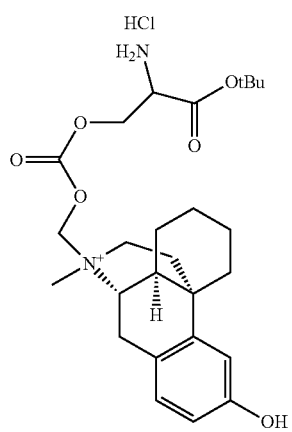
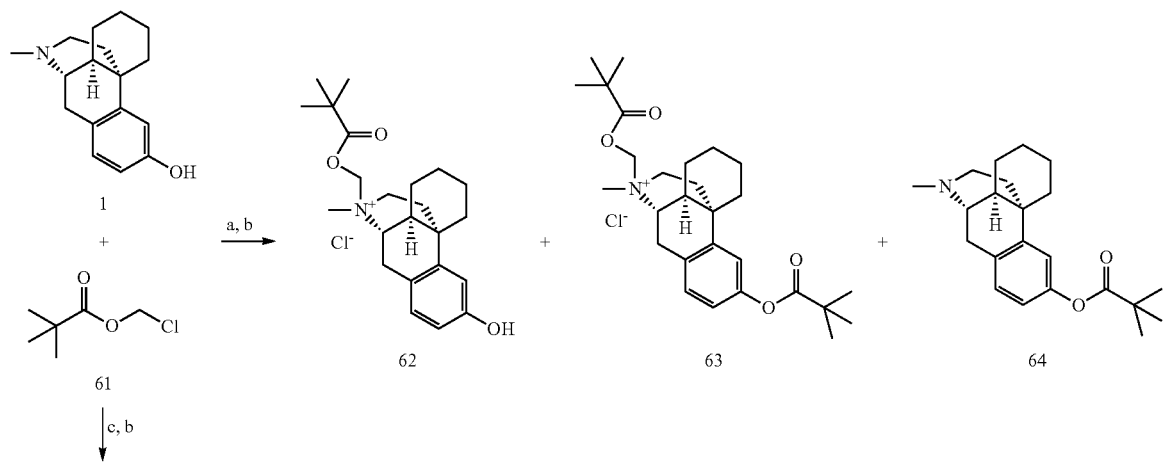

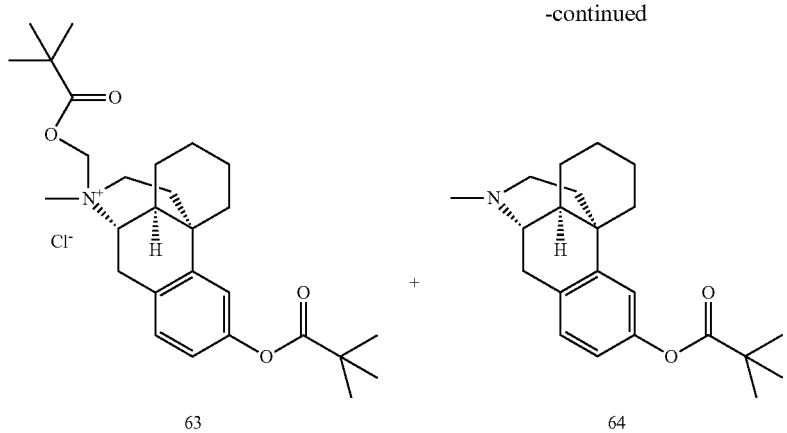

(a) CH₃CN, heat; (b) Dowex 1x4 chloride, water/CH₃CN; (c) 1,2,2,6,6-Pentamethylpiperidine CH₃CN, heat.

N-(pivaloyl-OCH₂)-dextrorphanium Chloride 62, 3-pivaloyl-N-(pivaloyl-OCH₂)-dextrorphanium Chloride 63 and 3-pivaloyl-dextrorphan 64

A suspension of dextrorphan 1 and chloromethyl pivalate 61 in CH₃CN is heated. Solvent is evaporated under reduced pressure. The quaternary salts, after separation, is treated with Dowex 1x4 chloride form, is filtered and the filtrate is lyophilized to afford compound 62 and 63. In addition, 3-monosubstituted dextrorphan conjugate 64 may form.

3-pivaloyl-N-(pivaloyl-OCH₂)-dextrorphanium Chloride 63 and 3-pivaloyl-dextrorphan 64

In an alternative reaction scheme, a mixture of dextrorphan 1, 1,2,2,6,6-pentamethyl piperidine and chloromethyl pivalate 61 in CH₃CN is heated. Solvent is evaporated under reduced pressure. The quaternary salt is treated with Dowex 1x4 chloride form and is lyophilized to give compound 63. In addition, 3-monosubstituted dextrorphan conjugate 64 may form.

Scheme 11.

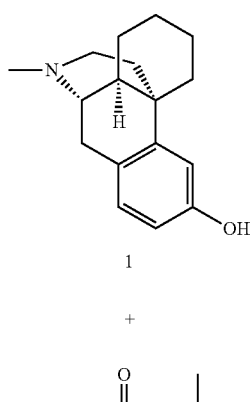

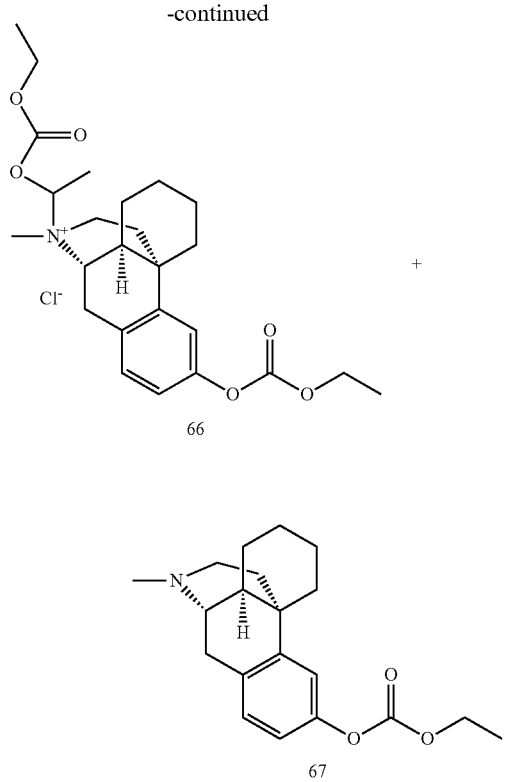

a 1,2,2,6,6-Pentamethylpiperidine CH₃CN, heat;
b Dowex 1 × 4 chloride, water/CH₃CN

3-(Ethoxy-C(O))—N-(ethoxy-C(O)CH(CH₃))-dextrorphanium chloride 66 and 3-(ethoxy-C(O))-dextrorphan 67

A mixture of dextrorphan 1, 1-chloroethyl ethyl carbonate 65, 1,2,2,6,6-pentamethylpiperidine and NaI in CH₃CN is heated. Solvent is evaporated under reduced pressure. The quaternary salt is treated with Dowex 1x4 chloride form, is filtered and the filtrate is lyophilized to give compound 66. In addition, 3-monosubstituted dextrorphan conjugate 67 may form.

49
Prophetic Synthesis of Boc-Phe-CH(Me)-COOH

50
Prophetic Synthesis of Nicotinoyl-O—CH$_2$—Cl

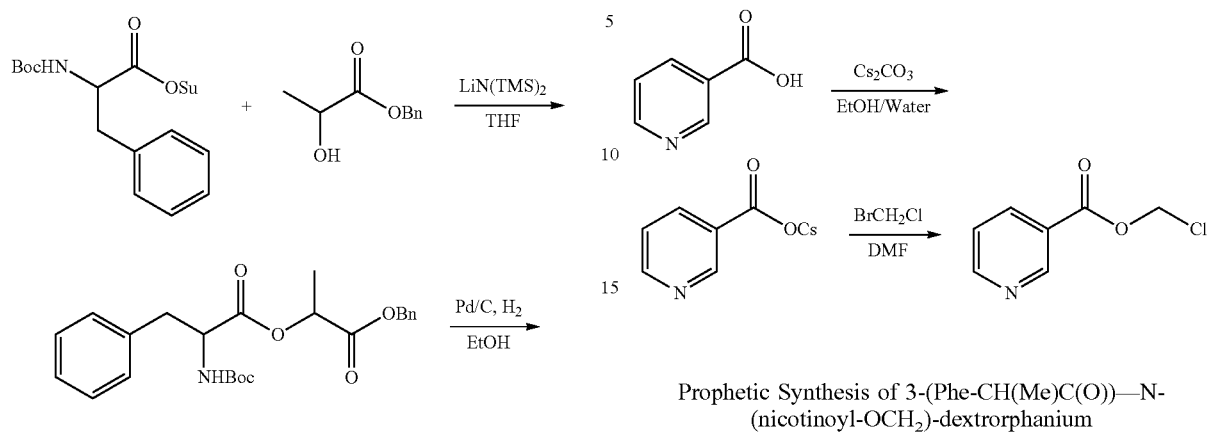

Prophetic Synthesis of 3-(Phe-CH(Me)C(O))—N-(nicotinoyl-OCH$_2$)-dextrorphanium

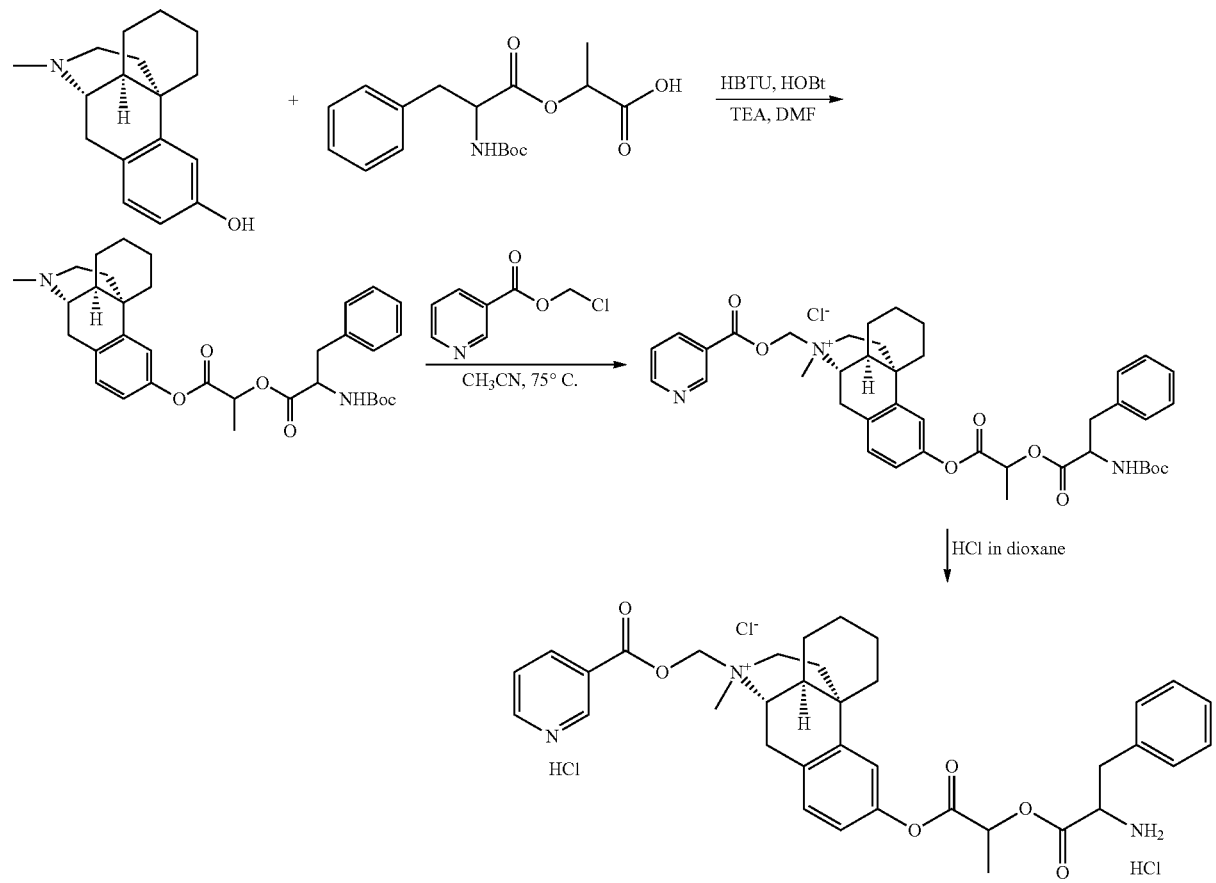

-continued

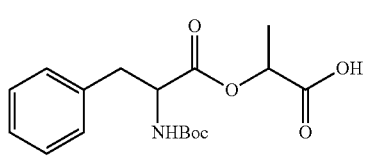

The presently described technology and its advantages will be better understood by reference to the following examples. These examples are provided to describe specific embodiments of the present technology. By providing these specific examples, it is not intended limit the scope and spirit of the present technology. It will be understood by those skilled in the art that the full scope of the presently described technology encompasses the subject matter defined by the claims appending this specification, and any alterations, modifications, or equivalents of those claims.

EXAMPLES

Example 1: Synthesis of 3-Val-dextrorphan 6

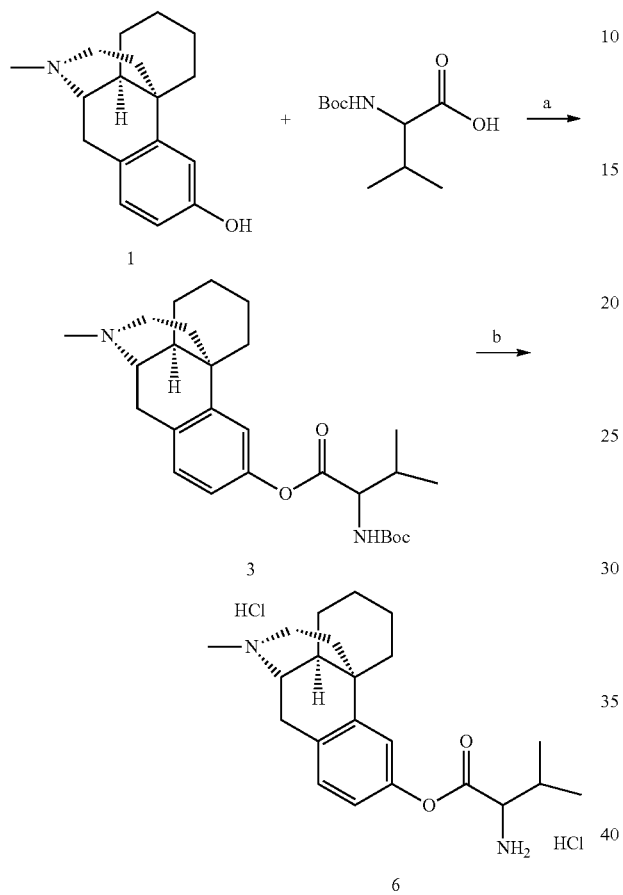

a BOP, HOBt, TEA, DMF;
b 4N HCl/dioxane.

To a solution of dextrorphan 1 (0.13 g, 0.505 mmol), Boc-Val-OH (0.12 g, 0.55 mmol), HOBt (0.072 g, 0.53 mmol) and trimethylamine (0.175 mL, 1.26 mmol) in DMF (7 mL) was added a solution of BOP (0.235 g, 0.53 mmol) in DMF (3 mL) at 0° C. After the addition, the reaction mixture was stirred overnight at room temperature. The reaction was quenched with water (1 mL) and the solvent was evaporated under reduced pressure. The residue was taken in EtOAc (100 mL), washed with 5% aq. NaHCO$_3$ (1×70 mL), 10% aq. NH$_4$Cl (1×60 mL) and brine (1×60 mL). The organic layer was dried over anhydrous Na$_2$SO$_4$ and evaporated to dryness. The solid residue was purified by preparative HPLC to give 3-(Boc-Val)-dextrorphan 3.

3-(Boc-Val)-dextrorphan 3 was dissolved in dioxane (3 mL) and to the solution was added 4N HCl in dioxane (9 mL). The reaction mixture was stirred at room temperature for 3 hours. The solvent was evaporated under reduced pressure, the residue was co-evaporated with IPAc and dried to give 3-Val-dextrorphan 6 as a white to off-white solid in 75% yield (from dextrorphan).

Example 2: Synthesis of 3-(N-acetyl-Val)-dextrorphan 68

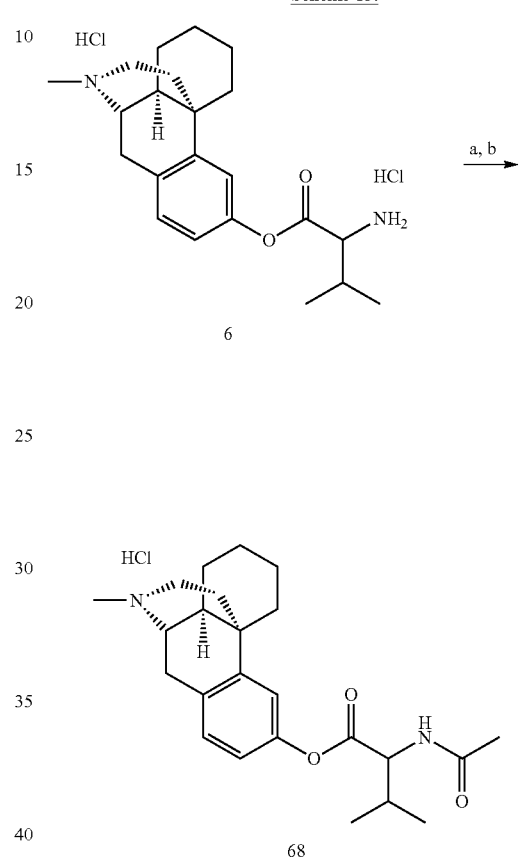

a AcCl, TEA, CH$_2$Cl$_2$;
b 2N HCl/dioxane.

A solution of 3-Val-dextrorphan 6 (0.095 g, 0.22 mmol) and TEA (0.18 mL, 1.32 mmol) in CH$_2$Cl$_2$ (5 mL) was cooled down to 0-5° C. and a solution of acetyl chloride (0.062 mL, 0.88 mmol) in CH$_2$Cl$_2$ (1 mL) was added dropwise. After the addition of acetyl chloride, the reaction mixture was stirred at 0° C. for 1.5 hours. Solvent was evaporated under reduced pressure and the residue was purified by preparative HPLC to give 3-(N-acetyl-Val)-dextrorphan.

To a solution of 3-(N-acetyl-Val)-dextrorphan in dioxane (2 mL) was added 4N HCl in dioxane (2 mL). The solution was stirred at room temperature for 10 minutes and then evaporated to dryness under vacuum to give the hydrochloride salt 68 as waxy solid (0.054 g, 56% yield)

Example 3: Synthesis of 3-(N-acetyl-Val-OCH$_2$OC(O))-dextrorphan 41

Scheme 14.

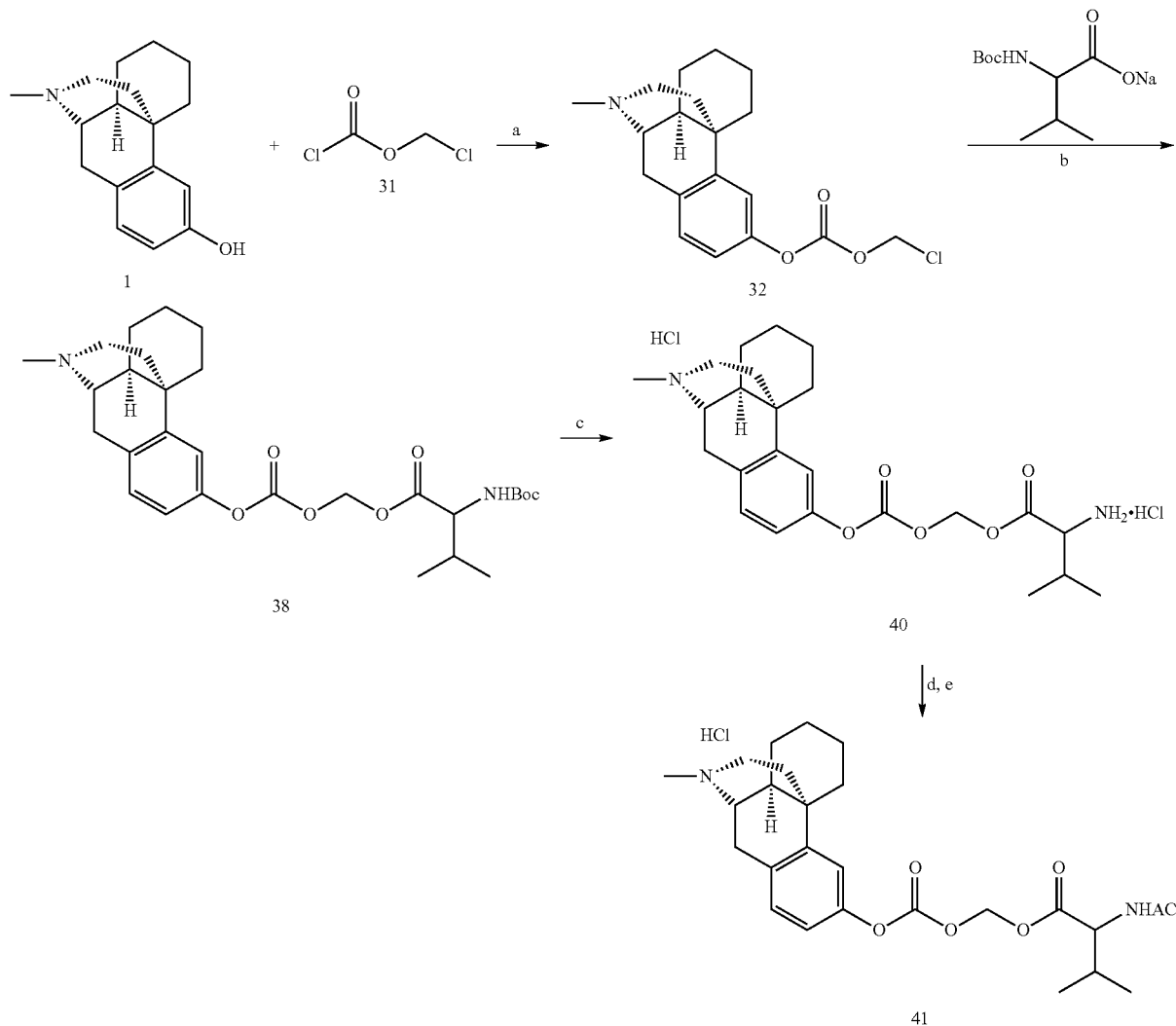

a TEA, CH$_2$Cl$_2$, 0-5° C.;
b 7, DMF, 60° C.; (c) 3-4N HCl/dioxane;
d acetyl chloride, TEA, CH$_2$Cl$_2$;
e N HCl/dioxane.

3-(Boc-Val-OCH$_2$OC(O))-dextrorphan 38

A solution of chloromethyl chloroformate 31 (0.135 mL, 1.5 mmol) in CH$_2$Cl$_2$ (2 mL) was added to a solution of dextrorphan 1 (0.258 g, 1 mmol) and trimethylamine (0.42 mL, 3 mmol) in CH$_2$Cl$_2$ (8 mL) at 0-5° C. After the addition, the reaction mixture was stirred for 1 hour at 0-5° C. The reaction was quenched with water and solvents were evaporated under reduced pressure. The residue was taken in EtOAc (100 mL), washed with 5% aq. NaHCO$_3$ (1×70 mL), brine (1×70 mL), dried over anhydrous Na$_2$SO$_4$ and evaporated to dryness to give 3-(chloromethyloxycarbonyl)-dextrorphan 32. The crude product was used in the next reaction without further purification.

A solution of 3-(chloromethyloxycarbonyl)-dextrorphan 32 (0.35 g, 1 mmol) and Boc-Val-ONa (0.36 g, 1.5 mmol) in DMF (10 mL) was heated for 2 hours at 60° C. Solvent was evaporated under reduced pressure. The residue was taken in EtOAc (110 mL), washed with 5% aq. NaHCO$_3$ (2×75 mL) and brine (1×75 mL). The organic layer was dried over anhydrous Na$_2$SO$_4$ and evaporated to dryness. The crude product was purified by preparative HPLC to give 3-(Boc-Val-OCH$_2$OC(O))-dextrorphan 38 (0.23 g, 43%).

3-(N-acetyl-Val-OCH$_2$OC(O))-dextrorphan 41

To a solution of 3-(Boc-Val-OCH$_2$OC(O))-dextrorphan 38 (0.23 g) in dioxane (2 mL) was added 4N HCl in dioxane (8 mL) and the solution was stirred for 3 hours at room temperature. Solvent was evaporated under reduced pressure, the residue was co-evaporated with IPAc and dried to give 3-(Val-OCH$_2$OC(O))-dextrorphan 40 in quantitative yield.

A solution of acetyl chloride (0.085 mL, 1.2 mmol) in CH₂Cl₂ (1 mL) was added dropwise to a solution of 3-(Val-OCH₂OC(O))-dextrorphan 40 (0.15 g, 0.3 mmol) and TEA (0.25 mL, 1.8 mmol) in CH₂Cl₂ (8 mL) at 0° C. The reaction mixture was stirred for 2 hours at 0° C. Solvents were evaporated under reduced pressure and the crude product was purified by preparative HPLC to give 3-(N-acetyl-Val-OCH₂OC(O))-dextrorphan.

The purified product was dissolved in dioxane (1.5 mL) and to the solution was added 4N HCl in dioxane (4.5 mL). The solution was stirred for 10 minutes and evaporated to dryness under vacuum to give the hydrochloride salt 41. (0.08 g, 56%).

Example 4: Synthesis of 3-Acetyl-N-(acetyl-OCH₂)-dextrorphanium 59

Example 5: Synthesis of N-(Acetyl-OCH₂)-dextrorphanium 60

A solution of dextrorphan 1 (0.077 g, 0.3 mmol) and acetyloxymethyl bromide 58 (0.06 mL, 0.6 mmol) in CH₃CN (8 mL) was heated for 1 hour at 70° C. The solution was cooled down to room temperature and solvent was evaporated under reduced pressure. The crude product was purified by preparative HPLC. The purified quaternary salt was dissolved in 4N HCl in dioxane and stirred at room temperature for 20 minutes. The solvent was evaporated, the residue was co-evaporated with IPAc and dried to give the chloride salt 60 (0.065 g, 59%) as white solid.

Scheme 8.

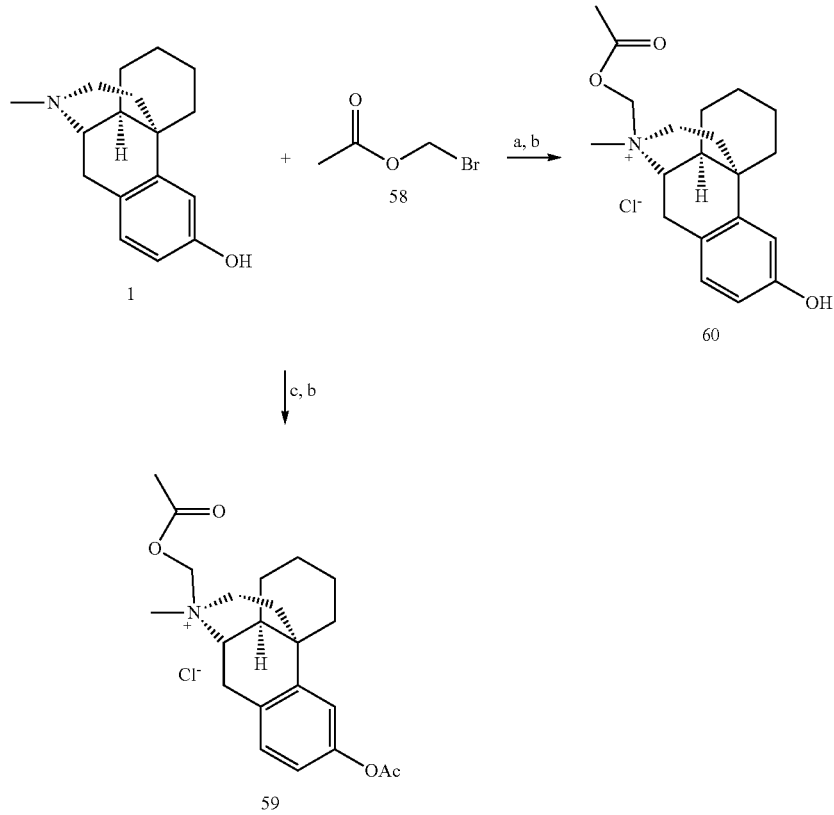

a CH₃CN, 70° C.;
b 4N HCl/dioxane;
c 1,2,2,6,6-Pentamethylpiperidine CH₃CN, 70° C.

A solution of dextrorphan 1 (0.08 g, 0.31 mmol), 1,2,2,6,6-pentaethylpiperidine (0.14 mL, 0.77 mmol) and acetyloxymethyl bromide 58 (0.076 mL, 0.77 mmol) in CH₃CN was heated for 1.5 hours at 70° C. Solvents were evaporated under reduced pressure and the residue was purified by preparative HPLC. The purified quaternary salt was dissolved in 4N HCl in dioxane and stirred for 20 minutes at room temperature. The solvent was evaporated, the residue was co-evaporated with IPAc and dried to give the chloride salt 59 (0.095 g, 75%).

Example 6: Comparison of Oral PK Profiles of Conjugates of Dextrorphan in Rats Conjugates of dextrorphan and dextrorphan tartrate comparator compound were dissolved in an appropriate vehicle and administered in rats via oral gavage. A summary of the doses and vehicles used for each compound is provided in Table 1. Whole blood samples were collected via retroorbital bleeding at 0.25, 0.5, 1, 2, 3, and 4 hours postdose. Blood samples were centrifuged and the resulting plasma samples were collected for analysis of dextrorphan concentrations by LC-MS/MS. PK profiles comparing the plasma concentrations of dextrorphan released from the conjugates and from the dextrorphan tartrate comparator are shown in FIGS. 13-16.

Figure 17:
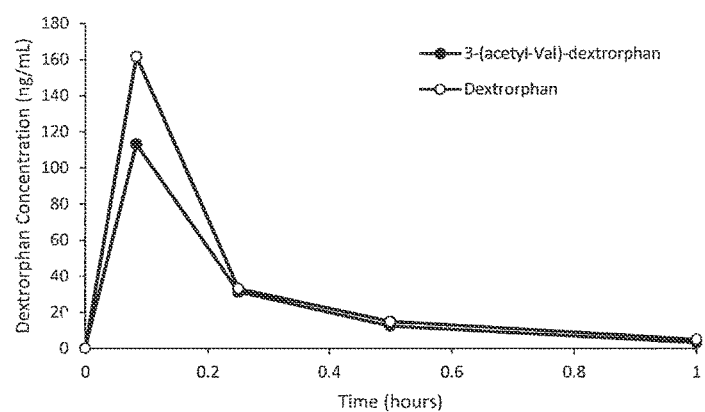
FIG. 17. Intranasal PK curves comparing 3-(N-acetyl-Val)-dextrorphan conjugate with unconjugated dextrorphan in rats.

Example 7: Comparison of Intranasal PK Profiles of Dextrorphan Conjugate and Unconjugated Dextrorphan in Rats 3-(N-acetyl-Val)-dextrorphan HCl conjugate and dextrorphan tartrate comparator compound were dissolved in an appropriate vehicle and administered in rats by slowly adding the respective dosing solution drop-wise and alternating into the nasal openings. A summary of the doses and vehicles used for each compound is provided in Table 1. Whole blood samples were collected via retro-orbital bleeding at 5 minutes and at 0.25, 0.5, and 1 hours postdose. Blood samples were centrifuged and the resulting plasma samples were collected for analysis of dextrorphan concentrations by LC-MS/MS. PK profiles comparing the plasma concentrations of dextrorphan released from the conjugate and from the dextrorphan tartrate comparator are shown in FIG. 17.

TABLE 1

| Conjugate | Conjugate Dose (mg/kg) | Comparator[a] Dose (mg/kg) | Vehicle[b] | ROA[c] |
|---|---|---|---|---|
| 3-(N-acetyl-Val)-dextrorphan HCl | 6.41 | 6.00 | Water | Oral |
| 3-(N-acetyl-Val-OCH$_2$OC(O))-dextrorphan HCl | 7.50 | 6.00 | Water | Oral |
| 3-Val-dextrorphan 2HCl | 6.32 | 6.00 | Water | Oral |
| N-(acetyl-OCH$_2$)-dextrorphanium Cl | 5.39 | 6.00 | Water | Oral |
| 3-acetyl-N-(acetyl-OCH$_2$)-dextrorphanium Cl | 6.01 | 6.00 | Water | Oral |
| 3-(N-acetyl-Val)-dextrorphan HCl | 0.21 | 0.20 | Water | Intranasal |

[a]comparator = dextrorphan tartrate; the comparator and conjugate doses are equimolar
[b]the same vehicle was used for conjugate and comparator
[c]ROA = route of administration In the present specification, use of the singular includes the plural except where specifically indicated.

The compounds, compositions, prodrugs, and methods described herein can be illustrated by the following embodiments enumerated in the numbered paragraphs that follow:

1. A compound or composition comprising at least one conjugate of dextrorphan having the following general formula:

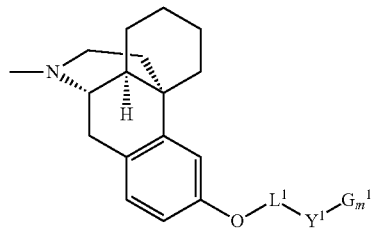

where $L^1$ is absent, or is

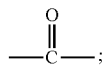

$Y^1$ is absent, or $[A\text{-}X\text{—}Z]_n$
where A, X, Z are independently absent or selected from —O—, —S— or —(CR$^1$R$^2$)$_k$—
$R^1$, $R^2$ are each independently selected from H, alkyl, aryl, alkylaryl, alkoxy, haloalkyl, or haloaryl
n and k are independently 1-4
$G_m^1$ is absent or selected independently for each repeating subunit from H, oxoacid, polyethylene glycol having from 2 to 5 ethylene oxide units, or a vitamin compound, and m is 1-4, except m is 1 when $G^1$ is H;
or a pharmaceutically acceptable salt thereof.

2. The compound or composition of paragraph 1, wherein $L^1$ and $Y^1$ are absent, $G^1$ is at least one oxoacid, and m is 1-3.

3. The compound or composition of paragraph 1, wherein $L^1$ and $Y^1$ are present, $G^1$ is at least one oxoacid, and m is 1-3.

4. The compound or composition of paragraph 1, 2 or 3, wherein $G^1$ is at least one oxoacid selected from the group consisting of aliphatic carboxylic acid, aryl carboxylic acid, dicarboxylic acid, and polycarboxylic acid.

5. The compound or composition of paragraph 1, 2 or 3, wherein $G^1$ is at least one oxoacid selected from standard amino acids, non-standard amino acids, synthetic amino acids, and combinations thereof.

6. The compound or composition of paragraph 1, 2 or 3, wherein $G^1$ is a combination of at least one oxoacid selected from the group consisting of aliphatic carboxylic acid, aryl carboxylic acid, dicarboxylic acid, and polycarboxylic acid and at least one oxoacid selected from standard amino acids, non-standard amino acids, synthetic amino acids, and combinations thereof.

7. The compound or composition of paragraph 5 or 6, wherein the at least one amino acid is a standard amino acid.

8. The compound or composition of paragraph 5 or 6, wherein the at least one amino acid is a non-standard amino acid.

9. The compound or composition of paragraph 5 or 6, wherein the at least one amino acid is a synthetic amino acid.

10. The compound or composition of paragraph 5 or 6, wherein the at least one amino acid is valine.

11. The compound or composition of paragraph 4 or 6, wherein the carboxylic acid is an aliphatic carboxylic acid selected from the group consisting of saturated carboxylic acids, monounsaturated carboxylic acids, polyunsaturated carboxylic acids, acetylenic carboxylic acids, substituted carboxylic acids, heteroatom containing carboxylic acids and ring containing carboxylic acids.

12. The compound or composition of paragraph 11, wherein the saturated carboxylic acid is selected from the group consisting of methanoic, ethanoic, propanoic, butanoic, pentanoic, hexanoic, heptanoic, octanoic, 2-propylpentanoic acid, pivalic acid, nonanoic, decanoic, dodecanoic, tetradecanoic, hexadecanoic, heptadecanoic, octadecanoic, and eicosanoic acid.

13. The compound or composition of paragraph 11, wherein the monounsaturated carboxylic acid is selected from the group consisting of 4-decenoic, 9-decenoic, 5-lauroleic, 4-dodecenoic, 9-dodecenoic, 5-tetradecenoic, 4-tetradecenoic, 9-hexadecenoic, 6-hexadecenoic, 6-octadecenoic, and 9-octadecenoic acid.

14. The compound or composition of paragraph 11, wherein the polyunsaturated carboxylic acid is selected from the group consisting of sorbic, octadecadienoic, octadecatrienoic, octadecatetraenoic, eicosatrienoic, eicosatetraenoic, eicosapentaenoic, docosapentaenoic, and docosahexaenoic acids.

15. The compound or composition of paragraph 11, wherein the acetylenic carboxylic acid is selected from the group consisting of octadecynoic, octadecenynoic, 6,9-octadecenynoic, heptadecenynoic, tridecatetraenediynoic, tridecadienetriynoic, octadecadienediynoic, heptadecadienediynoic, octadecadienediynoic, octadecenediynoic, and octadecenetriynoic acids.

16. The compound or composition of paragraph 11, wherein the substituted carboxylic acid is selected from the group consisting of methylpropanoic, isovaleric, methylhexadecanoic, 8-methyl-6-nonenoic, methyloctadecanoic, trimethyloctacosanoic, trimethyltetracosenoic, heptamethyltriacontanoic, tetramethylhexadecanoic, tetramethylpentadecanoic, lactic, glyceric, glycolic, threonic, 3-hydroxypropionic, hydroxyoctadecatrienoic, hydroxyoctadecenoic, hydroxytetracosanoic, 2-hydroxybutyric, 3-hydroxybutyric, 4-hydroxybutyric, 4-hydroxypentanoic, hydroxyoctadecadienediynoic, hydroxyoctadecadienoic, 10-hydroxydecanoic, hydroxydecenoic, hydroxyeicosenoic, hydroxyeicosadienoic, hydroxyhexadecanoic, dihydroxytetracosenoic, dihydroxydocosanoic, hydroxydocosanoic, trihydroxyoctadecanoic, trihydroxyhexadecanoic, trihydroxyicosahexaenoic, trihydroxyicosapentaenoic, 2-methoxy-5-hexadecenoic, 2-methoxy hexadecanoic, 7-methoxy-4-tetradecenoic, 9-methoxypentadecanoic, 11-methoxyheptadecanoic, 3-methoxydocosanoic, diacetoxydocosanoic, 2-acetoxydocosanoic, 2-acetoxytetracosanoic, 2-acetoxyhexacosanoic, 9-oxononanoic, oxodecanoic, oxododecenoic, hydroxyoxodecenoic, 10-oxo-8-decenoic, fluorooctadecenoic, fluorodecanoic, fluorotetradecanoic, fluorohexadecanoic, fluorooctadecadienoic, chlorohydroxyhexadecanoic, chlorohydroxyoctadecanoic, dichlorooctadecanoic, 3-bromo-2-nonaenoic, 9,10-dibromooctadecanoic, 9,10,12,13-tetrabromooctadecanoic, 10-nitro-9,12-octadecadienoic, 12-nitro-9,12-octadecadienoic, 9-nitro-9-octadecenoic, 9-oxo-2-decenoic, 9-oxo-13-octadecenoic, oxooctadecatrienoic, 15-oxo-18-tetracosenoic, 17-oxo-20-hexacosenoic, and 19-oxo-22-octacosenoic acids.

17. The compound or composition of paragraph 11, wherein the heteroatom containing carboxylic acid is selected from the group consisting of 9-(1,3-nonadienoxy)-8-nonenoic, 9-(1,3,6-nonatrienoxy)-8-nonenoic, 12-(1-hexenoxy)-9,11-dodecadienoic, 12-(1,3-hexadienoxy)-9,11-dodecadienoic, 2-dodecylsulfanylacetic, 2-tetradecylsulfanylacetic, 3-tetradecylsulfanylprop-2-enoic, and 3-tetradecylsulfanylpropanoic acid.

18. The compound or composition of paragraph 11, wherein the ring containing carboxylic acid is selected from the group consisting of 10-(2-Hexylcyclopropyl)decanoic, 3-(2-[6-bromo-3,5-nondienylcyclopropyl)propanoic, 9-(2-hexadecylcyclopropylidene)non-5-enoic, 8-(2-octyl-1-cyclopropenyl)octanoic, 7-(2-octyl-1-cyclopropenyl)heptanoic, 9,10-epoxyoctadecanoic, 9,10-epoxy12-octadecenoic, 12,13-epoxy-9-octadecenoic, 14,15-epoxy-11-eicosenoic, 11-(2-cyclopenten-1-yl)undecanoic, 13-(2-cyclopenten-1-yl)tridecanoic, 13-(2-cyclopentenyl)-6-tridecenoic, 11-cyclohexylundecanoic, 13-cyclohexyltridecanoic, 7-(3,4-dimethyl-5-pentylfuran-2-yl)heptanoic, 9-(4-methyl-5-pentylfuran-2-yl)nonanoic, 4-[5]-ladderane-butanoic, 6-[5]-ladderane-hexanoic, and 6-[3]-ladderane-hexanoic acid.

19. The compound or composition of paragraph 4 or 6, wherein the carboxylic acid is an aromatic carboxylic acid.

20. The compound or composition of paragraph 19 wherein the carboxylic acid is selected from the group consisting of benzoic acid, hydroxybenzoate, heteroaryl carboxylic acid, and combinations thereof.

21. The compound or composition of paragraph 20 wherein the hydroxybenzoate is selected from the group consisting of salicylic acid, acetylsalicylic acid (aspirin), 3-hydroxybenzoic acid, 4-hydroxybenzoic acid, 6-methylsalicylic acid, o,m,p-cresotinic acid, anacardic acids, 4,5-dimethylsalicylic acid, o,m,p-thymotic acid, diflunisal, o,m,p-anisic acid, 2,3-dihydroxybenzoic acid (2,3-DHB), α,β,γ-resorcylic acid, protocatechuic acid, gentisic acid, piperonylic acid, 3-methoxysalicylic acid, 4-methoxysalicylic acid, 5-methoxysalicylic acid, 6-methoxysalicylic acid, 3-hydroxy-2-methoxybenzoic acid, 4-hydroxy-2-methoxybenzoic acid, 5-hydroxy-2-methoxybenzoic acid, vanillic acid, isovanillic acid, 5-hydroxy-3-methoxybenzoic acid, 2,3-dimethoxybenzoic acid, 2,4-dimethoxybenzoic acid, 2,5-dimethoxybenzoic acid, 2,6-dimethoxybenzoic acid, veratric acid (3,4-dimethoxybenzoic acid), 3,5-dimethoxybenzoic acid, gallic acid, 2,3,4-trihydroxybenzoic acid, 2,3,6-trihydroxybenzoic acid, 2,4,5-trihydroxybenzoic acid, 3-O-methylgallic acid (3-OMGA), 4-O-methylgallic acid (4-OMGA), 3,4-O-dimethylgallic acid, syringic acid, and 3,4,5-trimethoxybenzoic acid.

22. The compound or composition of paragraph 20 wherein the heteroaryl carboxylic acid is selected from the group consisting of nicotinic acid, isonicotinic acid, picolinic acid, 3-hydroxypicolinic acid, 6-hydroxynicotinic acid, citrazinic acid, 2,6-dihydroxynicotinic acid, kynurenic acid, xanthurenic acid, 6-hydroxykynurenic acid, 8-methoxykynurenic acid, 7,8-dihydroxykynurenic acid, and 7,8-dihydro-7,8-dihydroxykynurenic acid.

23. The compound or composition of paragraph 19, wherein the aromatic carboxylic acid is a phenylacetate selected from the group consisting of phenylacetic acid (hydratropic acid), 2-hydroxyphenylacetic acid, 3-hydroxyphenylacetic acid, 4-hydroxyphenylacetic acid, homoprotocatechuic acid, homogentisic acid, 2,6-dihydroxyphenylacetic acid, homovanillic acid, homoisovanillic acid, homoveratric acid, atropic acid, d,l-tropic acid, diclofenac, d,l-mandelic acid, 3,4-dihydroxy-d,l-mandelic acid, vanillyl-d,l-mandelic acid, isovanillyl-d,l-mandelic acid, ibuprofen, fenoprofen, carprofen, flurbiprofen, ketoprofen, and naproxen.

24. The compound or composition of paragraph 19, wherein the aromatic carboxylic acid is a benzylacetate selected from the group consisting of benzylacetic acid, melilotic acid, 3-hydroxyphenylpropanoic acid, 4-hydroxyphenylpropanoic acid, 2,3-dihydroxyphenylpropanoic acid, d,l-phenyllactic acid, o,m,p-hydroxy-d,l-phenyllactic acid, and phenylpyruvic acid.

25. The compound or composition of paragraph 19, wherein the aromatic carboxylic acid is a cinnamate, selected from the group consisting of cinnamic acid, o,m,p-coumaric acid, 2,3-dihydroxycinnamic acid, 2,6-dihydroxycinnamic acid, caffeic acid, ferulic acid, isoferulic acid, 5-hydroxyferulic acid, sinapic acid, and 2-hydroxy-3-phenylpropenoic acid.

26. The compound or composition of paragraph 4 or 6, wherein the carboxylic acid is a dicarboxylic acid of the general formula HOOC—R—COOH, where R is selected from the group consisting of an alkyl, alkenyl, alkynyl, aryl group, and derivatives thereof.

27. The compound or composition of paragraph 26, wherein the dicarboxylic acid is selected from the group consisting of oxalic, malonic, succinic, glutaric, adipic, pimelic, suberic, azelaic, sebacic, brassylic, thapsic, malic, tartaric, dihydroxymesoxalic, α-hydroxyglutaric, methylmalonic, meglutol, diaminopimelic, carbamoyl aspartic, fumaric, maleic, mesaconic, 3-methylglutaconic, traumatic, phthalic acid, isophthalic, terephthalic, and dipicolinic acid.

28. The compound or composition of paragraph 4 or 6, wherein the carboxylic acid is a polycarboxylic acid selected from the group consisting of citric acid, isocitric, carballylic, and trimesic acid.

29. The compound or composition of paragraph 1, wherein $G^1$ is at least one polyethylene glycol.

30. The compound or composition of paragraph 29, wherein the terminal hydroxyl group of the polyethylene glycol is substituted with an amino, azide, or methoxy group.

31. The compound or composition of paragraph 1, wherein $L^1$ and $Y^1$ are absent, $G^1$ is at least one vitamin compound, and m is 1-3.

32. The compound or composition of paragraph 1 or 31 wherein the at least one vitamin compound is selected from ascorbic acid, riboflavin, thiamin, pantothenic acid, pyridoxine, pyridoxamine, pyridoxal, biotin, folic acid, niacin, pantothenic acid, retinol, cholecalciferol, ergocalciferol, and tocopherols.

33. The compound or composition of paragraph 1, wherein the at least one conjugate of dextrorphan comprises 3-(N-acetyl-Val)-dextrorphan having the following structural formula, or a pharmaceutically acceptable salt thereof:

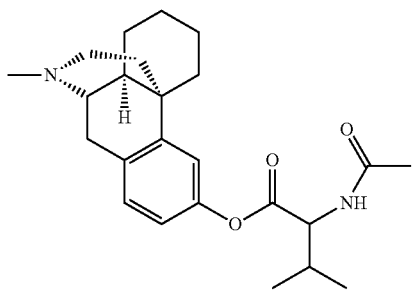

34. The compound or composition of paragraph 1 wherein the at least one conjugate of dextrorphan comprises 3-(N-acetyl-Val-OCH$_2$OC(O))-dextrorphan having the following structural formula, or a pharmaceutically acceptable salt thereof:

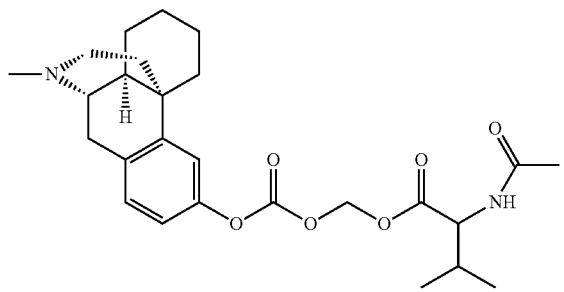

35. The compound or composition of paragraph 1 wherein the at least one conjugate of dextrorphan comprises 3-Val-dextrorphan having the following structure, or a pharmaceutically acceptable salt thereof:

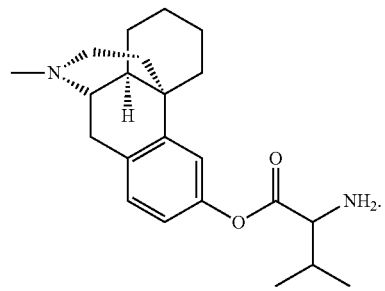

36. A compound or composition comprising at least one conjugate of dextrorphan having the following general formula:

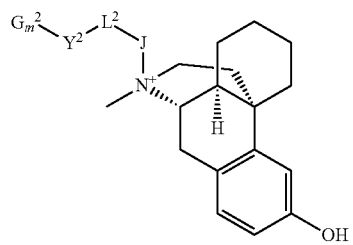

where $L^2$ is absent, or is

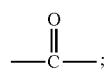

$Y^2$ is absent, or $[A-X-Z]_n$
where A, X, Z are independently absent or selected from
—O—, —S— or —(CR$^1$R$^2$)$_k$—
J is $[M-W]_p$
where M is absent, or —(CR$^3$R$^4$)$_q$—; and W is absent, or —O— or —S—
$R^1$, $R^2$, $R^3$, $R^4$ are each independently selected from H, alkyl, aryl, alkylaryl, alkoxy, haloalkyl, or haloaryl
n and k are independently 1-4
p and q are independently 1-4
$G_m^2$ is absent or selected independently for each repeating subunit from H, oxoacid, polyethylene glycol having from 2 to 5 ethylene oxide units, or a vitamin compound, and m is 1-4, except m is 1 when $G^2$ is H;
or a pharmaceutically acceptable salt thereof.

37. The compound or composition of paragraph 36, wherein $G^2$ is at least one oxoacid, and m is 1-3.

38. The compound or composition of paragraph 37, wherein the at least one oxoacid is at least one carboxylic acid is selected from the group consisting of aliphatic carboxylic acid, aryl carboxylic acid, dicarboxylic acid, polycarboxylic acid, and combinations thereof.

39. The compound or composition of paragraph 37, wherein the oxoacid is at least one amino acid selected from standard amino acids, non-standard amine acids, synthetic amino acids, and combinations thereof.

40. The compound or composition of paragraph 37, wherein the at least one oxoacid is a combination of at least one carboxylic acid selected from the group consisting of aliphatic carboxylic acid, aryl carboxylic acid, dicarboxylic acid, polycarboxylic acid, and combinations thereof, and at least one amino acid selected from the group consisting of standard amino acids, non-standard amine acids, synthetic amino acids, and combinations thereof.

41. The compound or composition of paragraph 38 or 40, wherein the carboxylic acid is an aliphatic carboxylic acid selected from the group consisting of saturated carboxylic acids, monounsaturated carboxylic acids, polyunsaturated carboxylic acids, acetylenic carboxylic acids, substituted carboxylic acids, heteroatom containing carboxylic acids and ring containing carboxylic acids.

42. The compound or composition of paragraph 41, wherein the saturated carboxylic acid is selected from the group consisting of methanoic, ethanoic, propanoic, butanoic, pentanoic, hexanoic, heptanoic, octanoic, 2-propylpentanoic acid, pivalic acid, nonanoic, decanoic, dodecanoic, tetradecanoic, hexadecanoic, heptadecanoic, octadecanoic, and eicosanoic acid.

43. The compound or composition of paragraph 41, wherein the monounsaturated carboxylic acid is selected from the group consisting of 4-decenoic, 9-decenoic, 5-lauroleic, 4-dodecenoic, 9-tetradecenoic, 5-tetradecenoic, 4-tetradecenoic, 9-hexadecenoic, 6-hexadecenoic, 6-octadecenoic, and 9-octadecenoic acid.

44. The compound or composition of paragraph 41, wherein the polyunsaturated carboxylic acid is selected from the group consisting of sorbic, octadecadienoic, octadecatrienoic, octadecatetraenoic, eicosatrienoic, eicosatetraenoic, eicosapentaenoic, docosapentaenoic, and docosahexaenoic acids.

45. The compound or composition of paragraph 41, wherein the acetylenic carboxylic acid is selected from the group consisting of octadecynoic, octadecenynoic, 6,9-octadecenynoic, heptadecenynoic, tridecatetraenediynoic, tridecadienetriynoic, octadecadienediynoic, heptadecadienediynoic, octadecadienediynoic, octadecenediynoic, and octadecenetriynoic acids.

46. The compound or composition of paragraph 41, wherein the substituted carboxylic acid is selected from the group consisting of methylpropanoic, isovaleric, methylhexadecanoic, 8-methyl-6-nonenoic, methyloctadecanoic, trimethyloctacosanoic, trimethyltetracosenoic, heptamethyltriacontanoic, tetramethylhexadecanoic, tetramethylpentadecanoic, lactic, glyceric, glycolic, threonic, 3-hydroxypropionic, hydroxyoctadecatrienoic, hydroxyoctadecenoic, hydroxytetracosanoic, 2-hydroxybutyric, 3-hydroxybutyric, 4-hydroxybutyric, 4-hydroxypentanoic, hydroxyoctadecadienediynoic, hydroxyoctadecadienoic, 10-hydroxydecanoic, hydroxydecenoic, hydroxyeicosenoic, hydroxyeicosadienoic, hydroxyhexadecanoic, dihydroxytetracosenoic, dihydroxydocosanoic, hydroxydocosanoic, trihydroxyoctadecanoic, trihydroxyhexadecanoic, trihydroxyicosahexaenoic, trihydroxyicosapentaenoic, 2-methoxy-5-hexadecenoic, 2-methoxy hexadecanoic, 7-methoxy-4-tetradecenoic, 9-methoxypentadecanoic, 11-methoxyheptadecanoic, 3-methoxydocosanoic, diacetoxydocosanoic, 2-acetoxydocosanoic, 2-acetoxytetracosanoic, 2-acetoxyhexacosanoic, 9-oxononanoic, oxodecanoic, oxododecenoic, hydroxyoxodecenoic, 10-oxo-8-decenoic, fluorooctadecenoic, fluorodecanoic, fluorotetradecanoic, fluorohexadecanoic, fluorooctadecadienoic, chlorohydroxyhexadecanoic, chlorohydroxyoctadecanoic, dichlorooctadecanoic, 3-bromo-2-nonaenoic, 9,10-dibromooctadecanoic, 9,10,12,13-tetrabromooctadecanoic, 10-nitro-9,12-octadecadienoic, 12-nitro-9,12-octadecadienoic, 9-nitro-9-octadecenoic, 9-oxo-2-decenoic, 9-oxo-13-octadecenoic, oxooctadecatrienoic, 15-oxo-18-tetracosenoic, 17-oxo-20-hexacosenoic, and 19-oxo-22-octacosenoic acids.

47. The compound or composition of paragraph 41, wherein the heteroatom containing carboxylic acid is selected from the group consisting of 9-(1,3-nonadienoxy)-8-nonenoic, 9-(1,3,6-nonatrienoxy)-8-nonenoic, 12-(1-hexenoxy)-9,11-dodecadienoic, 12-(1,3-hexadienoxy)-9,11-dodecadienoic, 2-dodecylsulfanylacetic, 2-tetradecylsulfanylacetic, 3-tetradecylsulfanylprop-2-enoic, and 3-tetradecylsulfanylpropanoic acid.

48. The compound or composition of paragraph 41, wherein the ring containing carboxylic acid is selected from the group consisting of 10-(2-Hexylcyclopropyl)decanoic, 3-(2-[6-bromo-3,5-nondienylcyclopropyl)propanoic, 9-(2-hexadecylcyclopropylidene)non-5-enoic, 8-(2-octyl-1-cyclopropenyl)octanoic, 7-(2-octyl-1-cyclopropenyl)heptanoic, 9,10-epoxyoctadecanoic, 9,10-epoxy12-octadecenoic, 12,13-epoxy-9-octadecenoic, 14,15-epoxy-11-eicosenoic, 11-(2-cyclopenten-1-yl)undecanoic, 13-(2-cyclopenten-1-yl)tridecanoic, 13-(2-cyclopentenyl)-6-tridecenoic, 11-cyclohexylundecanoic, 13-cyclohexyltridecanoic, 7-(3,4-dimethyl-5-pentylfuran-2-yl)heptanoic, 9-(4-methyl-5-pentylfuran-2-yl)nonanoic, 4-[5]-ladderanebutanoic, 6-[5]-ladderane-hexanoic, and 6-[3]-ladderanehexanoic acid.

49. The compound or composition of paragraph 38 or 40, wherein the carboxylic acid is an aromatic carboxylic acid.

50. The compound or composition of paragraph 49, wherein the aromatic carboxylic acid is selected from the group consisting of benzoic acid, hydroxybenzoate, heteroaryl carboxylic acid, and combinations thereof.

51 The compound or composition of paragraph 50, wherein the hydroxybenzoate is selected from the group consisting of salicylic acid, acetylsalicylic acid (aspirin), 3-hydroxybenzoic acid, 4-hydroxybenzoic acid, 6-methylsalicylic acid, o,m,p-cresotinic acid, anacardic acids, 4,5-dimethylsalicylic acid, o,m,p-thymotic acid, diflunisal, o,m, p-anisic acid, 2,3-dihydroxybenzoic acid (2,3-DHB), α,β,γ-resorcylic acid, protocatechuic acid, gentisic acid, piperonylic acid, 3-methoxysalicylic acid, 4-methoxysalicylic acid, 5-methoxysalicylic acid, 6-methoxysalicylic acid, 3-hydroxy-2-methoxybenzoic acid, 4-hydroxy-2-methoxybenzoic acid, 5-hydroxy-2-methoxybenzoic acid, vanillic acid, isovanillic acid, 5-hydroxy-3-methoxybenzoic acid, 2,3-dimethoxybenzoic acid, 2,4-dimethoxybenzoic acid, 2,5-dimethoxybenzoic acid, 2,6-dimethoxybenzoic acid, veratric acid (3,4-dimethoxybenzoic acid), 3,5-dimethoxybenzoic acid, gallic acid, 2,3,4-trihydroxybenzoic acid, 2,3,6-trihydroxybenzoic acid, 2,4,5-trihydroxybenzoic acid, 3-O-methylgallic acid (3-OMGA), 4-O-methylgallic acid (4-OMGA), 3,4-O-dimethylgallic acid, syringic acid, and 3,4,5-trimethoxybenzoic acid.

52. The compound or composition of paragraph 50, wherein the heteroaryl carboxylic acid is selected from the group consisting of nicotinic acid, isonicotinic acid, picolinic acid, 3-hydroxypicolinic acid, 6-hydroxynicotinic acid, citrazinic acid, 2,6-dihydroxynicotinic acid, kynurenic acid, xanthurenic acid, 6-hydroxykynurenic acid, 8-methoxykynurenic acid, 7,8-dihydroxykynurenic acid, and 7,8-dihydro-7,8-dihydroxykynurenic acid.

53. The compound or composition of paragraph 49, wherein the carboxylic acid is a phenylacetate, a branched phenylpropionate, an unbranched phenylpropionate (benzylacetate), a phenylpropenoate (cinnamate), salts thereof, derivatives thereof, or a combination thereof.

54. The compound or composition of paragraph 53, wherein the phenylacetate is selected from the group consisting of phenylacetic acid (hydratropic acid), 2-hydroxyphenylacetic acid, 3-hydroxyphenylacetic acid, 4-hydroxyphenylacetic acid, homoprotocatechuic acid, homogentisic acid, 2,6-dihydroxyphenylacetic acid, homovanillic acid, homoisovanillic acid, homoveratric acid, atropic acid, d,l-tropic acid, diclofenac, d,l-mandelic acid, 3,4-dihydroxy-d,l-mandelic acid, vanillyl-d,l-mandelic acid, isovanillyl-d,l-mandelic acid, ibuprofen, fenoprofen, carprofen, flurbiprofen, ketoprofen, and naproxen.

55. The compound or composition of paragraph 49, wherein the carboxylic acid is a benzylacetate selected from the group consisting of benzylacetic acid, melilotic acid, 3-hydroxyphenylpropanoic acid, 4-hydroxyphenylpropanoic acid, 2,3-dihydroxyphenylpropanoic acid, d,l-phenyllactic acid, o,m,p-hydroxy-d,l-phenyllactic acid, and phenylpyruvic acid.

56. The compound or composition of paragraph 49, wherein the carboxylic acid is a cinnamate, derivatives thereof, or combinations thereof.

57. The compound or composition of paragraph 56, wherein the cinnamate is selected from the group consisting of cinnamic acid, o,m,p-coumaric acid, 2,3-dihydroxycinnamic acid, 2,6-dihydroxycinnamic acid, caffeic acid, ferulic acid, isoferulic acid, 5-hydroxyferulic acid, sinapic acid, and 2-hydroxy-3-phenylpropenoic acid.

58. The compound or composition of paragraph 38 or 40, wherein the dicarboxylic acid is of the general formula HOOC—R—COOH, where R is selected from the group consisting of an alkyl, alkenyl, alkynyl, arylgroup, and derivatives thereof.

59. The compound or composition of paragraph 58, wherein the dicarboxylic acid is selected from the group consisting of oxalic, malonic, succinic, glutaric, adipic, pimelic, suberic, azelaic, sebacic, brassylic, thapsic, malic, tartaric, dihydroxymesoxalic, α-hydroxyglutaric, methylmalonic, meglutol, diaminopimelic, carbamoyl aspartic, fumaric, maleic, mesaconic, 3-methylglutaconic, traumatic, phthalic acid, isophthalic, terephthalic, and dipicolinic acid.

60. The compound or composition of paragraph 38 or 40, wherein the polycarboxylic acid is selected from the group consisting of citric acid, isocitric, carballylic, and trimesic acid.

61. The compound or composition of paragraph 39 or 40, wherein the amino acid is a standard amino acid.

62. The compound or composition of paragraph 39 or 40, wherein the amino acid is a non-standard amino acid or a synthetic amino acid.

63. The compound or composition of paragraph 36, wherein $G^2$ is at least one polyethylene glycol, and m is 13.

64. The compound or composition of paragraph 63, wherein the terminal hydroxyl group of the polyethylene glycol is substituted with an amino, azide, or methoxy group.

65. The compound or composition of paragraph 36, wherein $G^2$ is at least one vitamin compound, and m is 13.

66. The compound or composition of paragraph 65 wherein the at least one vitamin compound is selected from ascorbic acid, riboflavin, thiamin, pantothenic acid, pyridoxine, pyridoxamine, pyridoxal, biotin, folic acid, niacin, pantothenic acid, retinol, cholecalciferol, ergocalciferol, and tocopherols.

67. The compound or composition of paragraph 36 wherein the at least one conjugate of dextrorphan comprises N-(acetyl-OCH$_2$)-dextrorphanium having the following structural formula, or a pharmaceutically acceptable salt thereof:

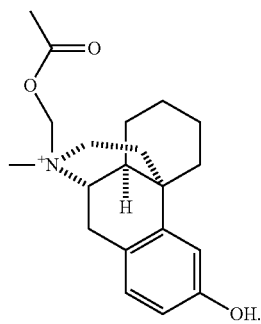

68. A compound or composition comprising at least one conjugate of dextrorphan having the following general formula:

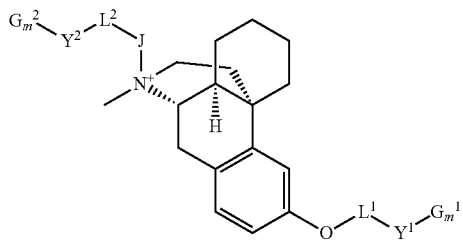

where $L^1$ and $L^2$ are independently absent, or

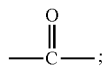

$Y^1$ and $Y^2$ are independently either absent, or $[A-X—Z]_n$ where A, X, Z are independently selected for $Y^1$ and $Y^2$, and are, independent of each other, either absent or selected from —O—, —S—, or —(CR$^1$R$^2$)$_k$—

J is $[M-W]_p$ where M is absent, or —(CR$^3$R$^4$)$_q$—; and W is absent, or —O— or —S—

$R^1$ and $R^2$ are each independently selected for $Y^1$ and $Y^2$, and are, independent of each other, selected from H, alkyl, aryl, alkylaryl, alkoxy, haloalkyl, or haloaryl $R^3$ and $R^4$ are each independently selected from H, alkyl, aryl, alkylaryl, alkoxy, haloalkyl, or haloaryl for each $Y^1$ and $Y^2$, n is independently an integer of 1-4 for each repeating unit of $[A-X—Z]_n$, when —(CR$^1$R$^2$)$_k$— is present, k is independently an integer of 1-4.

p and q are independently 1-4

$G_m^1$ and $G_m^2$ are independently absent, or selected independently of each other and, when present, each repeating subunit is independently selected from H, oxoacid, polyethylene glycol having from 2 to 5 ethylene oxide units, or a vitamin compound;

where m is selected independently for $G^1$ and $G^2$, and is an integer of 1-4, except that m is 1 when $G^1$ or $G^2$ is a hydrogen atom;

or a pharmaceutically acceptable salt thereof.

69. The compound or composition of paragraph 68, wherein $L^1$ and $Y^1$ are absent, $G^1$ is at least one oxoacid, and m is 1-3, and M is —$(CR^3R^4)_q$—; W is O or absent, $L^2$ and $Y^2$ are absent, $G^2$ is at least one oxoacid, and m is 1-3.

70. The compound or composition of paragraph 68, wherein $L^1$ and $Y^1$ are present, A is O, X is —$(CR^1R^2)_k$—, Z is O, $G^1$ is at least one oxoacid, and m is 1-3, and M is —$(CR^3R^4)_q$—; W is O or absent, $L^2$ and $Y^2$ are absent, $G^2$ is at least one oxoacid, and m is 1-3.

71. The compound or composition of paragraph 69 or 70, wherein the at least one oxoacid is at least one carboxylic acid selected from the group consisting of aliphatic carboxylic acid, aryl carboxylic acid, dicarboxylic acid, polycarboxylic acid, and combinations thereof.

72. The compound or composition of paragraph 69 or 70, wherein the at least one oxoacid is at least one amino acid selected from standard amino acids, non-standard amino acids, synthetic amino acids, and combinations thereof.

73. The compound or composition of paragraph 68, 69, or 70, wherein $G^1$ and/or $G^2$ is a combination of at least one oxoacid selected from the group consisting of aliphatic carboxylic acid, aryl carboxylic acid, dicarboxylic acid, polycarboxylic acid, and combinations thereof, and at least one amino acid selected from the group consisting of standard amino acids, non-standard amino acids, synthetic amino acids, and combinations thereof.

74. The compound or composition of paragraph 72 or 73, wherein the at least one amino acid is a standard amino acid.

75. The compound or composition of paragraph 72 or 73, wherein the at least one amino acid is a non-standard amino acid.

76. The compound or composition of paragraph 72 or 73, wherein the at least one amino acid is a synthetic amino acid.

77. The compound or composition of paragraph 72 or 73, wherein the at least one amino acid is valine.

78. The compound or composition of paragraph 71 or 73, wherein the carboxylic acid is an aliphatic carboxylic acid selected from the group consisting of saturated carboxylic acids, monounsaturated carboxylic acids, polyunsaturated carboxylic acids, acetylenic carboxylic acids, substituted carboxylic acids, heteroatom containing carboxylic acids and ring containing carboxylic acids.

79. The compound or composition of paragraph 78, wherein the saturated carboxylic acid is selected from the group consisting of methanoic, ethanoic, propanoic, butanoic, pentanoic, hexanoic, heptanoic, octanoic, 2-propylpentanoic acid, pivalic acid, nonanoic, decanoic, dodecanoic, tetradecanoic, hexadecanoic, heptadecanoic, octadecanoic, and eicosanoic acid.

80. The compound or composition of paragraph 78, wherein the monounsaturated carboxylic acid is selected from the group consisting of 4-decenoic, 9-decenoic, 5-lauroleic, 4-dodecenoic, 9-tetradecenoic, 5-tetradecenoic, 4-tetradecenoic, 9-hexadecenoic, 6-hexadecenoic, 6-octadecenoic, and 9-octadecenoic acid.

81. The compound or composition of paragraph 78, wherein the polyunsaturated carboxylic acid is selected from the group consisting of sorbic, octadecadienoic, octadecatrienoic, octadecatetraenoic, eicosatrienoic, eicosatetraenoic, eicosapentaenoic, docosapentaenoic, and docosahexaenoic acids.

82. The compound or composition of paragraph 78, wherein the acetylenic carboxylic acid is selected from the group consisting of octadecynoic, octadecenynoic, 6,9-octadecenynoic, heptadecenynoic, tridecatetraenediynoic, tridecadienetriynoic, octadecadienediynoic, heptadecadienediynoic, octadecadienediynoic, octadecenediynoic, and octadecenetriynoic acids.

83. The compound or composition of paragraph 78, wherein the substituted carboxylic acid is selected from the group consisting of methylpropanoic, isovaleric, methylhexadecanoic, 8-methyl-6-nonenoic, methyloctadecanoic, trimethyloctacosanoic, trimethyltetracosenoic, heptamethyltriacontanoic, tetramethylhexadecanoic, tetramethylpentadecanoic, lactic, glyceric, glycolic, threonic, 3-hydroxypropionic, hydroxyoctadecatrienoic, hydroxyoctadecenoic, hydroxytetracosanoic, 2-hydroxybutyric, 3-hydroxybutyric, 4-hydroxybutyric, 4-hydroxypentanoic, hydroxyoctadecadienoic, hydroxyoctadecadienoic, 10-hydroxydecanoic, hydroxydecenoic, hydroxyeicosenoic, hydroxyeicosadienoic, hydroxyhexadecanoic, dihydroxytetracosenoic, dihydroxydocosanoic, hydroxydocosanoic, trihydroxyoctadecanoic, trihydroxyhexadecanoic, trihydroxyicosahexaenoic, trihydroxyicosapentaenoic, 2-methoxy-5-hexadecenoic, 2-methoxy hexadecanoic, 7-methoxy-4-tetradecenoic, 9-methoxypentadecanoic, 11-methoxyheptadecanoic, 3-methoxydocosanoic, diacetoxydocosanoic, 2-acetoxydocosanoic, 2-acetoxytetracosanoic, 2-acetoxyhexacosanoic, 9-oxononanoic, oxodecanoic, oxododecenoic, hydroxyoxodecenoic, 10-oxo-8-decenoic, fluorooctadecenoic, fluorodecanoic, fluorotetradecanoic, fluorohexadecanoic, fluorooctadecadienoic, chlorohydroxyhexadecanoic, chlorohydroxyoctadecanoic, dichlorooctadecanoic, 3-bromo-2-nonaenoic, 9,10-dibromooctadecanoic, 9,10,12,13-tetrabromooctadecanoic, 10-nitro-9,12-octadecadienoic, 12-nitro-9,12-octadecadienoic, 9-nitro-9-octadecenoic, 9-oxo-2-decenoic, 9-oxo-13-octadecenoic, oxooctadecatrienoic, 15-oxo-18-tetracosenoic, 17-oxo-20-hexacosenoic, and 19-oxo-22-octacosenoic acids.

84. The compound or composition of paragraph 78, wherein the heteroatom containing carboxylic acid is selected from the group consisting of 9-(1,3-nonadienoxy)-8-nonenoic, 9-(1,3,6-nonatrienoxy)-8-nonenoic, 12-(1-hexenoxy)-9,11-dodecadienoic, 12-(1,3-hexadienoxy)-9,11-dodecadienoic, 2-dodecylsulfanylacetic, 2-tetradecylsulfanylacetic, 3-tetradecylsulfanylprop-2-enoic, and 3-tetradecylsulfanylpropanoic acid.

85. The compound or composition of paragraph 78, wherein the ring containing carboxylic acid is selected from the group consisting of 10-(2-Hexylcyclopropyl)decanoic, 3-(2-[6-bromo-3,5-nondienylcyclopropyl)propanoic, 9-(2-hexadecylcyclopropylidene)non-5-enoic, 8-(2-octyl-1-cyclopropenyl)octanoic, 7-(2-octyl-1-cyclopropenyl)heptanoic, 9,10-epoxyoctadecanoic, 9,10-epoxy12-octadecenoic, 12,13-epoxy-9-octadecenoic, 14,15-epoxy-11-eicosenoic, 11-(2-cyclopenten-1-yl)undecanoic, 13-(2-cyclopenten-1-yl)tridecanoic, 13-(2-cyclopentenyl)-6-tridecenoic, 11-cyclohexylundecanoic, 13-cyclohexyltridecanoic, 7-(3,4-dimethyl-5-pentylfuran-2-yl)heptanoic, 9-(4-methyl-5-pentylfuran-2-yl)nonanoic, 4-[5]-ladderanebutanoic, 6-[5]-ladderane-hexanoic, and 6-[3]-ladderanehexanoic acid.

86. The compound or composition of paragraph 71 or 73, wherein the carboxylic acid is an aromatic carboxylic acid.

87. The compound or composition of paragraph 86 wherein the carboxylic acid is selected from the group consisting of benzoic acid, hydroxybenzoate, heteroaryl carboxylic acid, and combinations thereof.

88. The compound or composition of paragraph 87 wherein the hydroxybenzoate is selected from the group consisting of salicylic acid, acetylsalicylic acid (aspirin), 3-hydroxybenzoic acid, 4-hydroxybenzoic acid, 6-methylsalicylic acid, o,m,p-cresotinic acid, anacardic acids, 4,5-dimethylsalicylic acid, o,m,p-thymotic acid, diflunisal, o,m,p-anisic acid, 2,3-dihydroxybenzoic acid (2,3-DHB), α,β,γ-resorcylic acid, protocatechuic acid, gentisic acid, piperonylic acid, 3-methoxysalicylic acid, 4-methoxysalicylic acid, 5-methoxysalicylic acid, 6-methoxysalicylic acid, 3-hydroxy-2-methoxybenzoic acid, 4-hydroxy-2-methoxybenzoic acid, 5-hydroxy-2-methoxybenzoic acid, vanillic acid, isovanillic acid, 5-hydroxy-3-methoxybenzoic acid, 2,3-dimethoxybenzoic acid, 2,4-dimethoxybenzoic acid, 2,5-dimethoxybenzoic acid, 2,6-dimethoxybenzoic acid, veratric acid (3,4-dimethoxybenzoic acid), 3,5-dimethoxybenzoic acid, gallic acid, 2,3,4-trihydroxybenzoic acid, 2,3,6-trihydroxybenzoic acid, 2,4,5-trihydroxybenzoic acid, 3-O-methylgallic acid (3-OMGA), 4-O-methylgallic acid (4-OMGA), 3,4-O-dimethylgallic acid, syringic acid, and 3,4,5-trimethoxybenzoic acid.

89. The compound or composition of paragraph 87 wherein the heteroaryl carboxylic acid is selected from the group consisting of nicotinic acid, isonicotinic acid, picolinic acid, 3-hydroxypicolinic acid, 6-hydroxynicotinic acid, citrazinic acid, 2,6-dihydroxynicotinic acid, kynurenic acid, xanthurenic acid, 6-hydroxykynurenic acid, 8-methoxykynurenic acid, 7,8-dihydroxykynurenic acid, and 7,8-dihydro-7,8-dihydroxykynurenic acid.

90. The compound or composition of paragraph 86, wherein the aromatic carboxylic acid is a phenylacetate selected from the group consisting of phenylacetic acid (hydratropic acid), 2-hydroxyphenylacetic acid, 3-hydroxyphenylacetic acid, 4-hydroxyphenylacetic acid, homoprotocatechuic acid, homogentisic acid, 2,6-dihydroxyphenylacetic acid, homovanillic acid, homoisovanillic acid, homoveratric acid, atropic acid, d,l-tropic acid, diclofenac, d,l-mandelic acid, 3,4-dihydroxy-d,l-mandelic acid, vanillyl-d,l-mandelic acid, isovanillyl-d,l-mandelic acid, ibuprofen, fenoprofen, carprofen, flurbiprofen, ketoprofen, and naproxen.

91. The compound or composition of paragraph 86, wherein the aromatic carboxylic acid is a benzylacetate selected from the group consisting of benzylacetic acid, melilotic acid, 3-hydroxyphenylpropanoic acid, 4-hydroxyphenylpropanoic acid, 2,3-dihydroxyphenylpropanoic acid, d,l-phenyllactic acid, o,m,p-hydroxy-d,l-phenyllactic acid, and phenylpyruvic acid.

92. The compound or composition of paragraph 86, wherein the aromatic carboxylic acid is a cinnamate, selected from the group consisting of cinnamic acid, o,m,p-coumaric acid, 2,3-dihydroxycinnamic acid, 2,6-dihydroxycinnamic acid, caffeic acid, ferulic acid, isoferulic acid, 5-hydroxyferulic acid, sinapic acid, and 2-hydroxy-3-phenylpropenoic acid.

93. The compound or composition of paragraph 71 or 73, wherein the carboxylic acid is a dicarboxylic acid of the general formula HOOC—R—COOH, where R is selected from the group consisting of an alkyl, alkenyl, alkynyl, arylgroup, and derivatives thereof.

94. The compound or composition of paragraph 93, wherein the dicarboxylic acid is selected from the group consisting of oxalic, malonic, succinic, glutaric, adipic, pimelic, suberic, azelaic, sebacic, brassylic, thapsic, malic, tartaric, dihydroxymesoxalic, α-hydroxyglutaric, methylmalonic, meglutol, diaminopimelic, carbamoyl aspartic, fumaric, maleic, mesaconic, 3-methylglutaconic, traumatic, phthalic acid, isophthalic, terephthalic, and dipicolinic acid.

95. The compound or composition of paragraph 71 or 73, wherein the carboxylic acid is a polycarboxylic acid selected from the group consisting of citric acid, isocitric, carballylic, and trimesic acid.

96. The compound or composition of paragraph 68, wherein $G^1$ and/or $G^2$ is at least one polyethylene glycol.

97. The compound or composition of paragraph 96, wherein the terminal hydroxyl group of the polyethylene glycol is substituted with an amino, azide, or methoxy group.

98. The compound or composition of paragraph 68, wherein $G^1$ and/or $G^2$ is at least one vitamin compound, and m is 1-3.

99. The compound or composition of paragraph 98 wherein the at least one vitamin compound is selected from ascorbic acid, riboflavin, thiamin, pantothenic acid, pyridoxine, pyridoxamine, pyridoxal, biotin, folic acid, niacin, pantothenic acid, retinol, cholecalciferol, ergocalciferol, and tocopherols.

100. The compound or composition of paragraph 68 wherein the at least one conjugate of dextrorphan comprises 3-acetyl-N-(acetyl-OCH$_2$)-dextrorphanium having the following structural formula, or a pharmaceutically acceptable salt thereof:

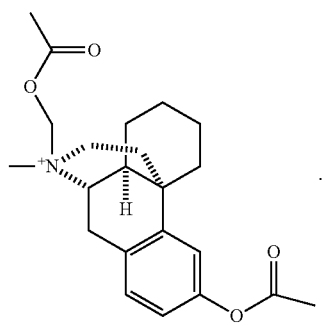

101. The compound or composition of any one of paragraphs 1-100, wherein the pharmaceutically acceptable salt of the conjugate is a pharmaceutically acceptable anionic salt form or salt mixtures thereof.

102. The compound or composition of paragraph 101, wherein the anionic salt form is selected from the group consisting of acetate, l-aspartate, besylate, bicarbonate, carbonate, d-camsylate, l-camsylate, citrate, edisylate, formate, fumarate, gluconate, hydrobromide/bromide, hydrochloride/chloride, d-lactate, i-lactate, d,l-lactate, d,l-malate, l-malate, mesylate, pamoate, phosphate, succinate, sulfate, bisulfate, d-tartrate, l-tartrate, d,l-tartrate, meso-tartrate, benzoate, gluceptate, d-glucuronate, hybenzate, isethionate, malonate, methylsulfate, 2-napsylate, nicotinate, nitrate, orotate, stearate, tosylate, thiocyanate, acefyllinate, aceturate, aminosalicylate, ascorbate, borate, butyrate, camphorate, camphocarbonate, decanoate, hexanoate, cholate, cypionate, dichloroacetate, edentate, ethyl sulfate, furate, fusidate, galactarate (mucate), galacturonate, gallate, gentisate, glutamate, glutarate, glycerophosphate, heptanoate (enanthate), hydroxybenzoate, hippurate, phenylpropionate, iodide, xinafoate, lactobionate, laurate, maleate, mandelate, methanesulfonate, myristate, napadisilate, oleate, oxalate, palmitate, picrate, pivalate, propionate, pyrophosphate, salicylate, salicylsulfate, sulfosalicylate, tannate, terephthalate, thiosalicylate, tribrophenate, valerate, valproate, adipate, 4-acetamidobenzoate, camsylate, octanoate, estolate, esylate, glycolate, thiocyanate, or undecylenate.

103. The compound or composition of any one of paragraphs 1-102, wherein the at least one conjugate is present in an amount of about 0.5 mg or higher, about 2.5 mg or higher, about 5 mg or higher, about 10 mg or higher, about 20 mg or higher, about 50 mg or higher, or about 100 mg or higher.

104. The compound or composition of any one of paragraphs 1-103, wherein the at least one conjugate is provided in a dosage form selected from the group consisting of: a tablet, a capsule, a caplet, a suppository, a troche, a lozenge, an oral powder, a solution, an oral film, a thin strip, a slurry, and a suspension.

105. The compound or composition of any one of paragraphs 1-104, wherein the at least one conjugate exhibits a slower rate of release over time as compared to unmodified dextrorphan.

106. The composition of any one of paragraphs 1-105, wherein the composition further comprises one or more excipients.

107. The composition of paragraph 106, wherein the one or more excipients is at least one filler, at least one glidant, at least one binder, at least one diluent, at least one lubricant, at least one surfactant, at least one plasticizer, at least one disintegrant, or a combination thereof.

108. The composition of any one of paragraphs 1-107, wherein the composition further comprises at least one additional active pharmaceutical ingredient.

109. The composition of paragraph 108, wherein the additional active pharmaceutical ingredient is one or more of acetaminophen, phenylpropanolamine, ibuprofen, aspirin, diflusinal, salicylic acid, dexibuprofen, naproxen, fenoprofen, ketoprofen, dexketoprofen, flurbiprofen, oxaprozin, loxoprofen, indomethacin, tolmetin, sulindac, etodolac, ketorolac, diclofenac, piroxicam, meloxicam, tenoxicam, lornoxicam, isoxicam, mefenamic acid, meclofenamic acid, flufenamic acid, tolfenamic acid, celecoxib, valdecoxib, lumiracoxib, pheniramine, chlorpheniramine, fexofenadine, azelastine, hydroxyzine, diphenhydramine, desloratidine, loratidine, cyproheptadine, bromopheniramine, emedastine, levocabastine, carbinoxamine, levocetirizine, clemastine, cetirizine, phenylephrine, pseudoephedrine, oxymetazoline, pyrilamine, doxylamine, codeine, pholcodine, dextromethorphan, noscapine, butamirate, acetylcysteine, menthol, guaifenesin, or combinations thereof.

110. The composition of paragraph 108, wherein the additional active pharmaceutical ingredient is in the form of a second conjugate.

111. The composition of paragraph 110, wherein the second conjugate is a dextrorphan conjugate that is different from the at least one conjugate.

112. A method of treating a patient having opioid dependence, hyperalgesia, pseudobulbar affect (PBA), neuropathy, diabetic peripheral neuropathic pain, catalepsy, amnesia, Alzheimer's disease, depression, post-traumatic stress disorder (PTSD), cough, impulse to cough, sneezing, itching of the nose, throat or watery eyes, nasal congestion, sinus congestion and pressure, sore throat, headache, muscular pain, fever, upper respiratory symptoms, or bronchial irritation, comprising orally administering to the patient a pharmaceutically effective amount of a composition comprising at least one conjugate of dextrorphan and at least one oxoacid, polyethylene glycol, vitamin compound, or a combination thereof.

113. The method of paragraph 112, wherein the patient is a pediatric patient.

114. The method of paragraph 112, wherein the patient is an elderly patient.

115. The method of paragraph 112, wherein the patient is a normative patient.

116. The method of paragraph 112, wherein the patient is a neonatal patient.

117. The method of paragraph 112, wherein the patient is an adolescent patient.

118. A pharmaceutical kit comprising:
 a specified amount of individual doses in a package, each dose comprising
 a pharmaceutically effective amount of at least one conjugate of dextrorphan and at least one oxoacid, polyethylene glycol, vitamin compound, or a combination thereof.

119. The pharmaceutical kit of paragraph 118, wherein the kit further comprises:
 instructions for use of the kit in a method for treating cough, sneezing, itching of the nose, throat or watery eyes, nasal congestion, sinus congestion and pressure, sore throat, headache, muscular pain, fever, upper respiratory symptoms, or bronchial irritation in a human or animal patient.

120. The pharmaceutical kit of paragraph 118 or 119, wherein the kit further comprises one or more additional compositions containing one or more other active ingredients.

121. The pharmaceutical kit of paragraph 118 or 119, wherein the individual doses in the kit comprise at least two different dosage strengths of the at least one dextrorphan conjugate.

The presently described technology is now described in such full, clear, concise and exact terms as to enable any person skilled in the art to which it pertains, to practice the same. It is to be understood that the foregoing describes preferred embodiments of the technology and that modifications may be made therein without departing from the spirit or scope of the invention as set forth in the appended claims.

What is claimed is:

1. A compound having the following general formula:

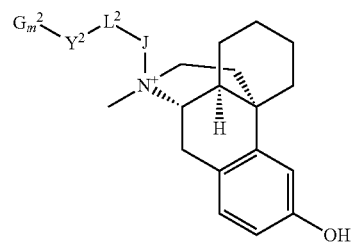

where $L^2$ is absent, or is

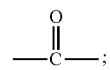

$Y^2$ is absent, or $[A-X-Z]_n$ where A and Z are independently absent or selected from —O—, —S— or —(CR$^1$R$^2$)$_k$— and where X is —(CR$^1$R$^2$)$_k$—,

J is [M-W]$_p$ where M is —(CR$^3$R$^4$)$_q$—; and W is absent, or —O— or —S—

R$^1$, R$^2$, R$^3$, R$^4$ are each independently selected from H, alkyl, aryl, alkylaryl, alkoxy, haloalkyl, or haloaryl n and k are independently selected from 1-4 p and q are independently selected from 1-4

G$_m^2$ is selected independently for each repeating subunit from, oxoacid, polyethylene glycol having from 2 to 5 ethylene oxide units, or a vitamin compound, and m is 1-4;

or a pharmaceutically acceptable salt thereof.

2. The compound of claim 1, wherein where L$^2$ and Y$^2$ are absent, M is —(CR$^3$R$^4$)$_q$, G$^2$ is at least one oxoacid, and m is 1-3.

3. The compound of claim 1, wherein the at least one oxoacid is acetic acid.

4. The compound of claim 1 wherein the compound is N-(acetyl-OCH$_2$)-dextrorphanium having the following structural formula:

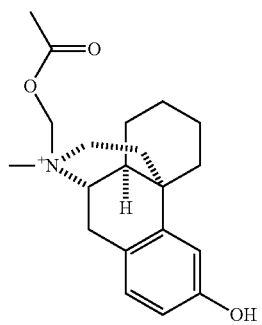

or a pharmaceutically acceptable salt thereof.

* * * * *